(12) United States Patent
Konishi

(10) Patent No.: US 8,139,911 B2
(45) Date of Patent: Mar. 20, 2012

(54) LIGHT-ILLUMINATING PROBE AND FUNDUS OBSERVING APPARATUS, FUNDUS SURGERY APPARATUS, ENDOSCOPE, AND CATHETER USING THE LIGHT-ILLUMINATING PROBE

(75) Inventor: Satoshi Konishi, Tokyo (JP)

(73) Assignee: Namiki Seimitsu Houseki Kabushiki Kaisha (JP)

( * ) Notice: Subject to any disclaimer, the term of this patent is extended or adjusted under 35 U.S.C. 154(b) by 637 days.

(21) Appl. No.: 12/195,534

(22) Filed: Aug. 21, 2008

(65) Prior Publication Data

US 2009/0156899 A1 Jun. 18, 2009

Related U.S. Application Data

(60) Provisional application No. 60/968,696, filed on Aug. 29, 2007.

(51) Int. Cl.
*G02B 6/02* (2006.01)
(52) U.S. Cl. .................................................. 385/123
(58) Field of Classification Search .................. None
See application file for complete search history.

(56) References Cited

U.S. PATENT DOCUMENTS

| | | | |
|---|---|---|---|
| 5,930,422 A | 7/1999 | Cheng | |
| 6,154,581 A | 11/2000 | Lu et al. | |
| 2005/0111102 A1 | 5/2005 | Iwatsuka | |
| 2005/0135749 A1* | 6/2005 | Nield et al. | 385/38 |
| 2008/0089089 A1* | 4/2008 | Hama et al. | 362/574 |
| 2009/0326525 A1* | 12/2009 | Hixon et al. | 606/15 |

FOREIGN PATENT DOCUMENTS

| | | |
|---|---|---|
| JP | 2000231080 | 8/2000 |
| JP | 2002228984 | 8/2002 |
| JP | 2002528765 | 9/2002 |
| JP | 2003111789 | 4/2003 |
| JP | 2006317614 | 11/2006 |
| JP | 2006317624 | 11/2006 |

OTHER PUBLICATIONS

International Search Report for PCT/JP2007/054531, Dated: Mar. 26, 2007.

* cited by examiner

*Primary Examiner* — Sung Pak
(74) *Attorney, Agent, or Firm* — Studebaker & Brackett PC; Donald R. Studebaker

(57) ABSTRACT

A light-illuminating probe with increased spatial spread of an external illumination light and a fundus observing apparatus, a fundus surgery apparatus, and an endoscope using the light-illuminating probe are provided. The light-illuminating probe includes a light-transmitting portion which is constructed with at least a first dielectric material having a light transparency and a light-radiating portion which is constructed with a second dielectric material having a light transparency to be formed in an extension portion of the light-transmitting portion.

2 Claims, 57 Drawing Sheets

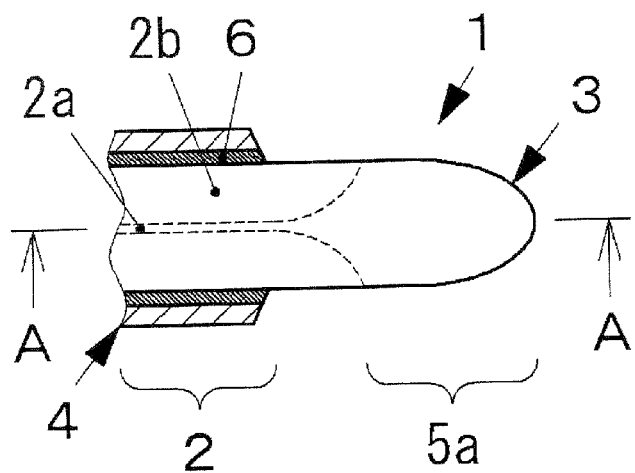
(a)
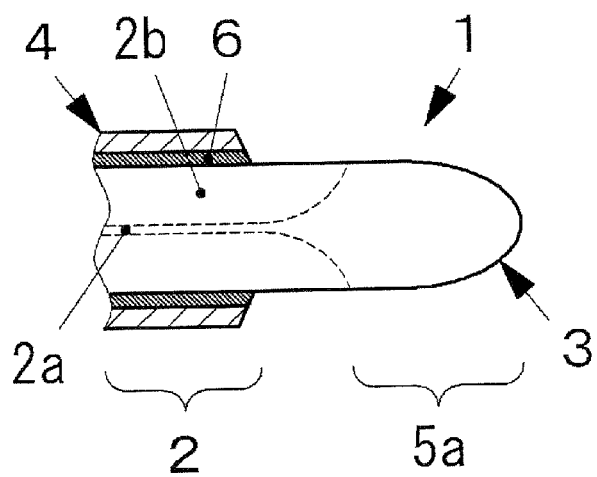
(b)
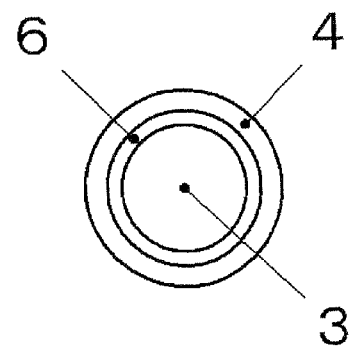
(c)
Fig. 1

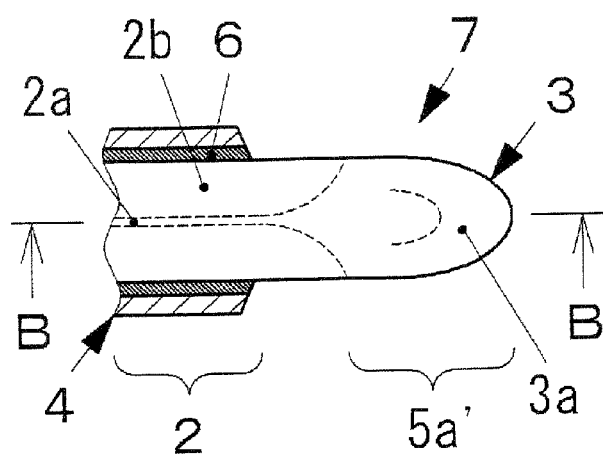
(a)
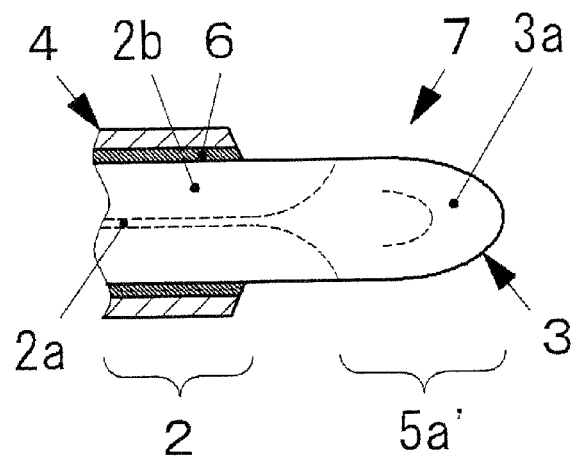
(b)
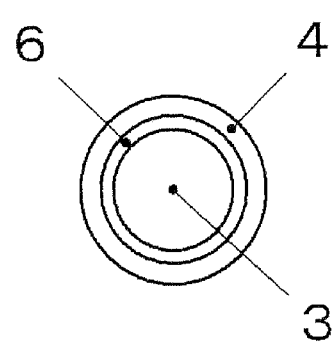
(c)
Fig. 4

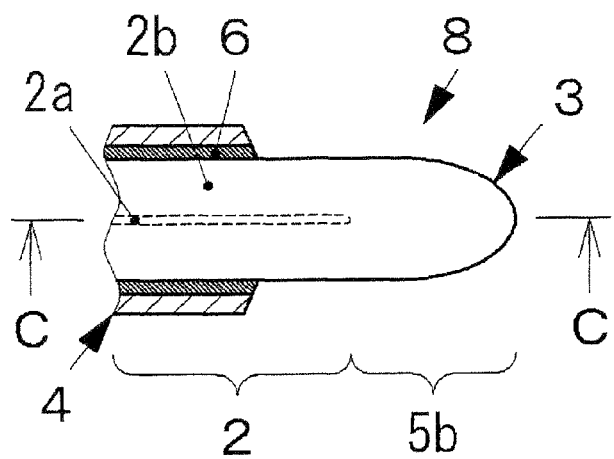
(a)
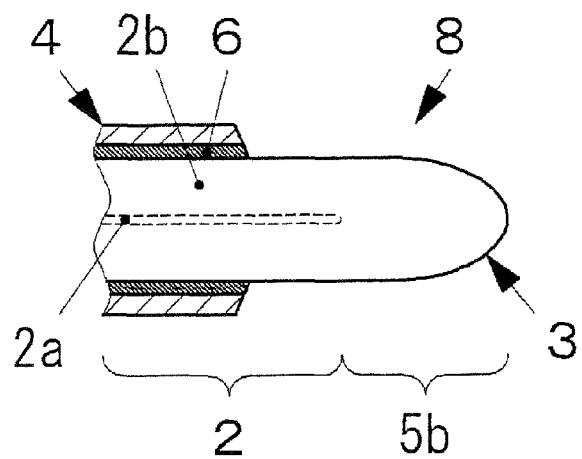
(b)
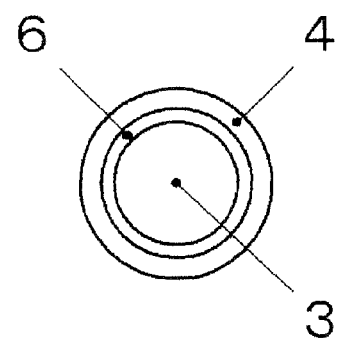
(c)
Fig. 7

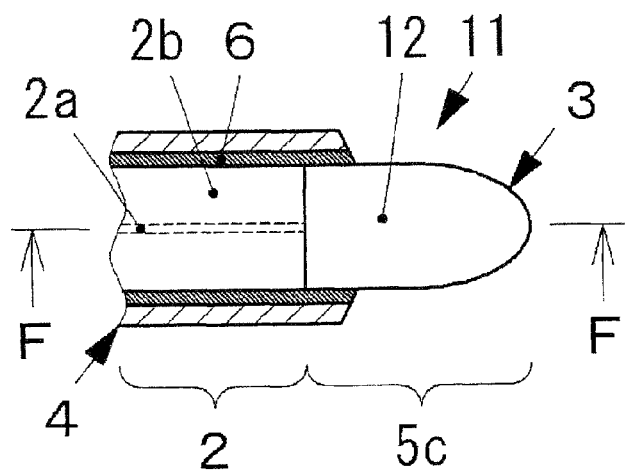
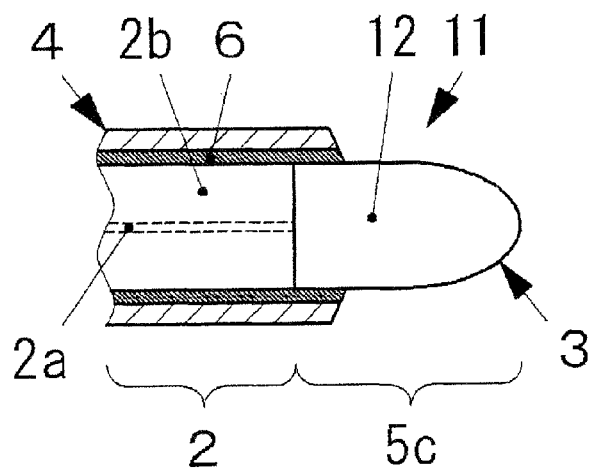
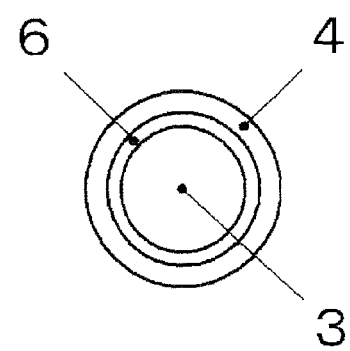
Fig. 17

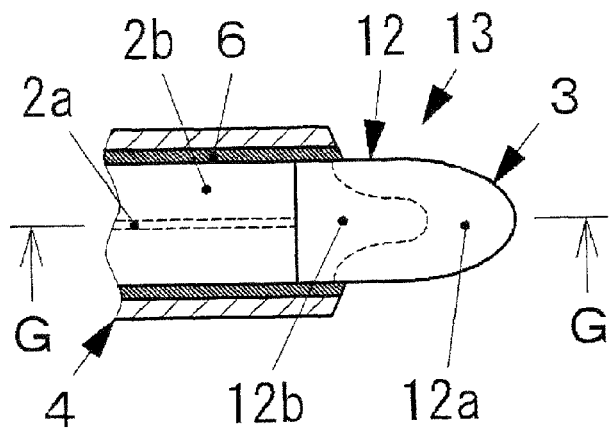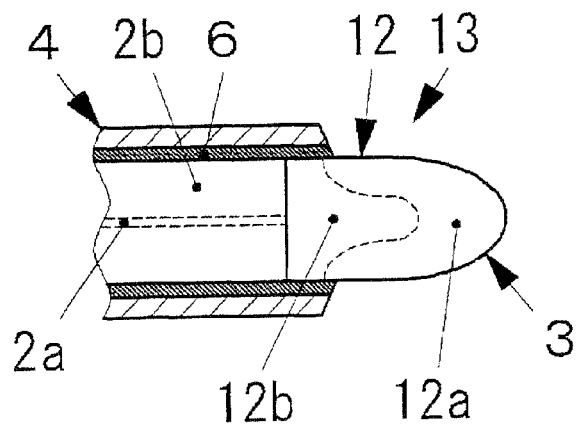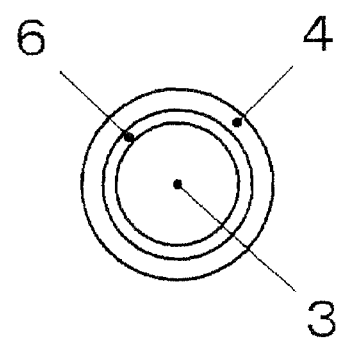
Fig. 20

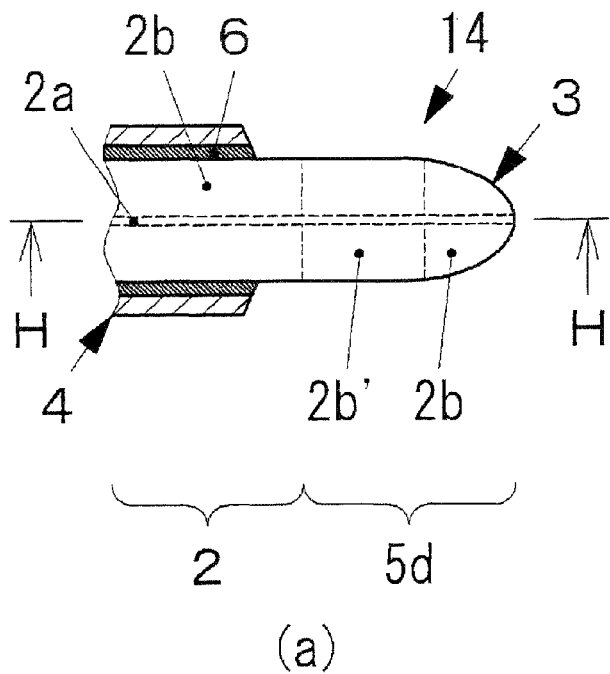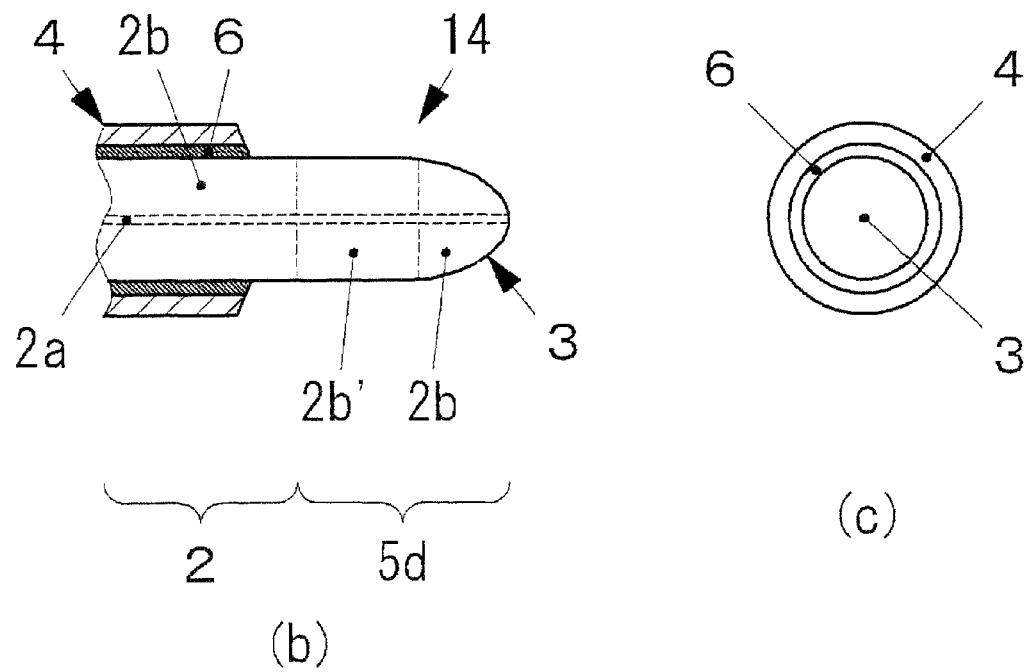
Fig. 23

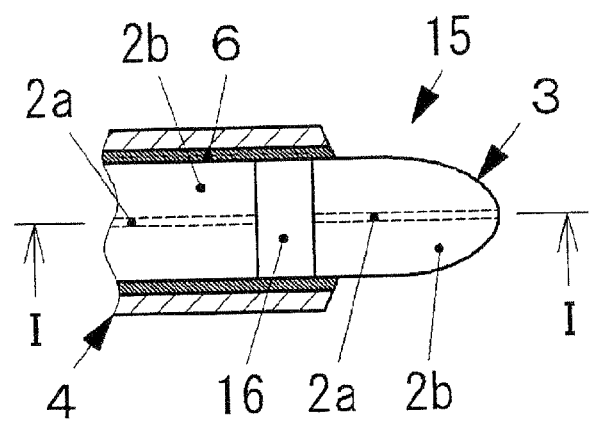
(a)
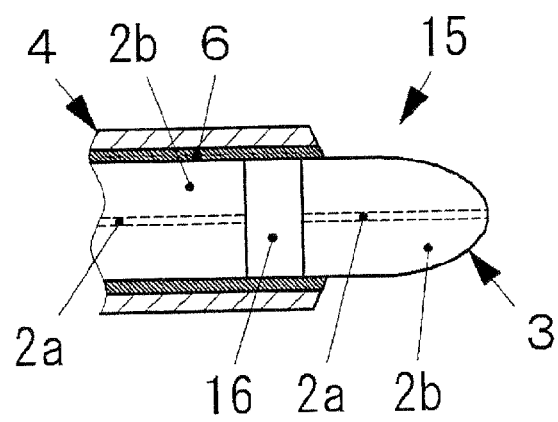 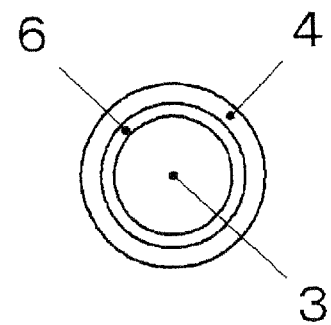
(b) (c)
Fig. 26

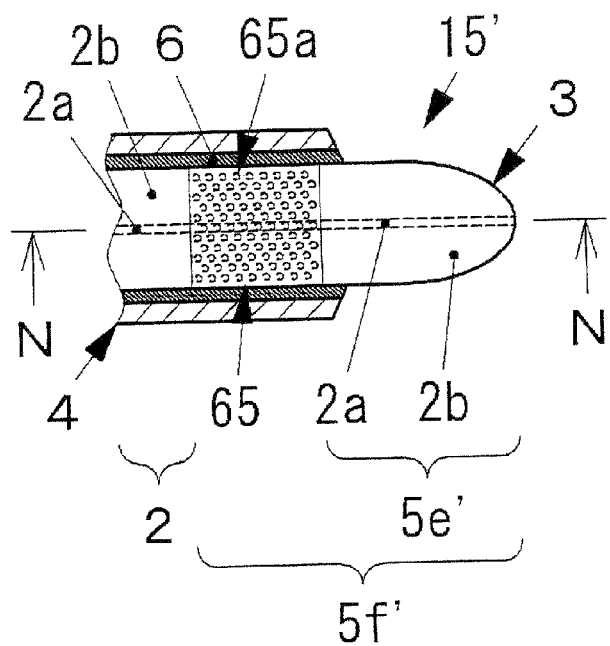
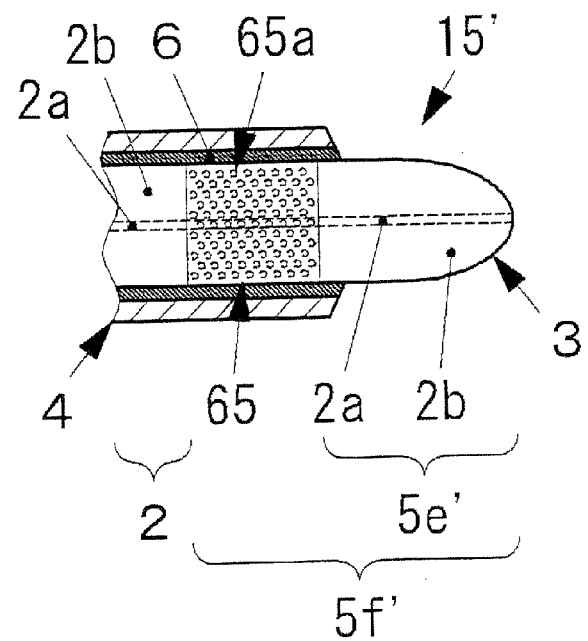
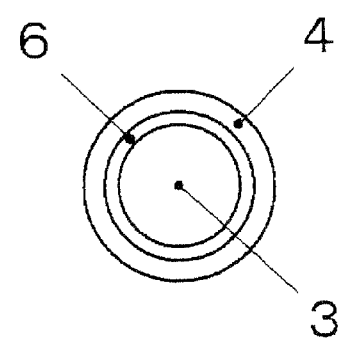
Fig. 29

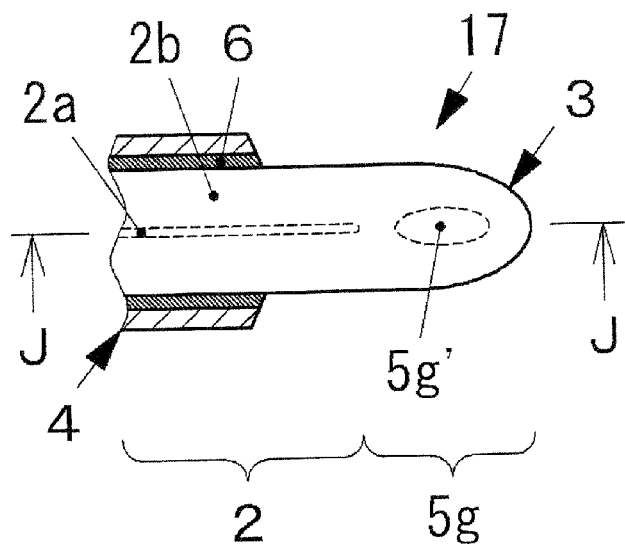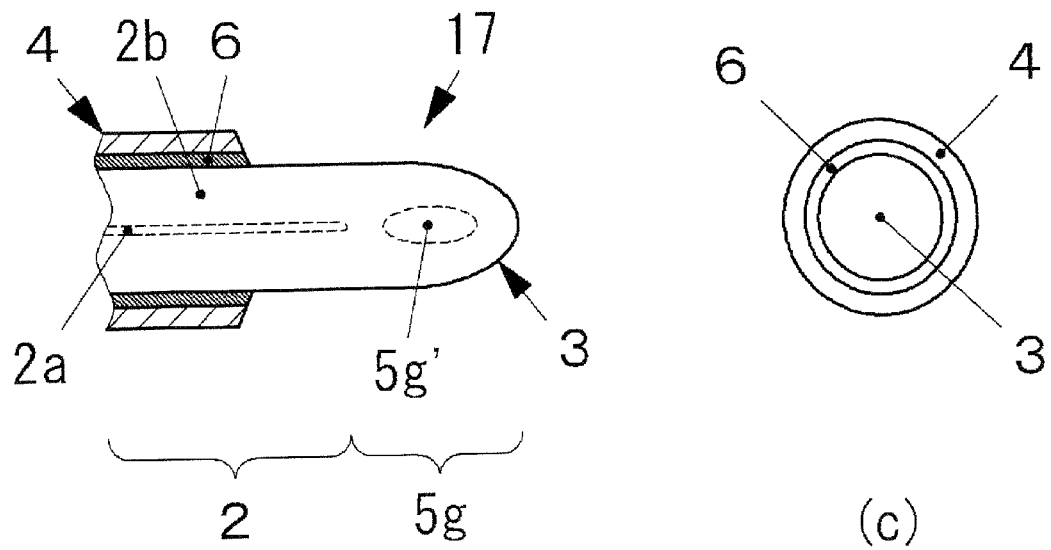
Fig. 32

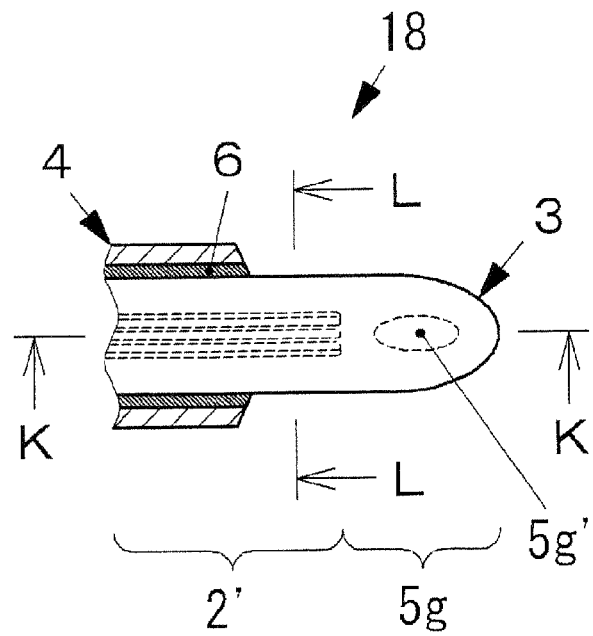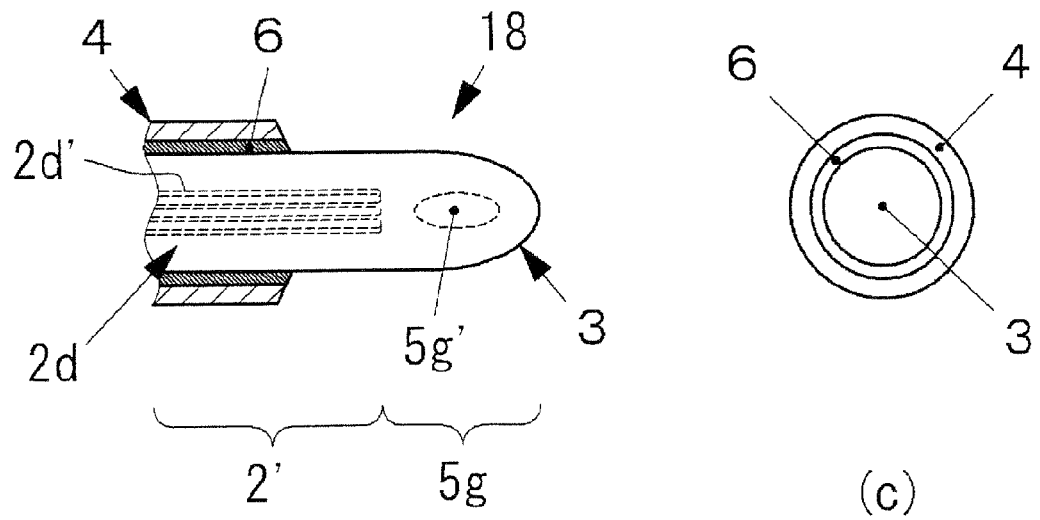
Fig. 36

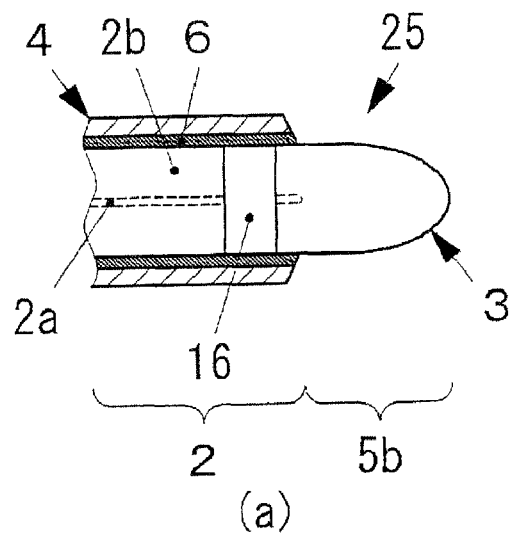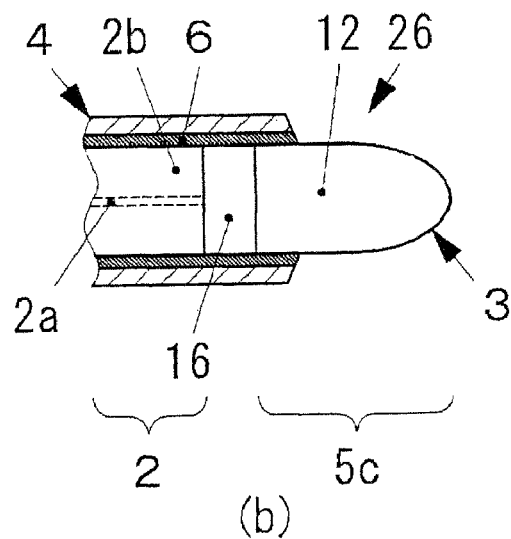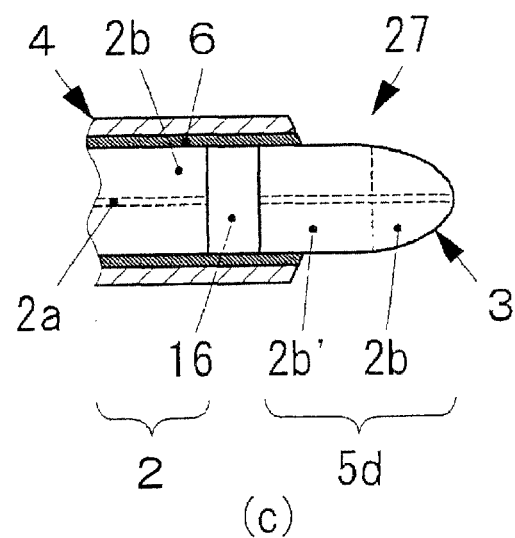
Fig. 41

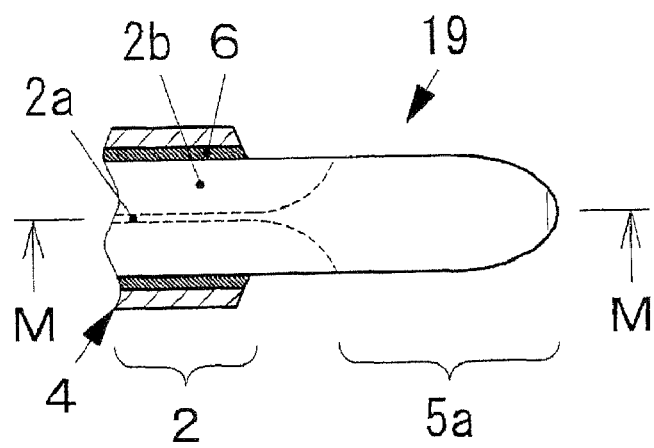
(a)
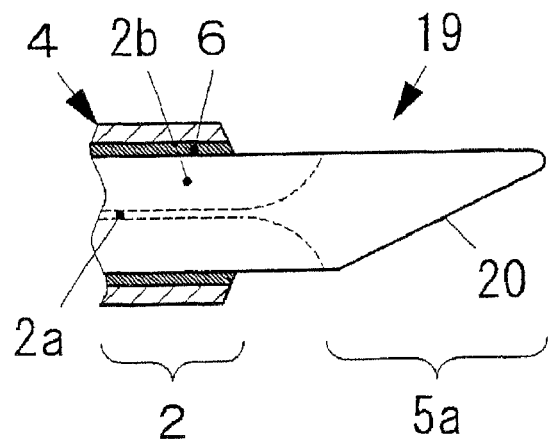
(b)
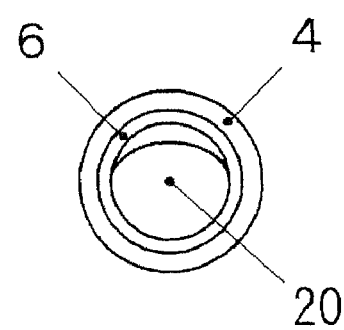
(d)
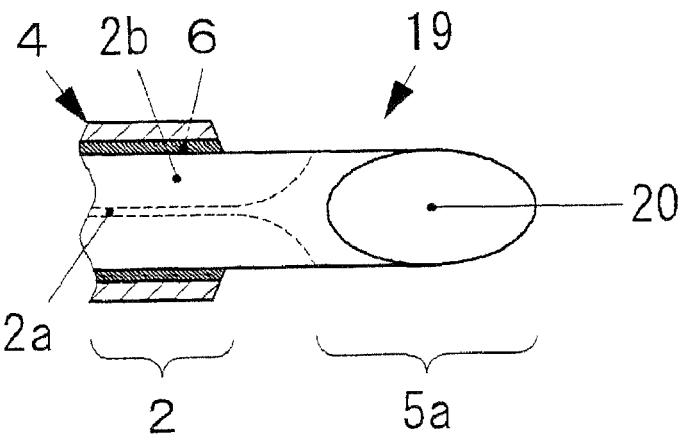
(c)
Fig. 42

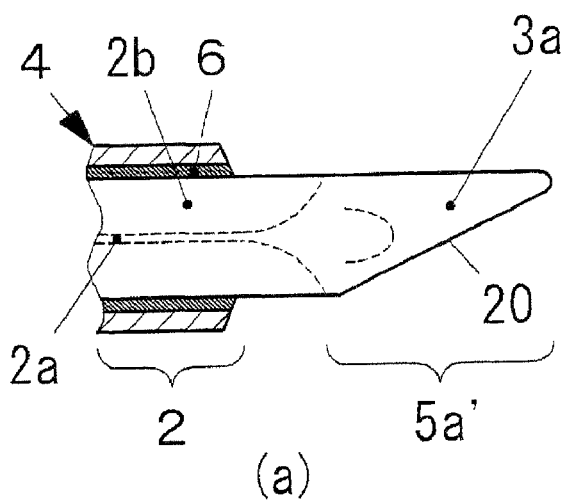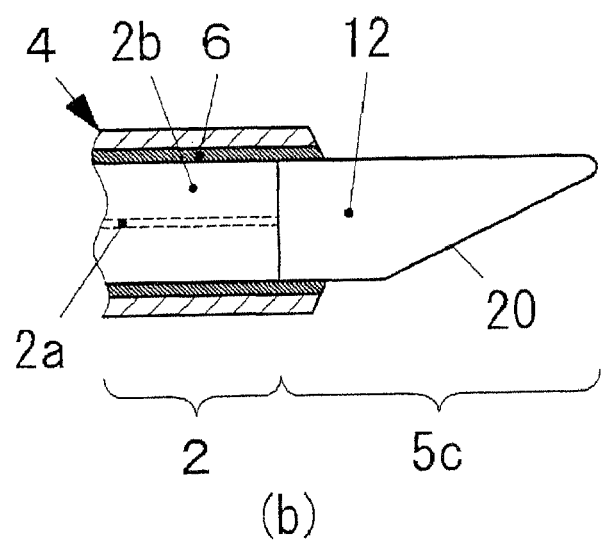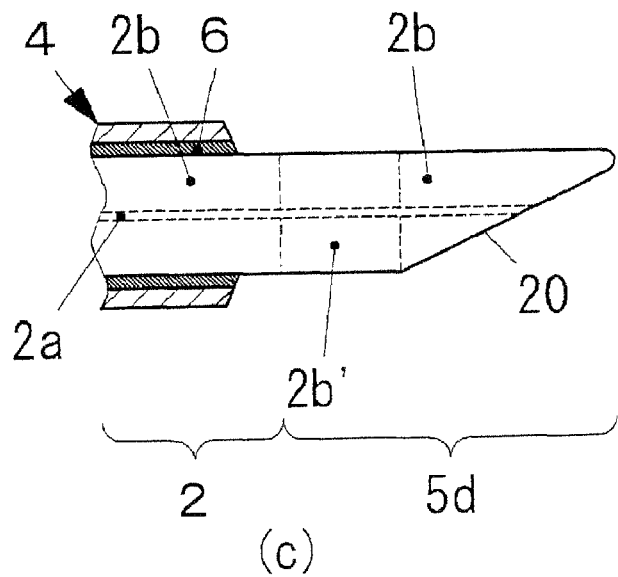
Fig. 45

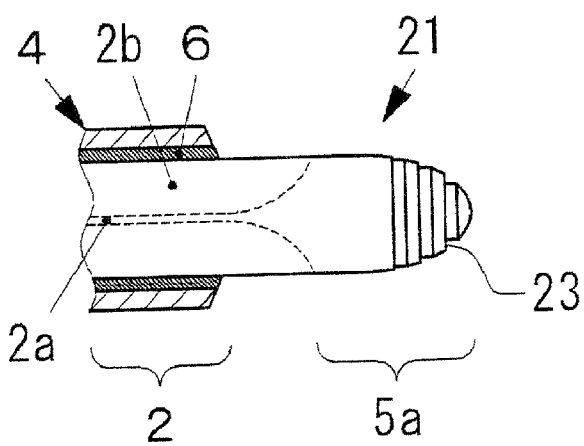
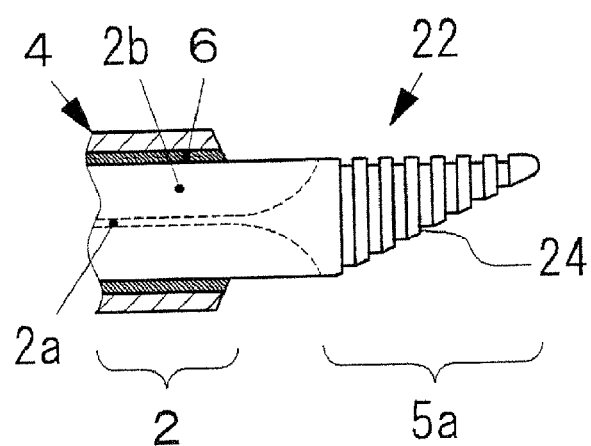
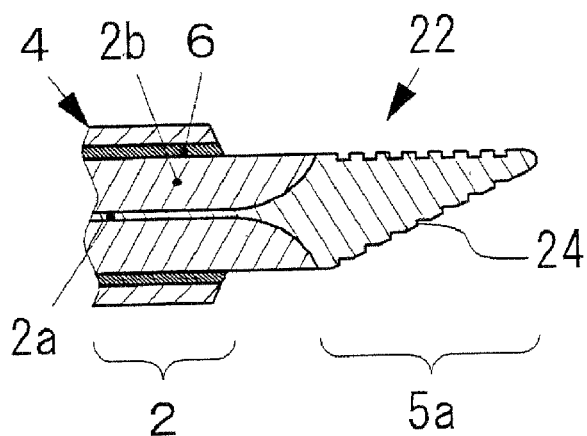
Fig. 46

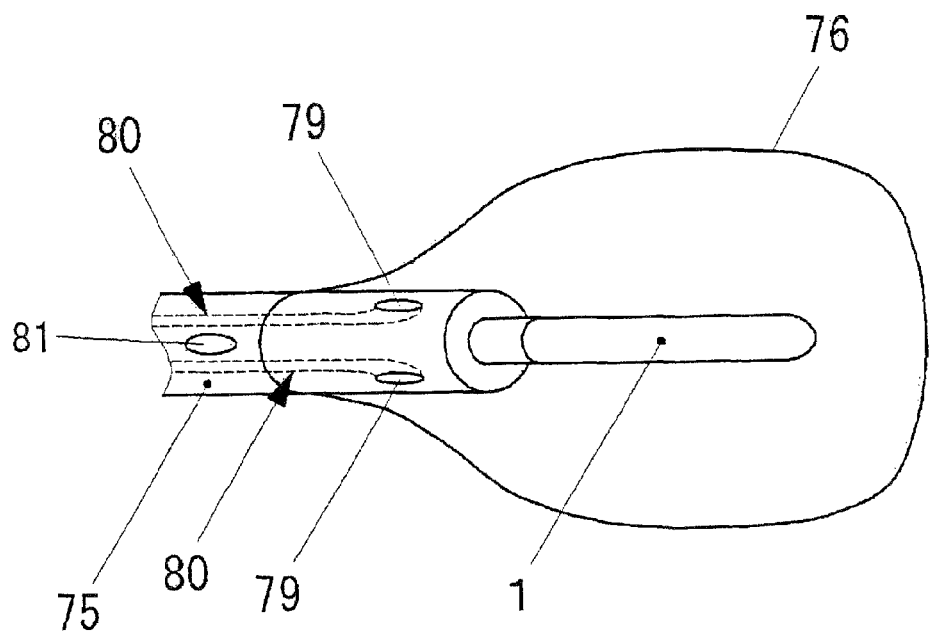
(a)
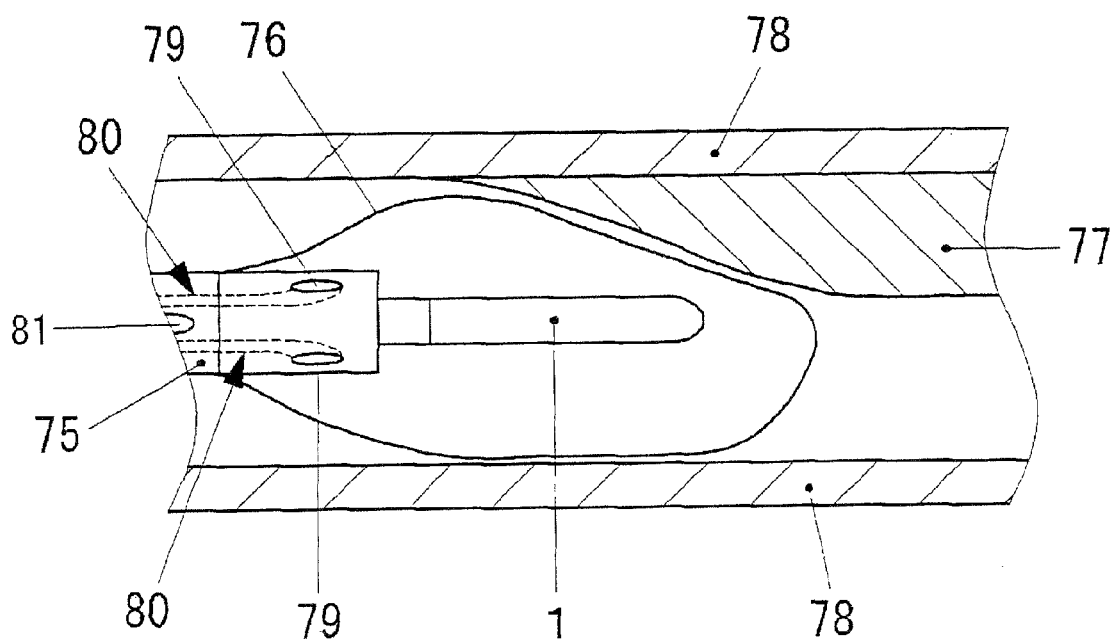
(b)
Fig. 57

LIGHT-ILLUMINATING PROBE AND FUNDUS OBSERVING APPARATUS, FUNDUS SURGERY APPARATUS, ENDOSCOPE, AND CATHETER USING THE LIGHT-ILLUMINATING PROBE

BACKGROUND

1. Field of the Invention

The present invention relates to a light-illuminating probe used for observing a specific cell, a diseased cell, a tumor, or a diseased part, and to a fundus observing apparatus, a fundus surgery apparatus, an endoscope, and a catheter using the light-illuminating probe.

2. Related Art

A fluorescence diagnosis method is well known as a diagnosis method for a cancer or a pathological lesion tissue in a medical field. The fluorescence diagnosis method is a method of detecting a specific cell or a diseased cell by marking the specific cell or the diseased cell with a fluorescent agent, illuminating the cell with an external light corresponding to absorption spectrum, and detecting fluorescent light emitted from the fluorescent agent.

In order to improve detection performance in the diagnosis method, it is necessary to increase an intensity of the external light (hereinafter, referred to as an external illuminating light or an illuminating light) that illuminates the fluorescent agent. Due to the increase in the intensity of the illuminating light, the marked specific cell or diseased cell can be easily detected with the strong fluorescent light emitted from the fluorescent agent.

A light illuminating surgical method that is called "photo-assist" is well known as a surgical method using the external illuminating light. In this surgical method, nano-shell particles having photo-absorption property are injected into a tumor or a diseased cell, and an external light is illuminated, so that the tumor or the like necrotizes or is thermally destructed by photothermal conversion of the nano-shell particles. In addition, a pharmacological therapy (photoreactive agent excitation method) is also well known as that treating a localized diseased part by using a photoreactive agent technique.

In these surgical methods, in order to accelerate necrosis or improve thermal destruction effect and an efficiency of generating a photo-induced reactive agent, it is necessary to increase the intensity of the external illuminating light. In order to increase the intensity of the external illuminating light, the following two requirements are considered.

As the first requirement, when a light illuminating apparatus illuminates a target object such as a specific cell, a diseased cell, a tumor, or a diseased part with an external illuminating light in close proximity thereto, the light illuminating apparatus must not obstruct a field of view for monitoring and observing the illuminated objective area by the separately-disposed monitoring/observing device. As the second requirement, an illuminated spatial range of the external illuminating light must be suitably set in order not to obstruct the field of view for monitoring and observing.

The first requirement is provided due to the following reason, such that, when the external illuminating light propagates through a body fluid or a Ringer's solution onto the diseased part, the light is scattered by micro granules in the body fluid or the Ringer's solution along the optical path of the light. The scattered light leads to flare, so that the target object cannot be easily detected, monitored, or observed by the monitoring/observing apparatus.

The second requirement is provided due to the following reason, such that, if the illuminated spatial range of the external illuminating light is narrow, only the actually-illuminated cells among the cells marked with the fluorescent agent can emit fluorescent light. Therefore, the object that all the marked specific cells, diseased cells, tumors, diseased parts are to be detected cannot be always detected.

In order to solve the problems, there is a method for illuminating the specific cells, diseased cells, tumors, or diseased parts by using an optical fiber provided for the purpose of the light illuminating apparatus in close proximity to the specific cells or the like. According to the method, although the light is illuminated in front of the optical monitoring/observing apparatus, the optical fiber does not obstruct the field of view since the optical fiber has a small size. In addition, since the optical fiber illuminates the target object in close proximity thereto, light scattering caused by the medium between the optical fiber and the target object can be reduced. Accordingly, the first requirement that the light illuminating apparatus in close proximity to the target object must not obstruct the field of view for monitoring and observing is satisfied.

In an inner portion of a core of the optical fiber explained above as provided for the purpose of the light illuminating apparatus, a wave front of the propagating light is maintained to be a flat plane which is perpendicular to an axis of the propagating light, but in an outside of the optical fiber, the wave front is not maintained to be the flat plane due to spread of the light propagating in a free space. The spread angle in the optical fiber is at most 5 degrees, and the illuminated spatial range of the illuminating light from the end portion of the optical fiber is narrow, that is, several degrees. Therefore, the field of view for monitoring and observing is narrowed. However, if the end portion of the optical fiber is moved backwards from the monitoring/observing apparatus so as to spread the illuminating light, scattering occurs, or some portion of the illuminating light is blocked by the monitoring/observing apparatus. Therefore, the field of view for monitoring and observing is obstructed. In order to solve the problems, it is necessary to increase spatial spread of the external illuminating light from the end surface of the optical fiber.

Conventionally, there has been contrived an end-portion structure for increasing the spatial spread of the external illuminating light by forming the end portion of the optical fiber in a parabolic shape such as a shape of bullet (for example, see Patent Document 1).

[Patent Document 1] Japanese Patent Application Publication No. 2003-111789 (P. 6-7, FIG. 2)

FIG. 50(*a*) is a cross-sectional view illustrating a part of a conventional light-illuminating probe 100 for which the optical fiber 102 has the aforementioned end-portion structure. FIG. 50(*b*) is a front view of the end portion corresponding to FIG. 50(*a*) regarding the conventional light-illuminating probe. Since the end portion of the light-illuminating probe 100 has a shape of a bullet in the end portion 101 of the optical fiber 102, the external illuminating light emitted from the end portion 101 of the optical fiber 102 is scattered so that the light can be illuminated with a wide spatial range.

Since the external illuminating light emitted from the end portion 101 of the optical fiber 102 spatially spreads, the illuminating light can be used for a photodynamic therapy (PDT). This is because uniform illumination in the peripheral directions of the optical fiber 102 can be obtained.

As another application, the external illuminating light of the optical fiber 102 can be used for dissolving the plaque or thrombus that causes blood vessel or artery to be narrowed, by using a photoactive agent and performing uniform illumination.

The shape of the end portion 101 of the optical fiber 102 is not limited to a specific one, but any parabolic shape of the longitudinal cross section of the end portion of a optical fiber 102 may be used.

In addition to the core/clad structure that is based on a difference between refractive indexes thereof or a difference caused by refractive index distribution, a light-guiding fiber constructed with a transparent dielectric material and a metal layer surrounding the transparent dielectric material or a hollow optical fiber including a plurality of hollow cylinders in a transparent dielectric material may be used as the optical fiber. Except for a case where a type of the optical fiber is specified, the aforementioned optical fibers are collectively referred to as an optical fiber for the simplification of description.

However, as shown in FIG. 51, the enlargement of the illuminated spatial range of the external illuminating light by using only the scattering at the end portion 101 of the optical fiber 102 also leads to back scattering light 103. Due to the back scattering light 103, the micro granules in the body fluid or the Ringer's solution located behind the end portion of the optical fiber 102 collide with the back scattered light, so that flare occurs in the field of view of the monitoring/observing apparatus located behind the end portion 101 of the optical fiber 102. Therefore, an image having the so-called poor "clearness" is obtained in the field of view, so that the fluorescent light cannot be easily detected.

In addition, the expansion of the illuminated spatial range of the external illuminating light by using only the scattering at the end portion 101 of optical fiber 102 leads to a decrease in intensity of the light that is to be induced to the distal end portion of the probe among the light induced through a light-transmitting portion due to the back scattering light 103. Therefore, there is a need for increasing the intensity of light that is induced to the optical fiber 102.

In addition, since the end portion 101 of the optical fiber 102 is subject to a rounding process, the light-illuminating probe 100 illustrated in FIG. 50(a) has a problem such that the wave front of the propagating light at the end portion 101 of the optical fiber 102 is curved. After emission to the free space, the propagating light is undesirably condensed due to the condensing function of the rounding-processed portion. Therefore, a desired spatial spread cannot be obtained.

SUMMARY OF THE INVENTION

The present invention is to provide a light-illuminating probe with increased spatial spread of an external illumination light and a fundus observing apparatus, a fundus surgery apparatus, an endoscope, and a photodynamic-therapy catheter using the light-illuminating probe. According to an aspect of the present invention, there is provided a light-illuminating probe comprising: a light-transmitting portion which is constructed with at least a first dielectric material having a light transparency; and a light-radiating portion which is constructed with a second dielectric material having a light transparency to be formed in an extension of the light-transmitting portion.

BRIEF DESCRIPTION OF THE DRAWINGS

FIG. 1(a) is a schematic partially cross-sectional view illustrating a light-illuminating probe given in a first embodiment of the present invention.

FIG. 1(b) is a schematic partial left-side cross-sectional view illustrating the light-illuminating probe given in the first embodiment.

FIG. 1(c) is a schematic front view illustrating the light-illuminating probe given in the first embodiment.

FIG. 4(a) is a schematic partially cross-sectional view illustrating a light-illuminating probe given in a second embodiment of the present invention.

FIG. 4(b) is a schematic partial left-side cross-sectional view illustrating the light-illuminating probe given in the second embodiment.

FIG. 4(c) is a schematic front view illustrating the light-illuminating probe given in the second embodiment.

FIG. 7(a) is a schematic partially cross-sectional view illustrating a light-illuminating probe given in a third embodiment of the present invention.

FIG. 7(b) is a schematic partial left-side cross-sectional view illustrating the light-illuminating probe given in the third embodiment.

FIG. 7(c) is a schematic front view illustrating the light-illuminating probe given in the third embodiment.

FIG. 17(a) is a schematic partially cross-sectional view illustrating a light-illuminating probe given in a sixth embodiment of the present invention.

FIG. 17(b) is a schematic partial left-side cross-sectional view illustrating the light-illuminating probe given in the sixth embodiment.

FIG. 17(c) is a schematic front view illustrating the light-illuminating probe given in the sixth embodiment.

FIG. 20(a) is a schematic partially cross-sectional view illustrating a light-illuminating probe given in a seventh embodiment of the present invention.

FIG. 20(b) is a schematic partial left-side cross-sectional view illustrating the light-illuminating probe given in the seventh embodiment.

FIG. 20(c) is a schematic front view illustrating the light-illuminating probe given in the seventh embodiment.

FIG. 23(a) is a schematic partially cross-sectional view illustrating a light-illuminating probe given in an eighth embodiment of the present invention.

FIG. 23(b) is a schematic partial left-side cross-sectional view illustrating the light-illuminating probe given in the eighth embodiment.

FIG. 23(c) is a schematic front view illustrating the light-illuminating probe given in the eighth embodiment.

FIG. 26(a) is a schematic partially cross-sectional view illustrating a light-illuminating probe given in a ninth embodiment of the present invention.

FIG. 26(b) is a schematic partial left-side cross-sectional view illustrating the light-illuminating probe given in the ninth embodiment.

FIG. 26(c) is a schematic front view illustrating the light-illuminating probe given in the ninth embodiment.

FIG. 29(a) is a schematic partially cross-sectional view illustrating a light-illuminating probe given in a tenth embodiment of the present invention.

FIG. 29(b) is a schematic partial left-side cross-sectional view illustrating the light-illuminating probe given in the tenth embodiment.

FIG. 29(c) is a schematic front view illustrating the light-illuminating probe given in the tenth embodiment.

FIG. 32(a) is a schematic partially cross-sectional view illustrating a light-illuminating probe given in an eleventh embodiment of the present invention.

FIG. 32(b) is a schematic partial left-side cross-sectional view illustrating the light-illuminating probe given in the eleventh embodiment.

FIG. 32(c) is a schematic front view illustrating the light-illuminating probe given in the eleventh embodiment.

FIG. 36(a) is a schematic partially cross-sectional view illustrating a light-illuminating probe given in a twelfth embodiment of the present invention.

FIG. 36(b) is a schematic partial left-side cross-sectional view illustrating the light-illuminating probe given in the twelfth embodiment.

FIG. 36(c) is a schematic front view illustrating the light-illuminating probe given in the twelfth embodiment.

FIG. 41(a) is a schematic partially cross-sectional view illustrating light-illuminating probes given in a thirteenth embodiment of the present invention.

FIG. 41(b) is a schematic partially cross-sectional view illustrating light-illuminating probes given in a thirteenth embodiment of the present invention.

FIG. 41(c) is a schematic partially cross-sectional view illustrating light-illuminating probes given in a thirteenth embodiment of the present invention.

FIG. 42(a) is a schematic partially cross-sectional view illustrating a light-illuminating probe given in a fourteenth embodiment of the present invention.

FIG. 42(b) is a schematic partial left-side cross-sectional view illustrating the light-illuminating probe given in the fourteenth embodiment.

FIG. 42(c) is a schematic bottom view illustrating the light-illuminating probe given in the fourteenth embodiment.

FIG. 42(d) is a schematic front view illustrating the light-illuminating probe given in the fourteenth embodiment.

FIG. 45(a) is a partial left-side cross-sectional view illustrating a light-illuminating probe in which a flat plane is provided to an end portion of the light-radiating portion given in the second embodiment.

FIG. 45(b) is a partial left-side cross-sectional view illustrating a light-illuminating probe in which a flat plane is provided to an end portion of the optical member given in the sixth embodiment.

FIG. 45(c) is a partial left-side cross-sectional view illustrating a light-illuminating probe in which a flat plane is provided to an end portion of the light-radiating portion given in the eighth embodiment.

FIG. 46(a) is a schematic partial left-side cross-sectional view illustrating the light-illuminating probe given in a fifteenth embodiment of the present invention.

FIG. 46(b) is a schematic partial left-side cross-sectional view illustrating another type of the fifteenth embodiment.

FIG. 46(c) is a cross-sectional view of FIG. 46(b).

FIG. 57(a) is a schematic view for explaining a catheter using a light-illuminating probe given in the present invention.

FIG. 57(b) is a view explaining a usage state that the catheter of FIG. 57(a) is inserted into a blood vessel.

DETAILED DESCRIPTION OF THE INVENTION

First Embodiment

Figure 2:
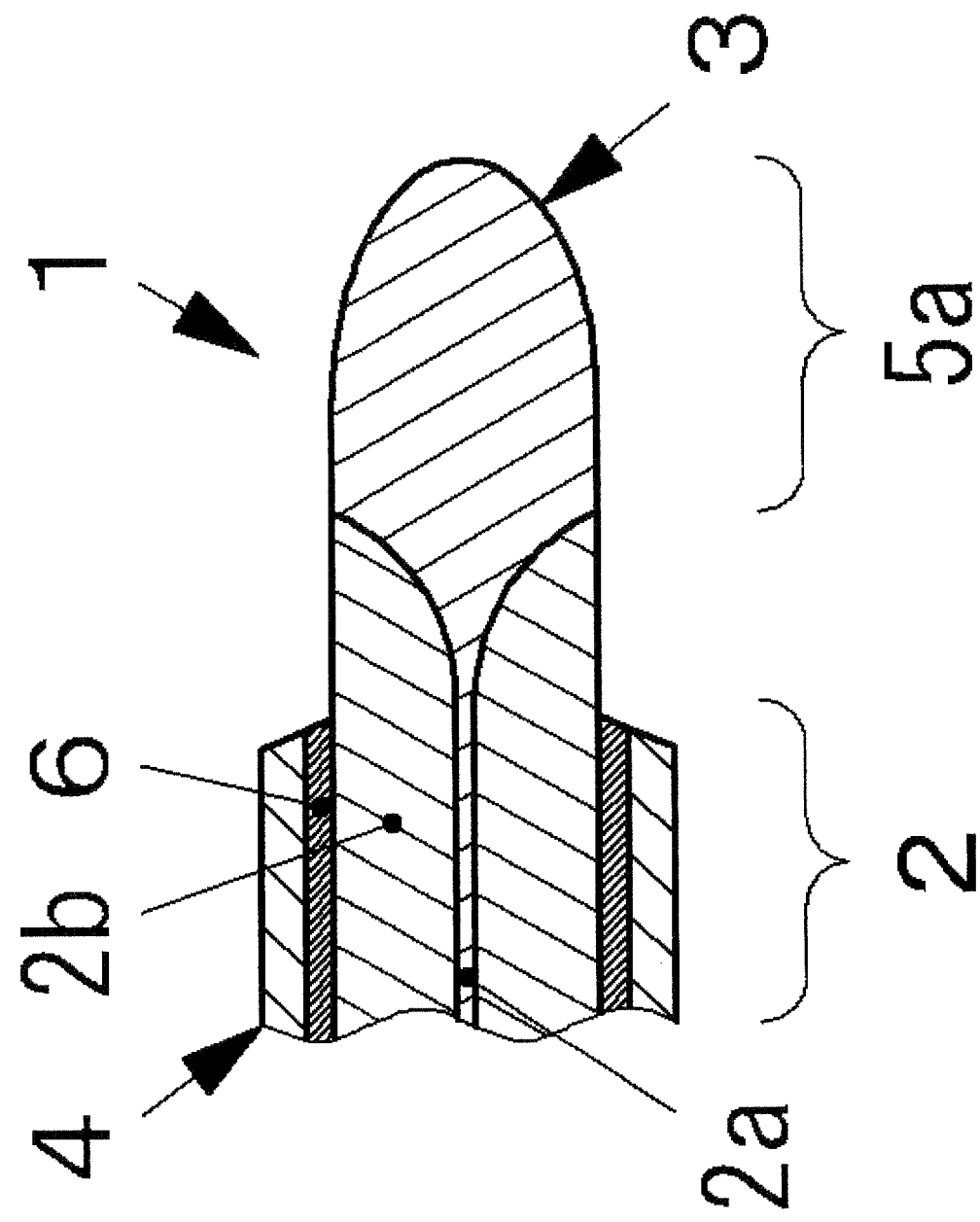
FIG. 2 is a cross-sectional view taken along line A-A of FIG. 1(a).
Figure 3:
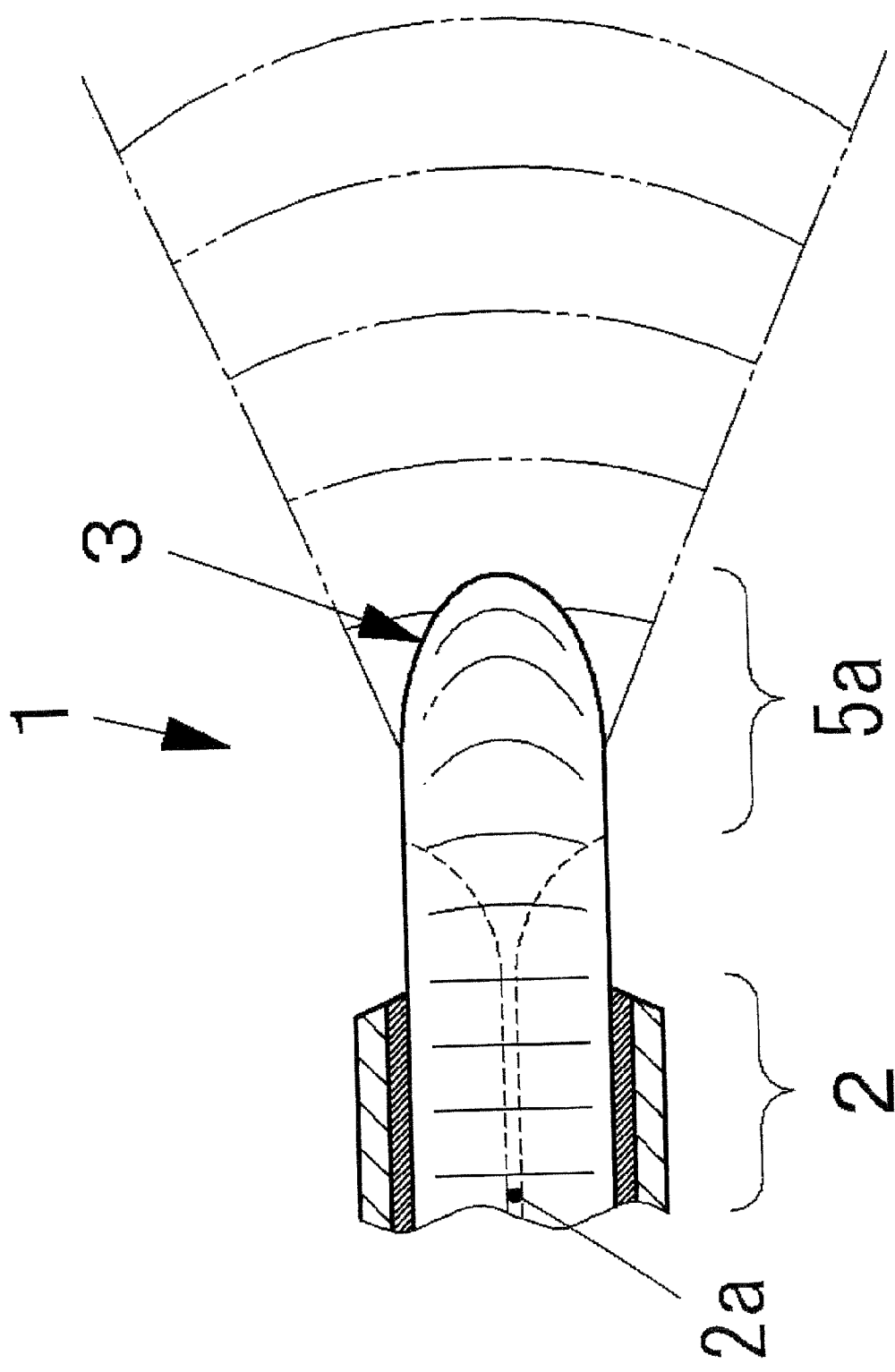
FIG. 3 is a schematic view illustrating propagation and radiation of light in the light-illuminating probe of FIG. 1.

FIGS. 1(a), (b) and (c) schematically illustrate a light-illuminating probe 1 given in a first embodiment of the present invention. FIG. 2 is a cross-sectional view taken along line A-A of FIG. 1(a). FIG. 3 illustrates propagation and radiation paths of light in the light-illuminating probe 1 given in this embodiment. The same components as those given in the different figures in the first embodiment are denoted by the same reference numerals, and the description thereof is omitted and simplified.

In FIGS. 1(a), (b) and (c), the light-illuminating probe 1 includes an optical fiber 2 that is a light-transmitting portion and a cannula 4 which is disposed on an outer circumferential surface of the optical fiber 2. A light-radiating portion 5a is integrated with the optical fiber 2 in an extended portion of the optical fiber 2. At a distal end of the light-radiating portion 5a, a distal end portion having a parabolic cross-section is formed by performing a grinding or polishing process. The distal end portion having a parabolic cross-section becomes a lens portion 3. In FIGS. 1 and 2, dashed lines and solid lines illustrated in an inner portion of the optical fiber 2 indicate boundaries between refractive indexes of a core 2a and a clad 2b.

The optical fiber 2 including the core 2a and the clad 2b has a spatial refractive index distribution in which the clad 2b having a refractive index lower than that of the core 2a surrounds the core 2a. The light-radiating portion 5a has a refractive index equal to that of the core 2a with a uniform (spatial) refractive index distribution. A region of the core 2a is gradually enlarged toward the outer circumferential surface of the optical fiber 2 as the region approaches the extension of the optical fiber 2, and the region of the core 2a is formed to cover the entire diameter of the clad 2b before the region of the core 2a approaches the lens portion 3. Due to such a construction, the light-radiating portion 5a can be formed to have the uniform refractive index distribution.

As illustrated in FIG. 3, the light that is incident to the other end portion (not shown) of the optical fiber 2 propagates through the inner portion of the optical fiber 2 toward the lens portion 3. Since the propagating light propagating through the inner portion of the optical fiber 2 is maintained in a propagation mode, wave fronts of the light are maintained to be perpendicular to an axis of the core 2a and to be parallel to each other.

Next, when the light propagates from the optical fiber 2 to the light-radiating portion 5a, the refractive index of the core 2a gradually spreads due to a change of the refractive index distribution, the refractive index becomes substantially uniform in the light-radiating portion 5a. Therefore, a total reflection of the propagating light disappears, so that the wave front is gradually changed from a flat plane to a curved plane. In addition, the mode of the propagating light is changed from a propagation mode to a radiation mode. The propagating light that approaches to the lens portion 3 is emitted as an external radiating light from the lens portion 3 to an outside of the light-illuminating probe 1. Since the mode of the propagating light in an inner portion of the light-radiating portion 5a is changed to the radiation mode, a condensing function of the lens portion 3 is reduced, and the propagation of the light in the free space is maintained more effectively in the radiation mode. Therefore, in comparison to a conventional light-illuminating probe, it is possible to enlarge an illuminated spatial range of the external illuminating light.

In addition, since the spread angle of the propagating light is increased before the propagating light approaches the lens portion 3, the illuminated spatial range of the external illuminating light can be enlarged, so that generation of back scattering light can be suppressed.

The outer circumferential surface of the optical fiber 2 and the inner circumferential surface of the cannula 4 are coupled to each other by a hermetic seal 6. The hermetic seal 6 is formed by plating or depositing, for example, Ni, Pd, Cu, Al, Au, or a combination thereof on the surface of the optical fiber 2, pressing the cannula 4 on the outer circumferential surface of the optical fiber 2, and performing a heating process. Alternatively, the hermetic seal 6 may be formed by using an adhesive. As a result, it is possible to preventing various germs from penetrating or remaining between the outer circumferential surface of the optical fiber 2 and the inner circumferential surface of the cannula 4. Alternatively, the cannula 4 may be provided to extend to an outer circumferential surface of the light-radiating portion 5a, and the hermetic seal 6 may be formed between the outer circumferential surface of the optical fiber 2 and the inner circumferential surface of the cannula 4 or between the outer circumferential surface of the light-radiating portion 5a and inner circumferential surface of the cannula 4.

In a method of manufacturing the light-radiating portion 5a, a distal end portion of the optical fiber 2 corresponding to a length of the light-radiating portion 5a in an axial direction of the optical fiber 2 is immersed into a fused benzoic acid, and proton exchange is performed so that the refractive index of a clad (not shown) of the light-radiating portion 5a increases up to the refractive index of the core 2a.

In an alternative method, MgO may be doped into an extension of the optical fiber 2, and the proton exchange may be performed. As a doping method, after ion injection, the extension of the optical fiber 2 may be subject to an annealing process, or the extension of the optical fiber 2 may be exposed to a vapor of a doping agent or a plasma ambience obtained from plasma of the vapor. Alternatively, the distal end portion of the optical fiber 2 may be immersed into a low-temperature fusing quartz pool in which a doping agent of Er, Nd, Ho, Tm, Pr, Sm, Dy, Yb, Ti, or the like is fused.

Due to the method, the light-radiating portion 5a is integrally formed in the extension of the optical fiber 2 in a direction matching with the axis of the optical fiber 2.

Second Embodiment

Figure 5:
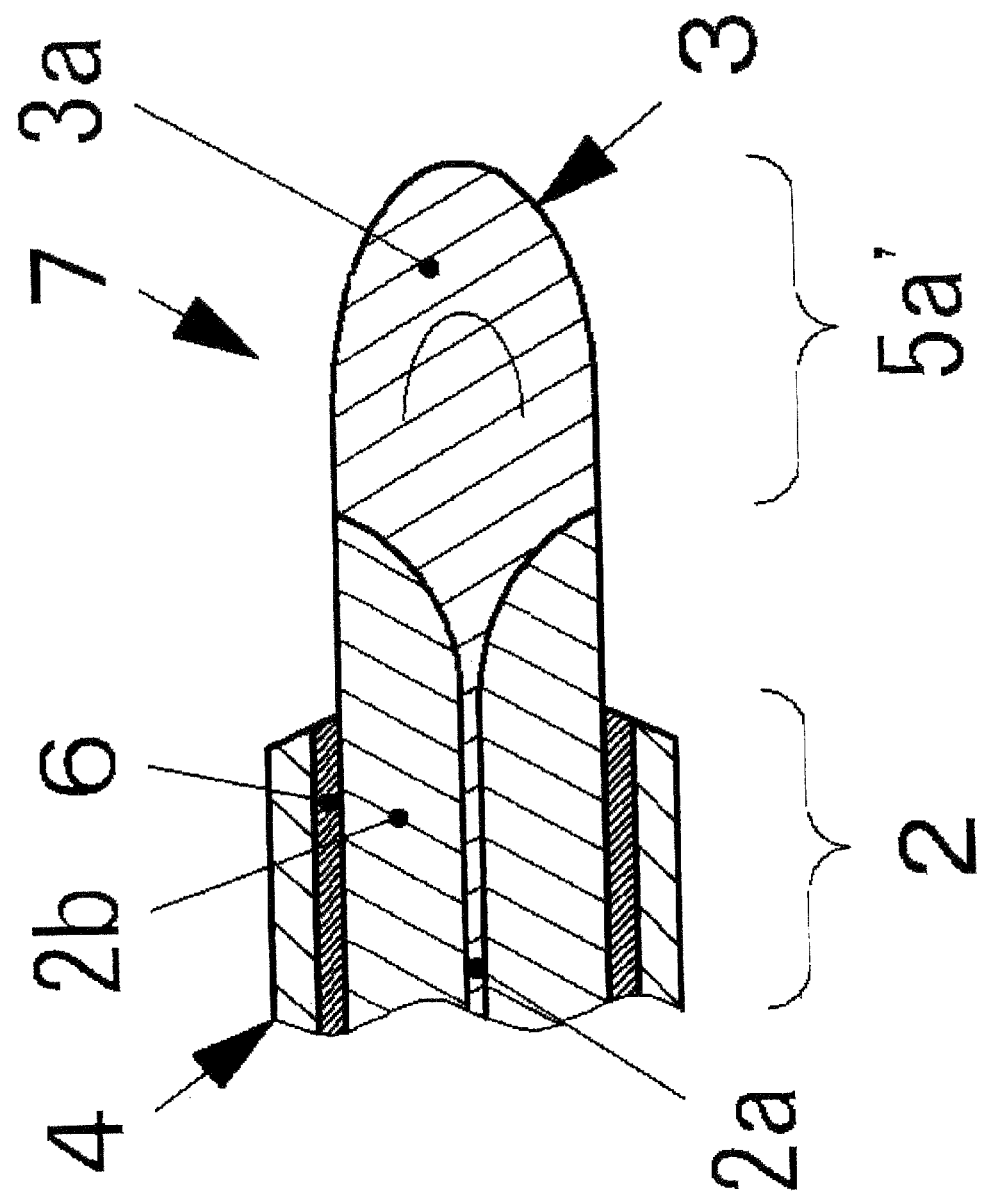
FIG. 5 is a cross-sectional view taken along line B-B of FIG. 4(a).
Figure 6:
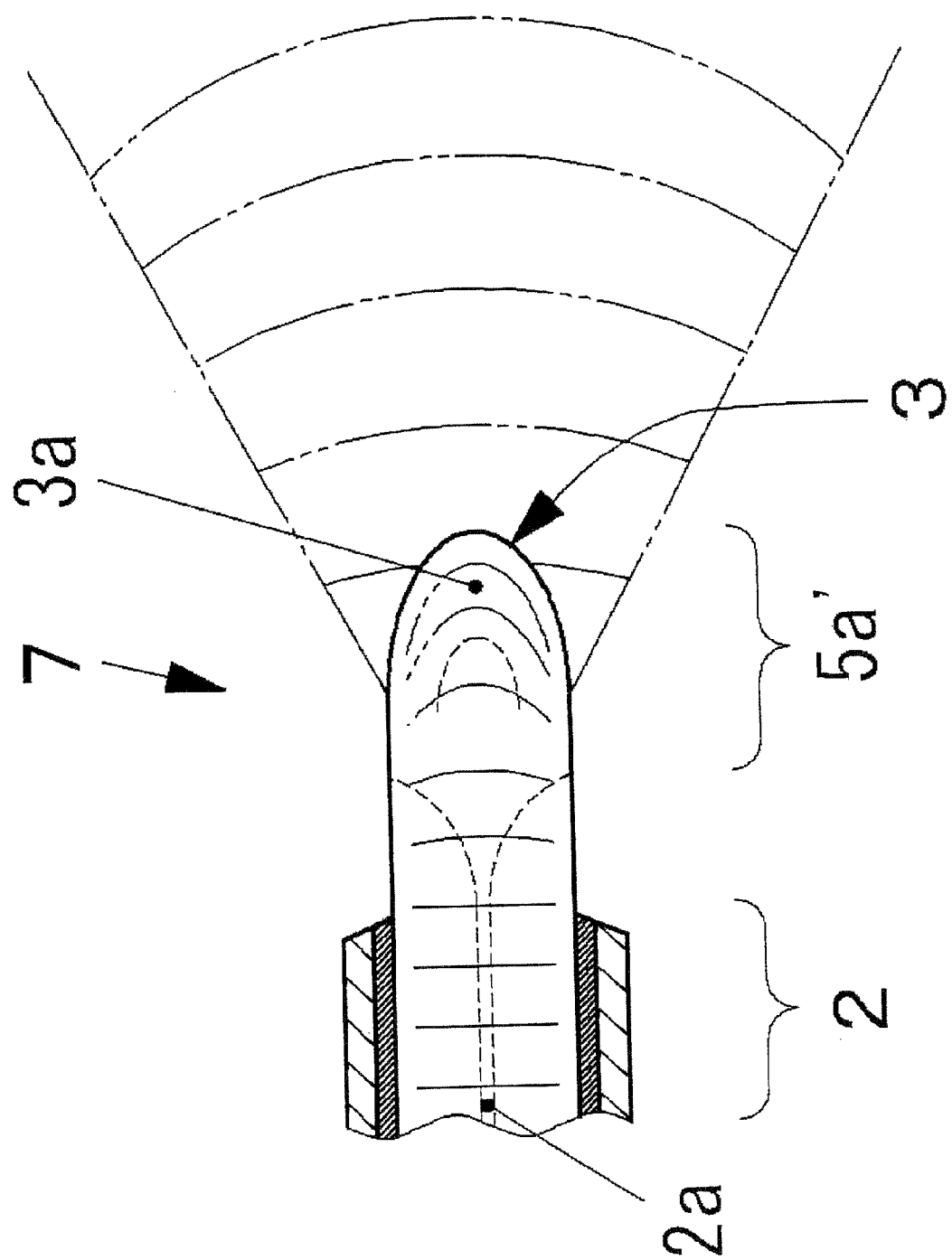
FIG. 6 is a schematic view illustrating propagation and radiation of light in the light-illuminating probe of FIG. 4

FIGS. 4 (*a*), (*b*) and (*c*) schematically illustrates a light-illuminating probe 7 given in a second embodiment of the present invention. FIG. 5 is a cross-sectional view taken along line B-B of FIG. 4 (*a*). FIG. 6 illustrates propagation and radiation paths of light in the light-illuminating probe 7 given in the present embodiment. The same components as those of the first embodiment are denoted by the same reference numerals, and the description thereof is omitted and simplified.

The second embodiment is different from the first embodiment in that a refractive index distribution (spatial refractive index distribution) of a light-radiating portion 5a' is formed to be uniform and equal to that of the core 2a, and a refractive index of a distal end portion 3a of a lens portion 3 in an inner portion of the light-radiating portion 5a' is set to be higher than that of the core 2a.

Now, a method of manufacturing the light-radiating portion 5a' is described. Steps of forming the refractive index distribution of the light-radiating portion 5a' to be uniform and equal to that of the core 2a illustrated in FIG. 5 are the same as those of the method given in the first embodiment, and thus, the description thereof is omitted. After the light-radiating portion 5a' of which refractive index distribution is uniform and equal to that of the core 2a is formed, the distal end portion 3a is doped with a doping agent of Er, Nd, Ho, Tm, Pr, Sm, Dy, Yb, Ti, or the like, so that only the refractive index of the distal end portion 3a is higher than that of the core 2a. As a doping method, after ion injection, the extension of the optical fiber 2 may be subject to an annealing process, or the extension of the optical fiber 2 may be exposed to a vapor of a doping agent or a plasma ambience obtained from plasma of the vapor. Alternatively, the distal end portion 3a of the optical fiber 2 may be immersed into a low-temperature fusing quartz pool in which the doping agent is fused.

As illustrated in FIG. 6, due to the change of the refractive index distribution, the wave front of the propagating light that propagates from the optical fiber 2 to the light-radiating portion 5a' is gradually changed from a flat plane to a curved plane, and the mode of the propagating light is changed from a propagation mode to a radiation mode. In addition, due to the refractive index of the distal end portion 3a, the wave front is further changed to a curved plane, so that the propagating light is incident to the lens portion 3 to be emitted as an external illuminating light from the lens portion 3 to an outside of the light-illuminating probe 7. Since the diffusion of the propagating light in the inner portion of the light-radiating portion 5a' is further enlarged in comparison to the first embodiment, it is possible to further enlarge an illuminated spatial range of the external illuminating light in comparison to the first embodiment.

In addition, since the spread angle of the propagating light is increased before the propagating light approaches the lens portion 3, the illuminated spatial range of the external illuminating light can be enlarged, so that generation of back scattering light can be suppressed.

Third Embodiment

Figure 8:
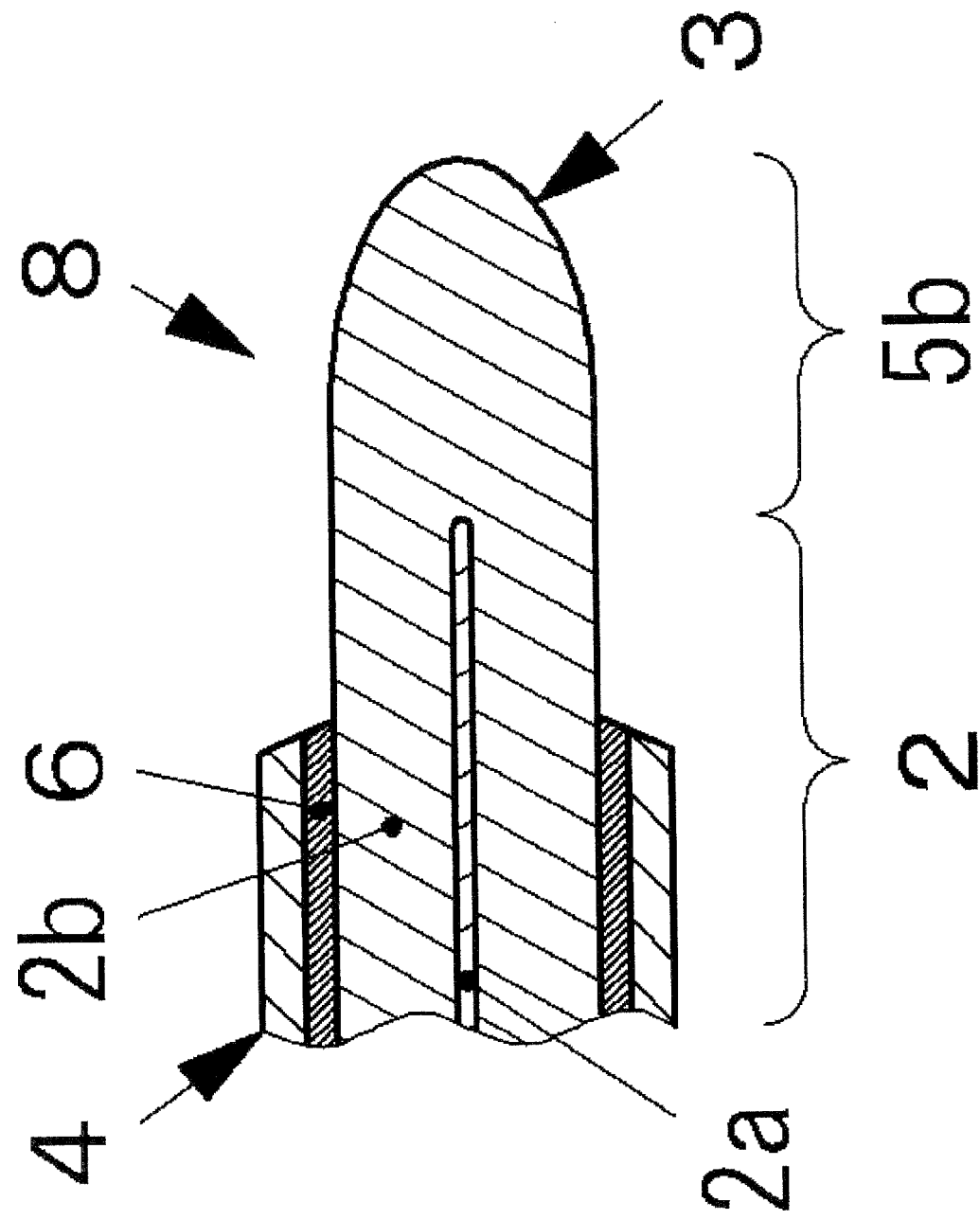
FIG. 8 is a cross-sectional view taken along line C-C of FIG. 7(a).
Figure 9:
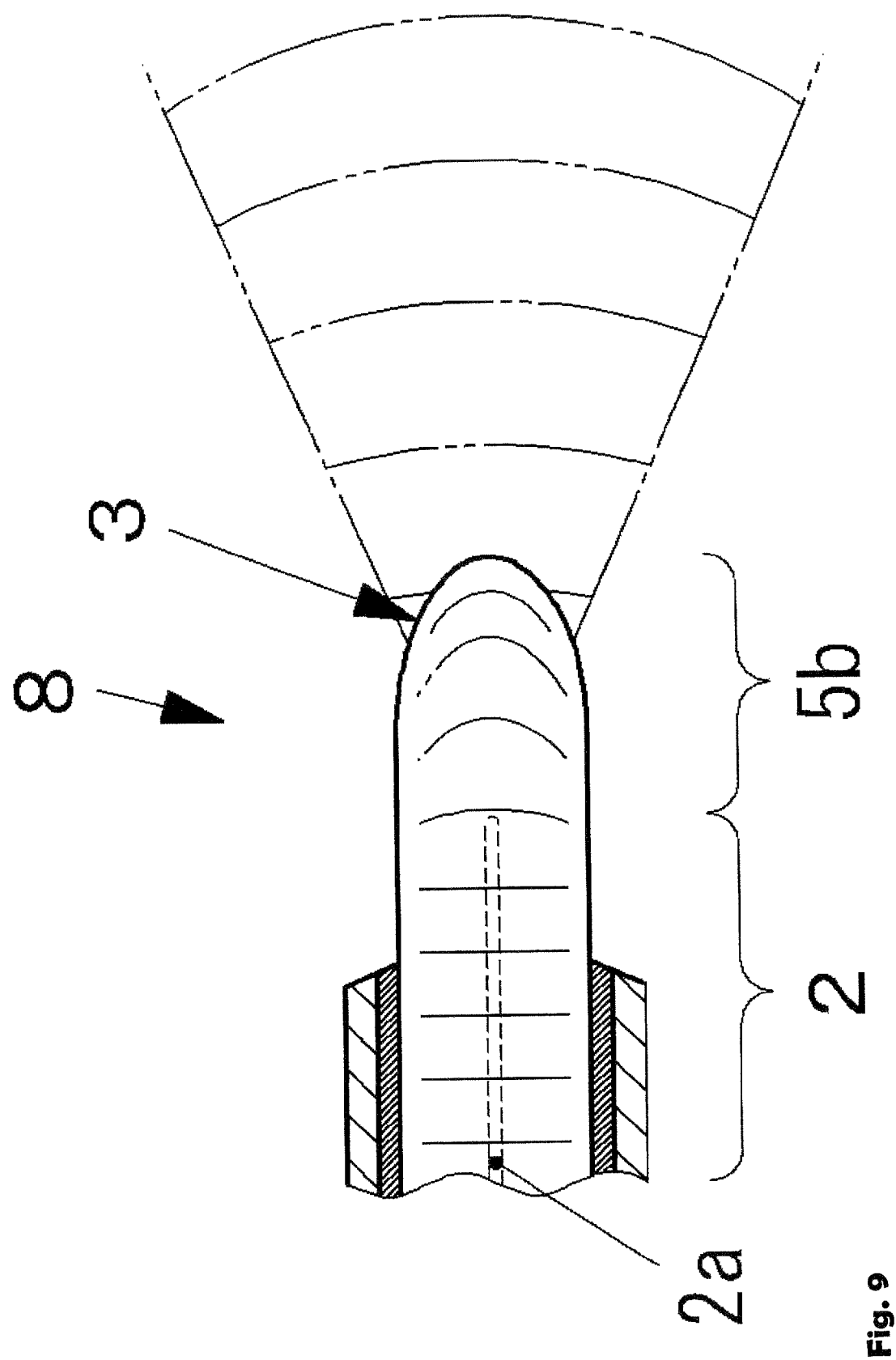
FIG. 9 is a schematic view illustrating propagation and radiation of light in the light-illuminating probe of FIG. 7.

FIGS. 7(*a*), (*b*) and (*c*) schematically illustrate a light-illuminating probe 8 given in a third embodiment of the present invention. FIG. 8 is a cross-sectional view taken along line C-C of FIG. 7(*a*). FIG. 9 illustrates propagation and radiation paths of light in the light-illuminating probe 8 given in the present embodiment. The same components as those of the aforementioned embodiments are denoted by the same reference numerals, and the description thereof is omitted and simplified.

The third embodiment is different from the aforementioned embodiments in that a region of the core 2a in the axial direction of the optical fiber 2 is terminated in an inner portion of the optical fiber 2, the light-radiating portion 5b is integrally formed in the extension of the optical fiber 2 in a direction matching with the axis of the optical fiber 2, and the refractive index distribution (spatial refractive index distribution) of the light-radiating portion 5b is formed to be uniform and equal to that of the clad 2b.

Figure 10:
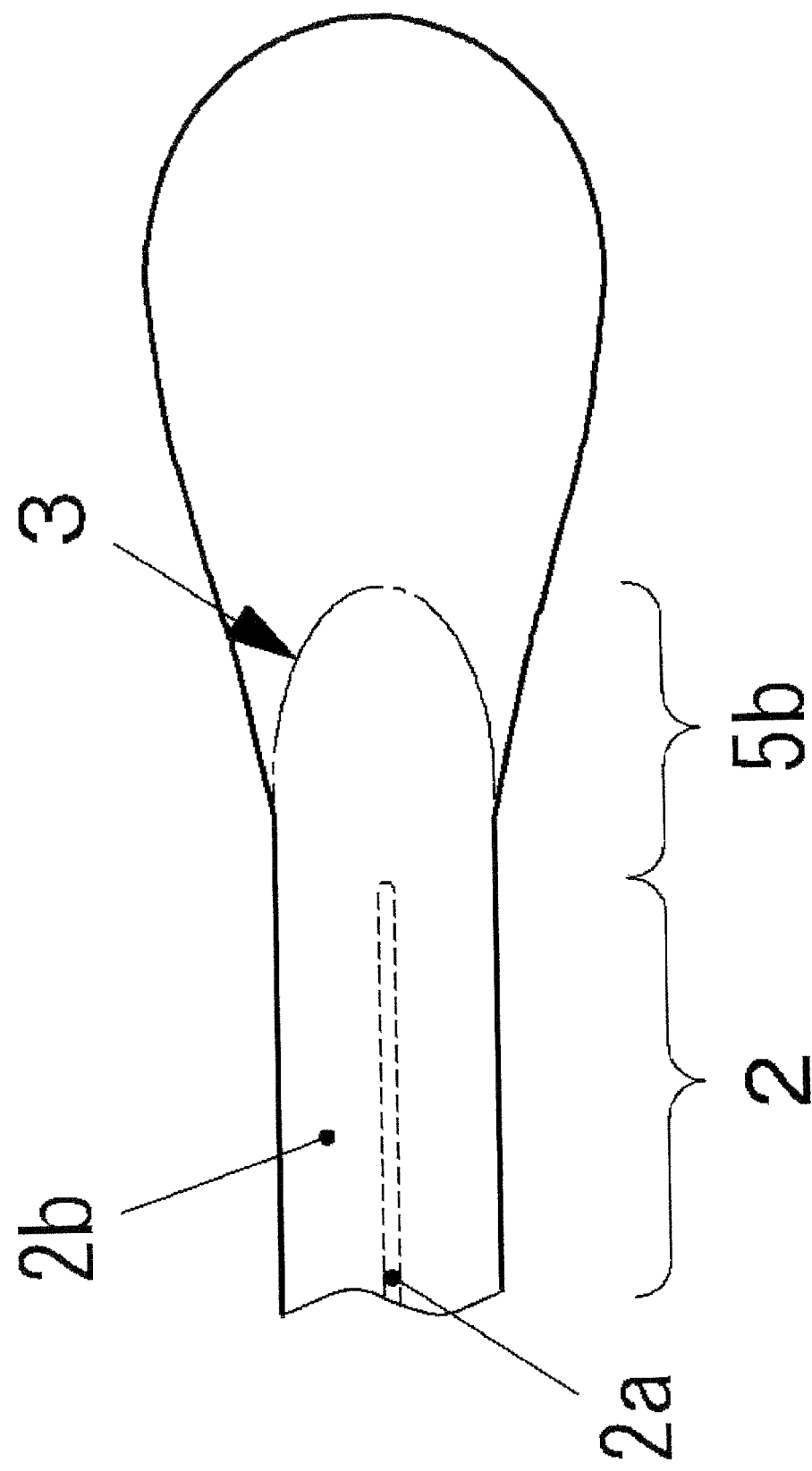
FIG. 10 is a view for explaining a method of manufacturing a refractive index structure of an optical fiber in the light-illuminating probe of FIG. 7.

Now, a method of manufacturing the optical fiber 2 is described with reference to FIG. 10. First of all, the extension of the optical fiber 2 is heated and fused to have a shape of droplet due to a surface tension thereof. Accordingly, the refractive index distribution of the extension of the optical fiber 2 is uniform and equal to that of the clad 2b. Next, the extension of the optical fiber that has a shape of droplet is subject to a grinding or polishing process to a portion indicated by a dotted dashed line of the figure, so that the lens portion 3 is formed and the light-radiating portion 5b is formed in the extension of the optical fiber 2.

As illustrated in FIG. 9, due to the termination of the region of the core 2a, the mode of the propagating light that propagates from the optical fiber 2 to the light-radiating portion 5b is changed from a propagation mode to a radiation mode, and the wave front thereof is gradually changed from a flat plane to a curved plane. The propagating light that is incident to the lens portions is emitted as an external radiating light from the lens portion 3 to an outside of the light-illuminating probe 8. Since the mode of the propagating light in an inner portion of the light-radiating portion 5b is changed to the radiation mode, a condensing function of the lens portion 3 is reduced, and the propagation of the light in the free space is maintained more effectively in the radiation mode. Therefore, in comparison to a conventional light-illuminating probe, it is possible to enlarge an illuminated spatial range of the external illuminating light.

In addition, since the spread angle of the propagating light is increased before the propagating light approaches the lens portion 3, the illuminated spatial range of the external illuminating light can be enlarged, so that generation of back scattering light can be suppressed.

Fourth Embodiment

Figure 11:
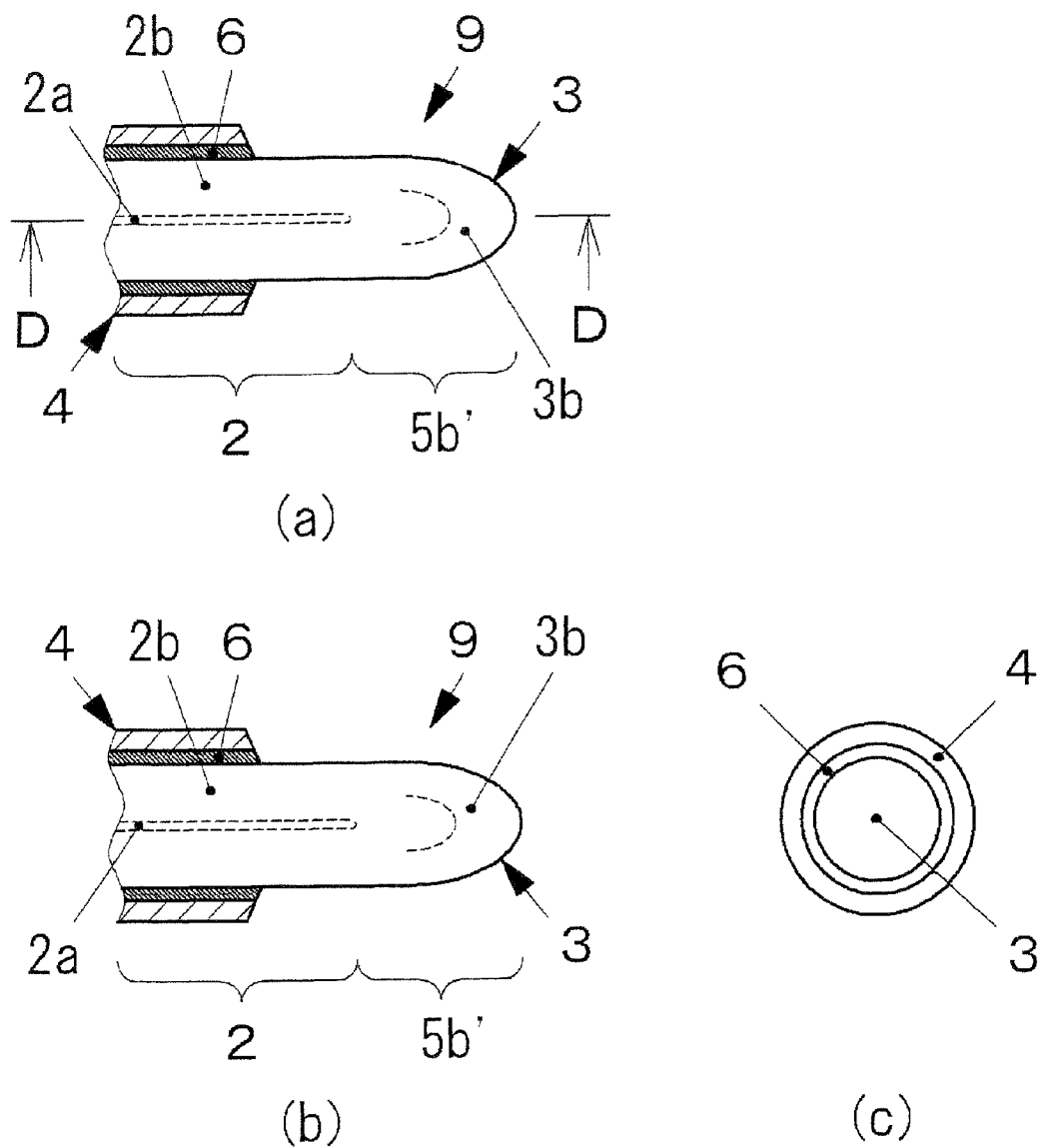
FIG. 11(a) is a schematic partially cross-sectional view illustrating a light-illuminating probe given in a fourth embodiment of the present invention.
FIG. 11(b) is a schematic partial left-side cross-sectional view illustrating the light-illuminating probe given in the fourth embodiment.
FIG. 11(c) is a schematic front view illustrating the light-illuminating probe given in the fourth embodiment.
Figure 12:
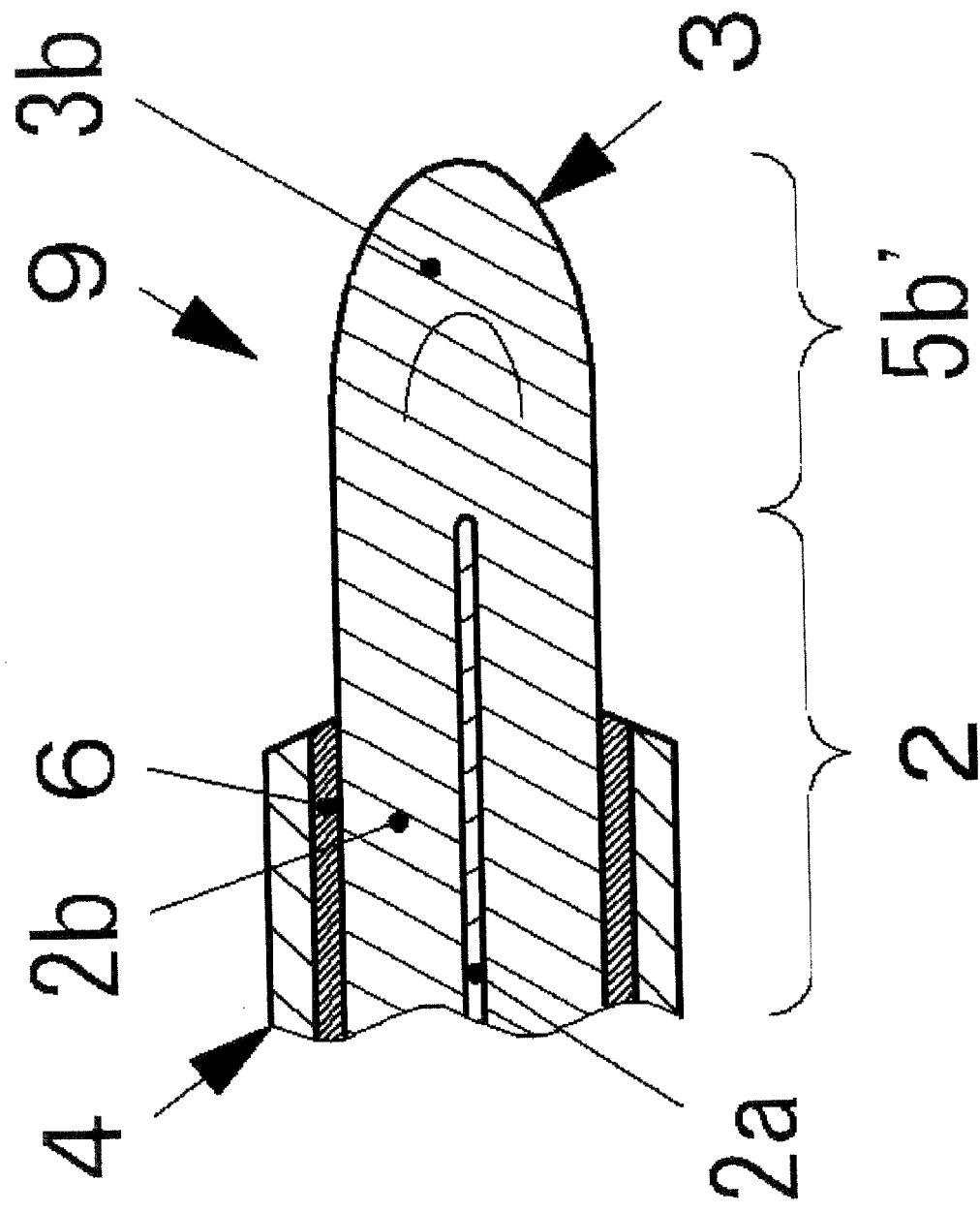
FIG. 12 is a cross-sectional view taken along line D-D of FIG. 11(a).
Figure 13:
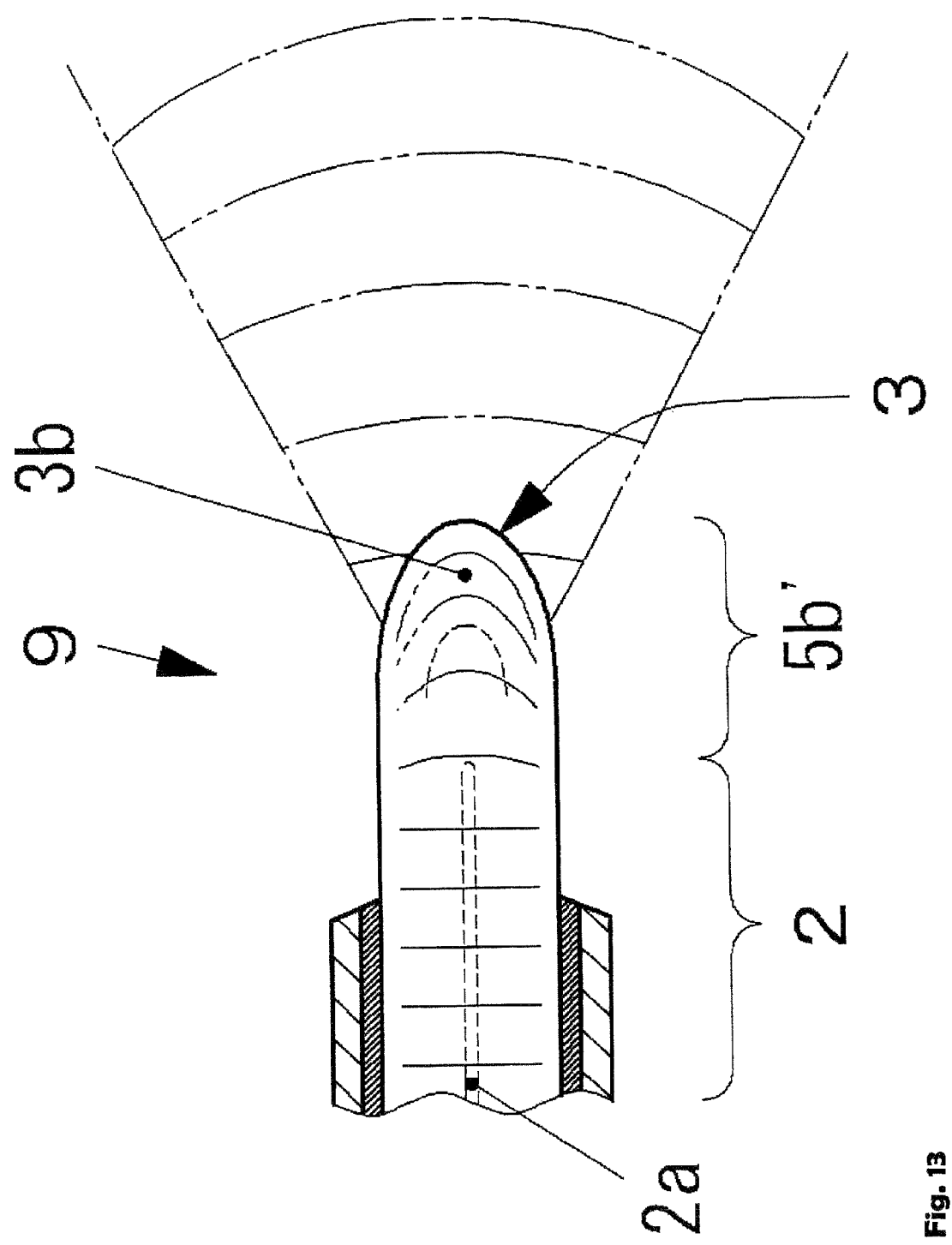
FIG. 13 is a schematic view illustrating propagation and radiation paths of light in the light-illuminating probe of FIG. 11

FIGS. 11(*a*), (*b*) and (*c*) schematically illustrate a light-illuminating probe 9 given in a fourth embodiment of the present invention. FIG. 12 is a cross-sectional view taken along line D-D of FIG. 11(*a*). FIG. 13 illustrates propagation and radiation paths of light in the light-illuminating probe 9 given in the present embodiment. The same components as those of the aforementioned embodiments are denoted by the same reference numerals, and the description thereof is omitted and simplified.

The fourth embodiment is different from the aforementioned embodiment, particularly, the third embodiment in that a refractive index distribution (spatial refractive index distribution) of a light-radiating portion 5*b*' is formed to be uniform and equal to that of the clad 2*b*, and a refractive index of a distal end portion 3*b* of a lens portion 3 in an inner portion of the light-radiating portion 5*b*' is set to be higher than that of the clad 2*b*.

Now, a method of manufacturing the light-radiating portion 5*b*' is described. Steps of forming the refractive index distribution of the light-radiating portion 5*b*' to be uniform and equal to that of the clad 2*b* illustrated in FIG. 12 are the same as those of the method given in the third embodiment, and thus, the description thereof is omitted. After the light-radiating portion 5*b*' of which refractive index distribution is uniform and equal to that of the clad 2*b* is formed, the distal end portion 3*b* is doped with a doping agent of Er, Nd, Ho, Tm, Pr, Sm, Dy, Yb, Ti, or the like, so that only the refractive index of the distal end portion 3*b* is higher than that of the clad 2*b*. As a doping method, after ion injection, the extension of the optical fiber may be subject to an annealing process, or the extension may be exposed to a vapor of a doping agent or a plasma ambience obtained from plasma of the vapor. Alternatively, the distal end portion 3*b* of the optical fiber 2 may be immersed into a low-temperature fusing quartz pool in which the doping agent is fused.

As illustrated in FIG. 13, due to the change of the refractive index distribution, the wave front of the propagating light that propagates from the optical fiber 2 to the light-radiating portion 5*b*' is gradually changed from a flat plane to a curved plane, and the mode of the propagating light is changed from a propagation mode to a radiation mode. In addition, due to the refractive index of the distal end portion 3*b*, the wave front is further changed to a curved plane, so that the propagating light is incident to the lens portion 3 to be emitted as an external radiating light from the lens portion 3 to an outside of the light-illuminating probe 9. Since the diffusion of the propagating light in the inner portion of the light-radiating portion 5*b*' is further enlarged in comparison to the third embodiment, it is possible to further enlarge an illuminated spatial range of the external illuminating light in comparison to the third embodiment.

In addition, since the spread angle of the propagating light is increased before the propagating light approaches the lens portion 3, the illuminated spatial range of the external illuminating light can be enlarged, so that generation of back scattering light can be suppressed.

Fifth Embodiment

Figure 14:
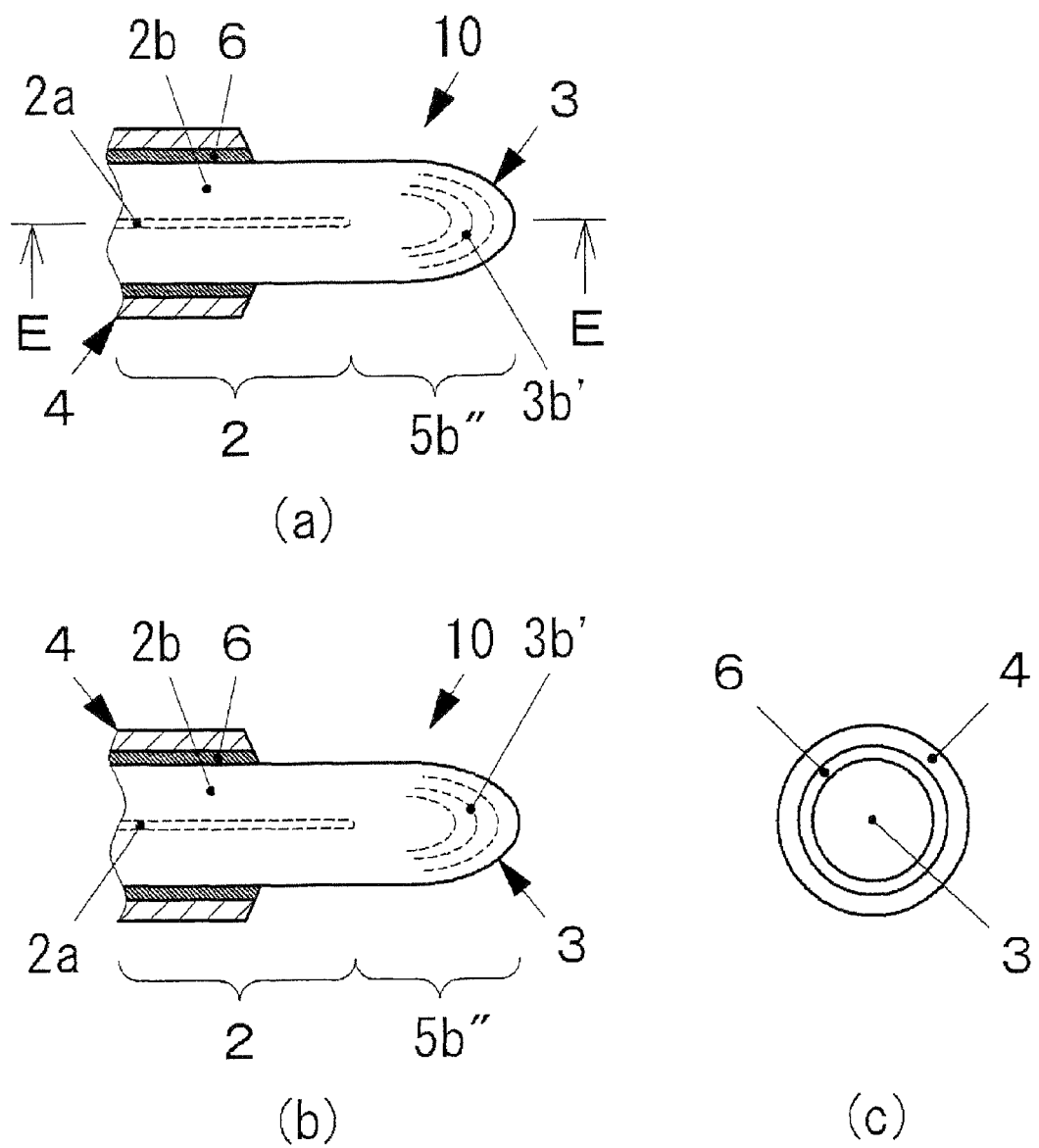
FIG. 14(a) is a schematic partially cross-sectional view illustrating a light-illuminating probe given in a fifth embodiment of the present invention.
FIG. 14(b) is a schematic partial left-side cross-sectional view illustrating the light-illuminating probe given in the fifth embodiment.
FIG. 14(c) is a schematic front view illustrating the light-illuminating probe given in the fifth embodiment.
Figure 15:
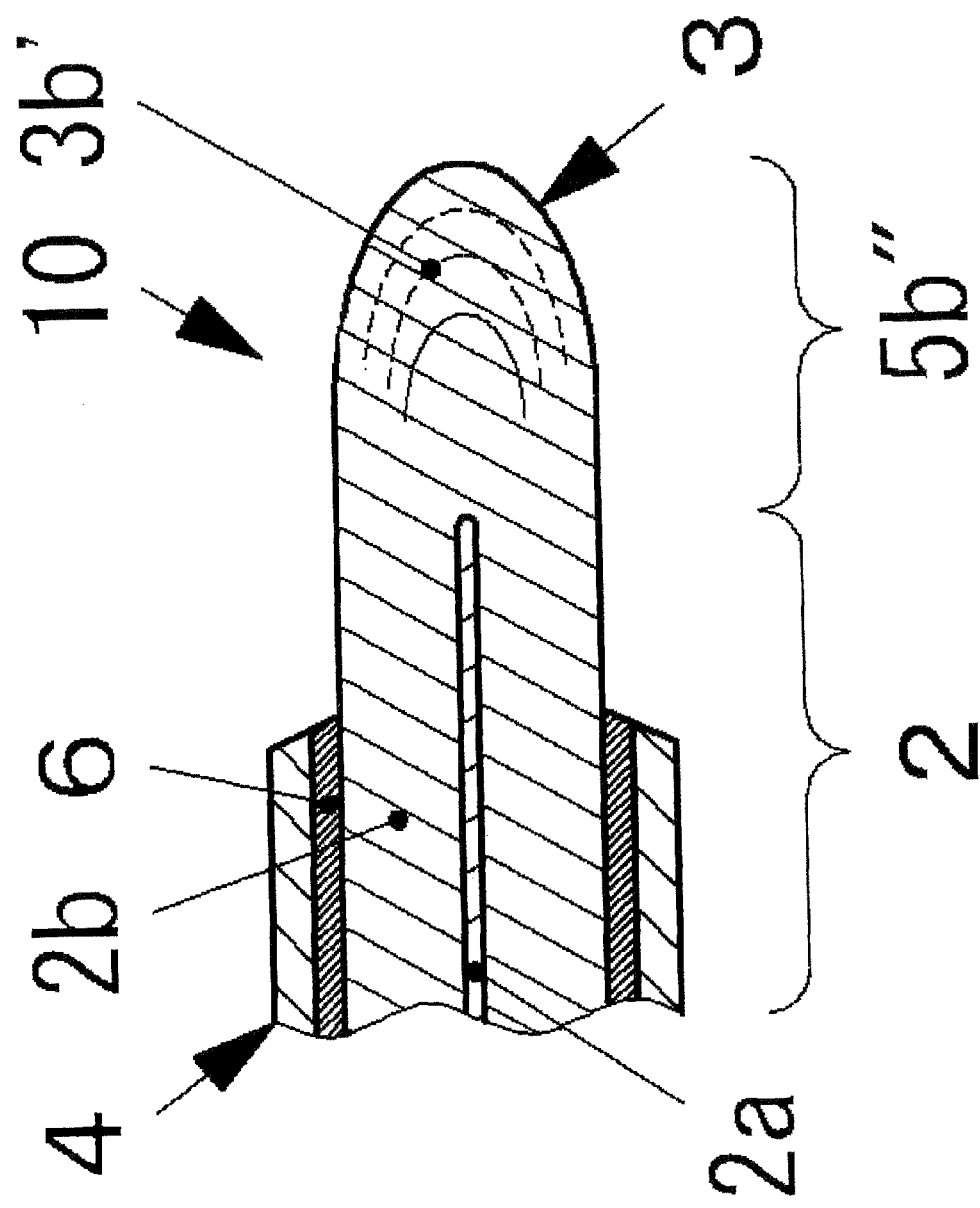
FIG. 15 is a cross-sectional view taken along line E-E of FIG. 14(a).
Figure 16:
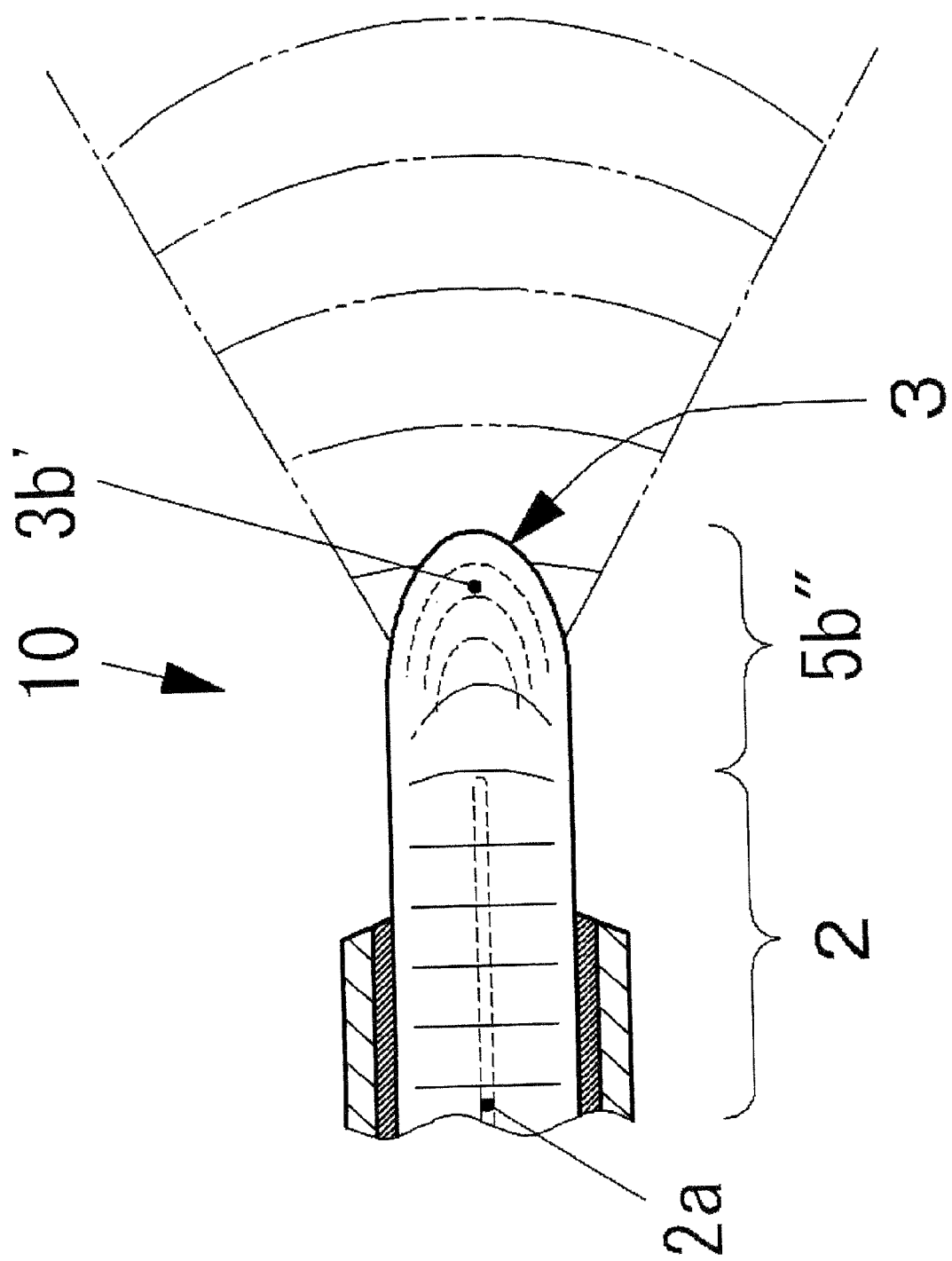
FIG. 16 is a schematic view illustrating propagation and radiation of light in the light-illuminating probe of FIG. 14

FIGS. 14(*a*), (*b*) and (*c*) schematically illustrate a light-illuminating probe 10 given in a fifth embodiment of the present invention. FIG. 15 is a cross-sectional view taken along line E-E of FIG. 14(*a*). FIG. 16 illustrates propagation and radiation paths of light in the light-illuminating probe 10 given in the present embodiment. The same components as those of the aforementioned embodiments are denoted by the same reference numerals, and the description thereof is omitted and simplified.

The fifth embodiment is different from the aforementioned embodiment, particularly, the fourth embodiment in that a refractive index distribution (spatial refractive index distribution) of a light-radiating portion 5*b*" is formed to be uniform and equal to that of the clad 2*b*, a refractive index of a distal end portion 3*b*' of a lens portion of the light-radiating portion 5*b*" is set to be higher than that of the clad 2*b*, and the refractive index is set to be gradually increased in a direction approaching a surface (that is, the lens portion 3) of the distal end portion 3*b*'.

Now, a method of manufacturing the light-radiating portion 5*b*" is described. Steps of forming the refractive index distribution of the light-radiating portion 5*b*" to be uniform and equal to that of the clad 2*b* illustrated in FIG. 15 are the same as those of the method given in the third embodiment, and thus, the description thereof is omitted. After the light-radiating portion 5*b*" of which refractive index distribution is uniform and equal to that of the clad 2*b* is formed, the distal end portion 3*b*' is doped with a doping agent of Er, Nd, Ho, Tm, Pr, Sm, Dy, Yb, Ti, or the like, and at the same time, a concentration thereof is adjusted. Accordingly, only the refractive index of the distal end portion 3*b*' is higher than that of the clad 2*b*, and the refractive index is increased stepwise in a direction approaching a surface of the distal end portion 3*b*'. As a doping method, after ion injection, the extension of the optical fiber may be subject to an annealing process, or the extension may be exposed to a vapor of a doping agent or a plasma ambience obtained from plasma of the vapor. Alternatively, the distal end portion 3*b*' may be immersed into a low-temperature fusing quartz pool in which the doping agent is fused.

As illustrated in FIG. 16, due to the change of the refractive index distribution, the wave front of the propagating light that propagates from the optical fiber 2 to the light-radiating portion 5*b*" is gradually changed from a flat plane to a curved plane, and the mode of the propagating light is changed from a propagation mode to a radiation mode. In addition, due to the refractive index of the distal end portion 3*b*', the wave front is further changed to a curved plane. In the fifth embodiment, since the refractive index is gradually increased in the direction approaching the surface of the distal end portion 3*b*', the wave front of the external illuminating light emitted from the lens portion 3 is changed to a curved plane, so that it is possible to further enlarge an illuminated spatial range of the external illuminating light in comparison to the fourth embodiment.

In addition, since the spread angle of the propagating light is increased before the propagating light approaches the lens portion 3, the illuminated spatial range of the external illuminating light can be enlarged, so that generation of back scattering light can be suppressed.

Sixth Embodiment

Figure 18:
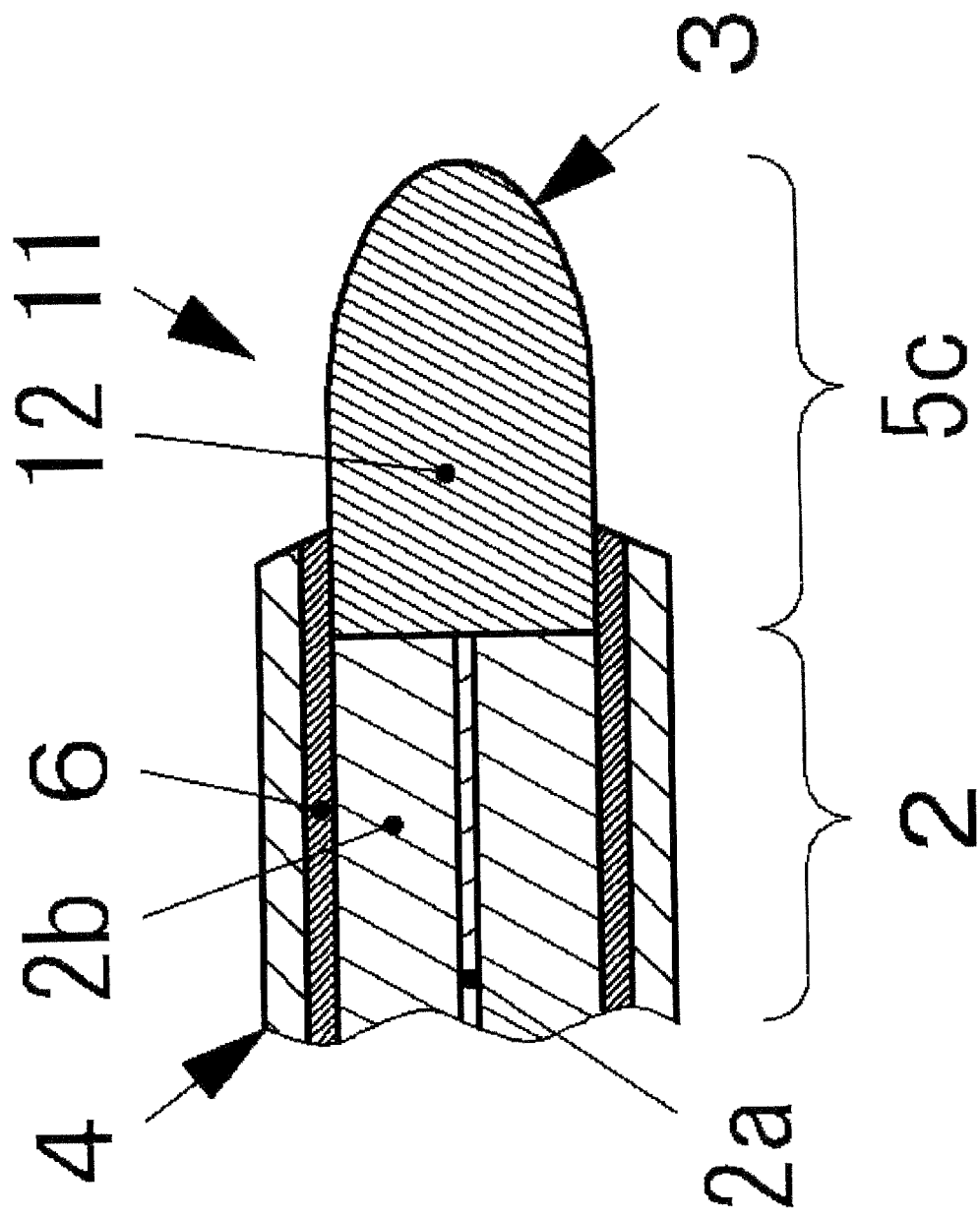
FIG. 18 is a cross-sectional view taken along line F-F of FIG. 17(a).
Figure 19:
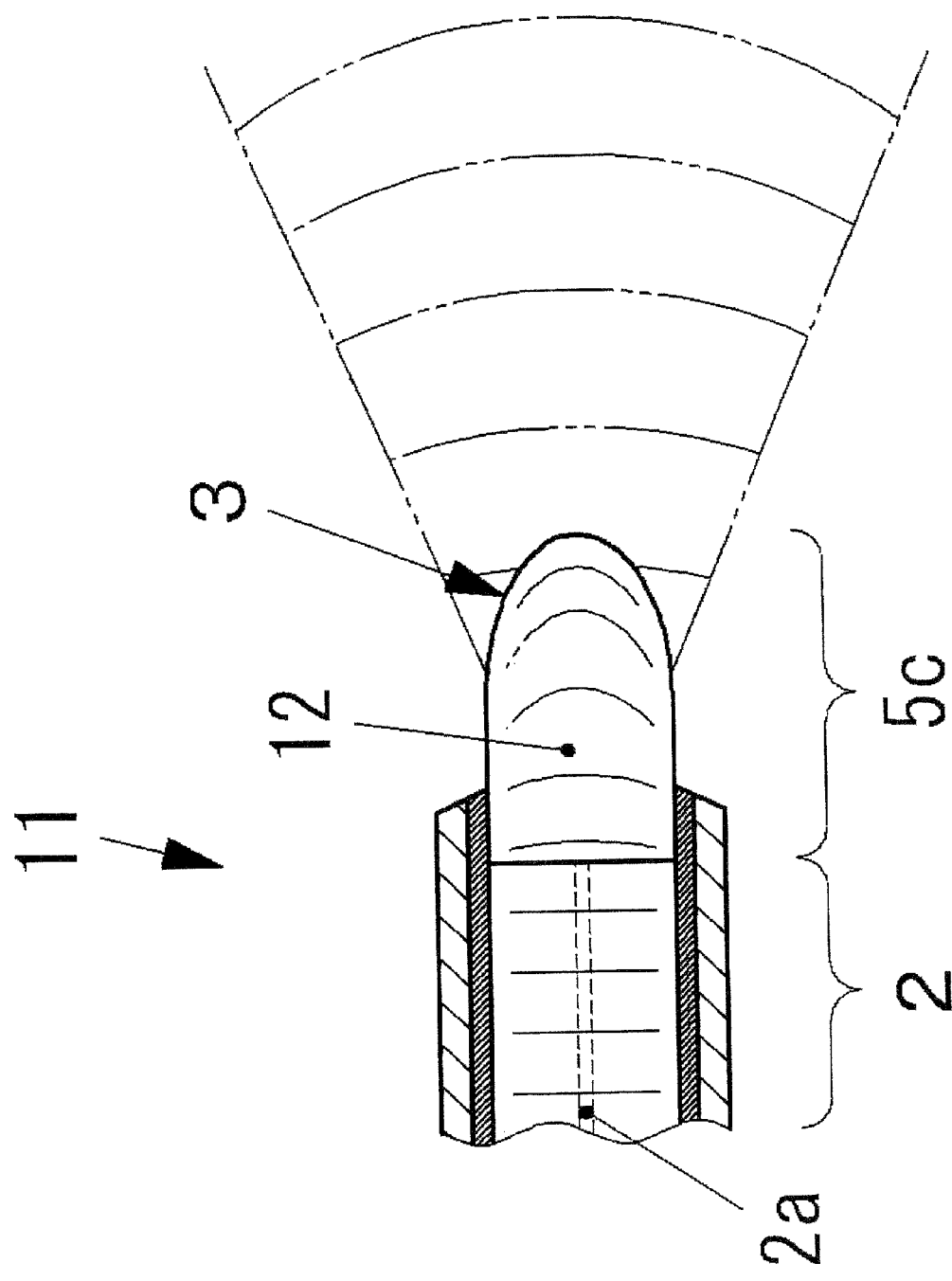
FIG. 19 is a schematic view illustrating propagation and radiation of light in the light-illuminating probe of FIG. 17.

FIGS. 17(*a*), (*b*) and (*c*) schematically illustrate a light-illuminating probe 11 given in a sixth embodiment of the present invention. FIG. 18 is a cross-sectional view taken along line F-F of FIG. 17(*a*). FIG. 19 illustrates propagation and radiation paths of light in the light-illuminating probe 11 given in the present embodiment. The same components as those of the aforementioned embodiments are denoted by the same reference numerals, and the description thereof is omitted and simplified.

The sixth embodiment is different from the aforementioned embodiments in that a transparent optical member 12 having a spatial refractive index distribution in which a refractive index thereof is different from that of the core 2*a* and/or the clad 2*b* is provided as a light-radiating portion 5*c* to an extension of an optical fiber 2 of the light-illuminating probe 11. The refractive index of the optical member 12 is set to be uniform. The optical member 12 is formed to have a circular shape in which an outer diameter thereof is equal to that of the clad 2*b* of the optical fiber 2, and the extension thereof is provided with a lens portion 3. Similarly to the optical fiber 2, an outer circumferential surface of the optical member 12 is inserted into a cannula 4 and hermetically sealed with a hermetic seal 6.

As illustrated in FIG. 19, due to the change of the refractive index distribution, the mode of the propagating light that propagates from the optical fiber 2 to the light-radiating portion 5c is changed from a propagation mode to a radiation mode at the time of incidence to the optical member 12, and the wave front thereof is changed from a flat plane to a curved plane, so that the propagating light is diffused in the inner portion of the optical member 12. The propagating light is incident to the lens portion 3 to be emitted as an external radiating light from the lens portion 3 to an outside of the light-illuminating probe 11.

Since the mode of the propagating light in the inner portion of the optical member 12 is changed to the radiation mode, a condensing function of the lens portion 3 is reduced, and the propagation of the light in the free space is maintained more effectively in the radiation mode. Therefore, in comparison to a conventional light-illuminating probe 11, it is possible to enlarge an illuminated spatial range of the external illuminating light.

The optical member 12 is preferably made of a material having hardness (for example, Mohs hardness) higher than that of the optical fiber 2 and invulnerable to abrasion. Since the optical member 12 that is harder than the optical fiber 2 is provided next to an end of the optical fiber 2, a material having a suitable hardness for fundus surgery which is a main use of the light-illuminating probe 11 can be used.

In addition, since the propagating light is radiated in the inner portion of the optical member 12 before the propagating light approaches the lens portion 3 which is the light-radiating portion, the illuminated spatial range of the external illuminating light can be enlarged, so that generation of back scattering light can be suppressed.

Seventh Embodiment

Figure 21:
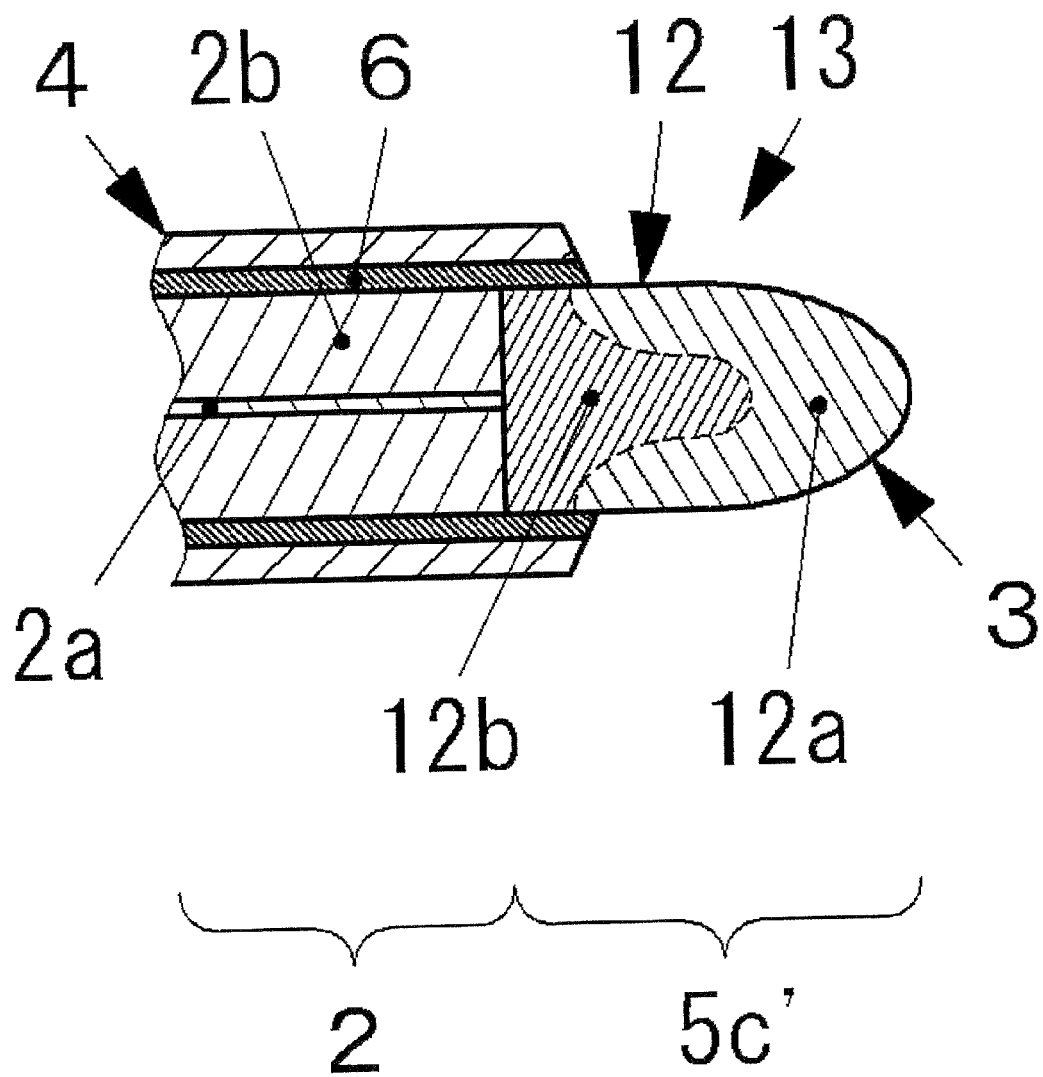
FIG. 21 is a cross-sectional view taken along line G-G of FIG. 20(a).
Figure 22:
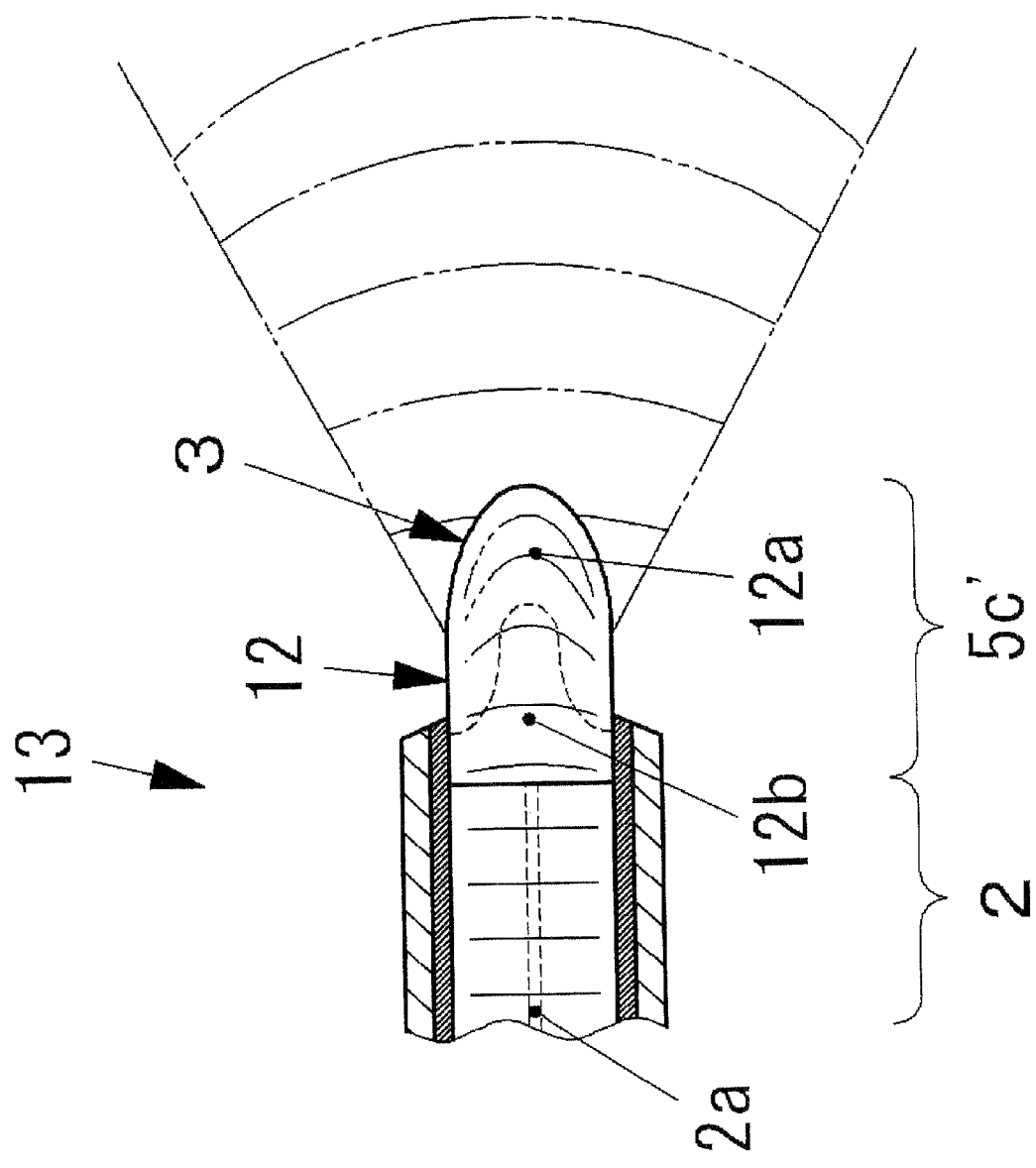
FIG. 22 is a schematic view illustrating propagation and radiation of light in the light-illuminating probe of FIG. 20.

FIGS. 20(a), (b) and (c) schematically illustrate a light-illuminating probe 13 given in a seventh embodiment of the present invention. FIG. 21 is a cross-sectional view taken along line G-G of FIG. 20(a). FIG. 22 illustrates propagation and radiation paths of light in the light-illuminating probe 13 given in the present embodiment. The same components as those of the aforementioned embodiments are denoted by the same reference numerals, and the description thereof is omitted and simplified.

The seventh embodiment is different from the aforementioned embodiments, particularly, the sixth embodiment in that an optical member 12 is provided as a light-radiating portion 5c' to an extension of an optical fiber 2 of the light-illuminating probe 13, and a spatial refractive index distribution in which a refractive index of an distal portion 12a of the optical member 12 is different from that of an adjacent portion 12b to the optical fiber 2 is formed. Similarly to the sixth embodiment, the optical member 12 is provided as the extension of the optical fiber 2, and the distal portion 12a (that is, the lens portion 3) of the optical member 12 is doped with a doping agent of MgO, Er, Nd, Ho, Tm, Pr, Sm, Dy, Yb, Ti, or the like, so that the refractive index of the distal portion 12a is set to be higher than that of the adjacent portion 12b to the optical fiber 2. After the doping, the distal portion 12a is heated to emit the doping agent, so that the refractive index of the adjacent portion 12b to the optical fiber 2 is set to be higher than that of the distal portion 12a. Accordingly, the refractive index of the inner portion of the optical member 12 can be changed. As a doping method, after ion injection, the extension of the optical fiber may be subject to an annealing process, or the extension may be exposed to a vapor of a doping agent or a plasma ambience obtained from plasma of the vapor. Alternatively, the distal portion 12a of the optical fiber 2 may be immersed into a low-temperature fusing quartz pool in which the doping agent is fused.

As illustrated in FIG. 22, due to the change of the refractive indexes of the optical fiber 2 and the light-radiating portion 5c', the mode of the propagating light that propagates from the optical fiber 2 to the light-radiating portion 5c' is changed from a propagation mode to a radiation mode at the time of incidence to the optical member 12, and the wave front thereof is changed from a flat plane to a curved plane, so that the propagating light is diffused in the inner portion of the optical member 12.

In addition, due to the change of the refractive index of the inner portion of the optical member 12, the wave front is further changed to a curved plane as the light propagates to the lens portion 3, and in this state, the propagating light is incident to the lens portion 3 to be emitted as an external radiating light from the lens portion 3 to an outside of the light-illuminating probe 13. Since the diffusion of the propagating light in the inner portion of the light-radiating portion 5c' is further enlarged in comparison to the sixth embodiment, it is possible to further enlarge an illuminated spatial range of the external illuminating light in comparison to the sixth embodiment.

Similarly to the sixth embodiment, the optical member 12 is preferably made of a material having hardness (for example, Mohs hardness) higher than that of the optical fiber 2 and invulnerable to abrasion.

In addition, since the propagating light is radiated in the inner portion of the optical member 12 before the propagating light approaches the lens portion 3 which is the light-radiating portion, the illuminated spatial range of the external illuminating light can be enlarged, so that generation of back scattering light can be suppressed.

Eighth Embodiment

Figure 24:
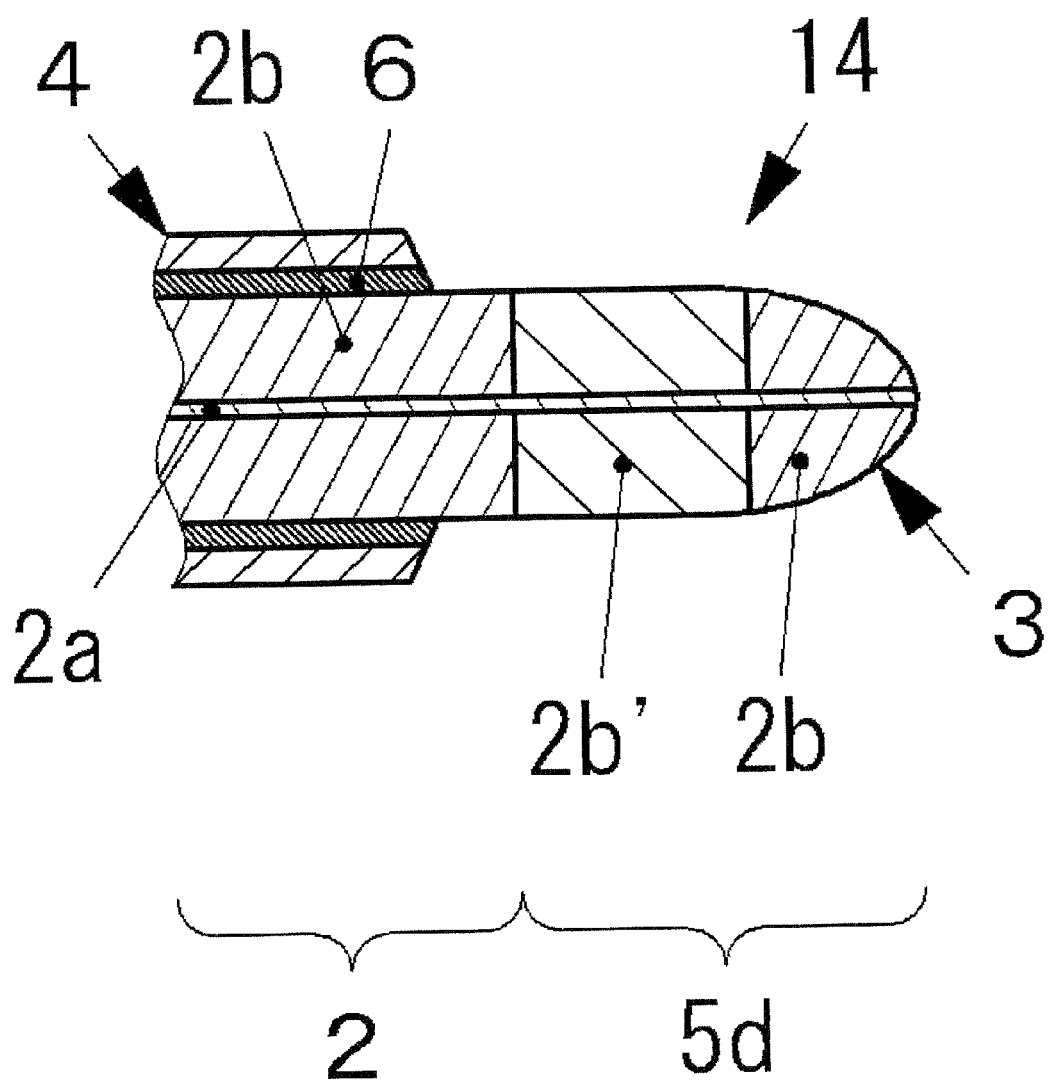
FIG. 24 is a cross-sectional view taken along line H-H of FIG. 23(a).
Figure 25:
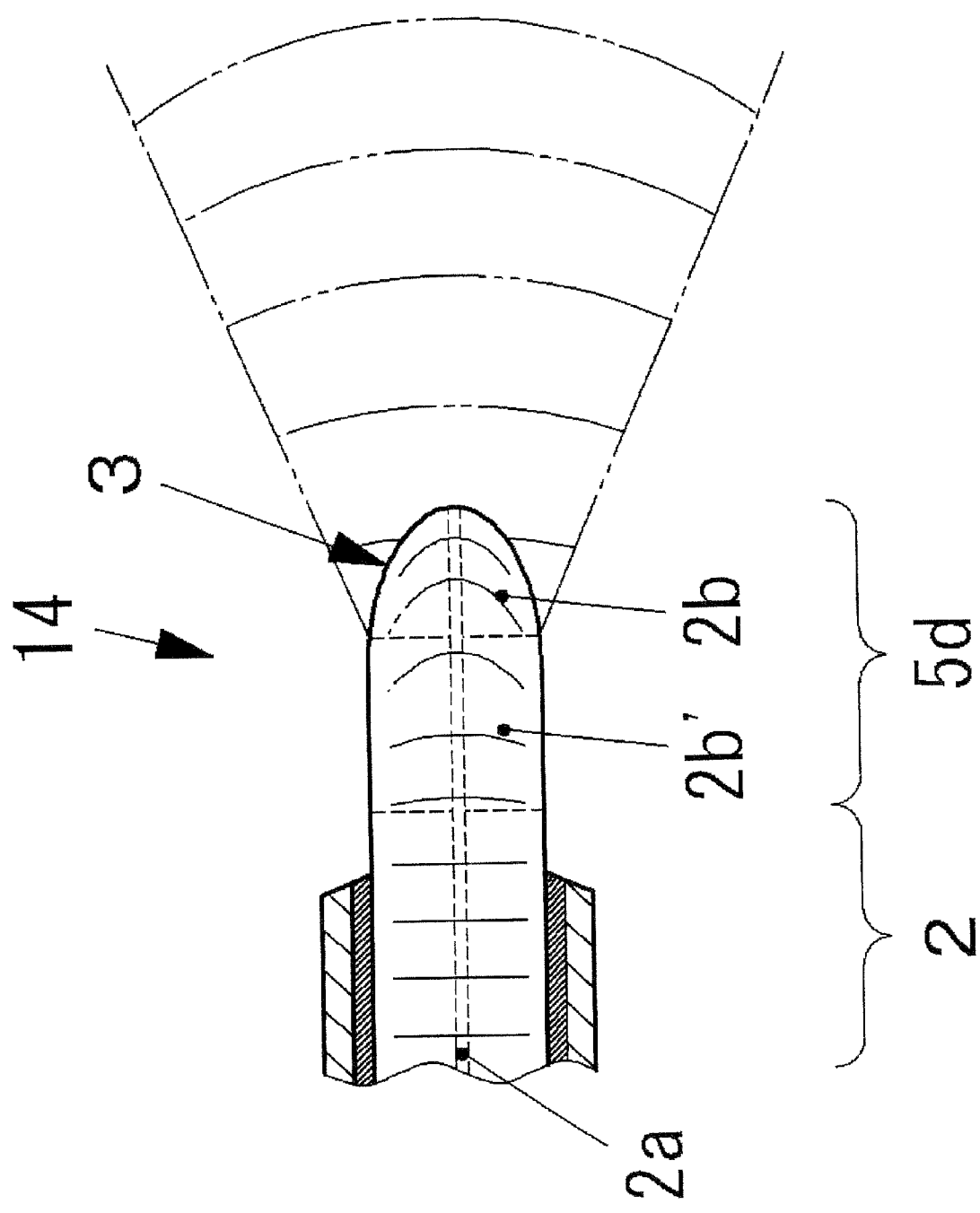
FIG. 25 is a schematic view illustrating propagation and radiation of light in the light-illuminating probe of FIG. 23.

FIGS. 23(a), (b) and (c) schematically illustrate a light-illuminating probe 14 given in an eighth embodiment of the present invention. FIG. 24 is a cross-sectional view taken along line H-H of FIG. 23(a). FIG. 25 illustrates propagation and radiation paths of light in the light-illuminating probe 14 given in the present embodiment. The same components as those of the aforementioned embodiments are denoted by the same reference numerals, and the description thereof is omitted and simplified.

The eighth embodiment is different from the aforementioned embodiments in that a light-radiating portion 5d having a spatial refractive index distribution in which a refractive index of a portion of a clad 2b is set to be higher than that of the aforementioned core 2a is formed, and a light-illuminating probe 14 includes the light-radiating portion 5d that is disposed to an extension of an optical fiber 2. As a method of increasing the refractive index of the portion of the clad 2b', the portion of the clad 2b' is doped with a fused benzoic acid or MgO, and proton exchange is performed to increase the refractive index. As an alternative method, a doping agent of Er, Nd, Ho, Tm, Pr, Sm, Dy, Yb, Ti, or the like is used to increase the refractive index. As a doping method, after ion injection, the extension of the optical fiber may be subject to an annealing process, or the extension may be exposed to a vapor of a doping agent or a plasma ambience obtained from plasma of the vapor. Alternatively, the distal end portion of the optical fiber 2 may be immersed into a low-temperature fusing quartz pool in which the doping agent is fused.

After a clad 2b' is formed, an extension of the optical fiber 2 is cut with a predetermined size. Next, the cut portion from the clad 1b' is grinded or polished in a radial shape so that the spread angle of the radiating light from the cut portion of the extension is within a predetermined range. Accordingly, the rounding process is performed on the distal end portion of the light-radiating portion 5d, so that the lens portion 3 is formed. Therefore, a portion from the clad 2b' of which refractive index is changed to the lens portion 3 becomes the light-radiating portion 5d, and the other portion of the clad b and the core 2a integrally constitutes the optical fiber 2. Since the cut portion is grinded or polished in the radial shape so that the spread angle of the radiating light is within a predetermined range, it is possible to eliminate an irregularity of the external illuminating light.

As illustrated in FIG. 25, due to the change of the refractive index of the clad 2b', a total reflection of the propagating light that propagates from the optical fiber 2 to the clad 2b' disappears, the mode thereof is changed from a propagation mode to a radiation mode, the wave front thereof is changed from a flat plane to a curved plane, and the propagating light is diffused in the inner portion of the light-radiating portion 5d. As the light propagates to the lens portion 3, the refractive index of the clad is changed to the original refractive index (refractive index of the clad 2b). However, since the light is diffused at the time of propagating to the clad 2b', the function of changing the propagation mode in the clad 2b of the light-radiating portion 5d has no influence to the light. Although the propagating light that is incident to the lens portion 3 is emitted as an external radiating light to an outside of the light-illuminating probe 14, since the mode of the light in the inner portion of the light-radiating portion 5d is changed to the radiation mode, a condensing function of the lens portion 3 is reduced, and the propagation of the light in the free space is maintained more effectively in the radiation mode. Therefore, in comparison to a conventional light-illuminating probe, it is possible to enlarge an illuminated spatial range of the external illuminating light.

In addition, since the spread angle of the propagating light is increased before the propagating light approaches the lens portion 3, the illuminated spatial range of the external illuminating light can be enlarged, so that generation of back scattering light can be suppressed.

Ninth Embodiment

Figure 27:
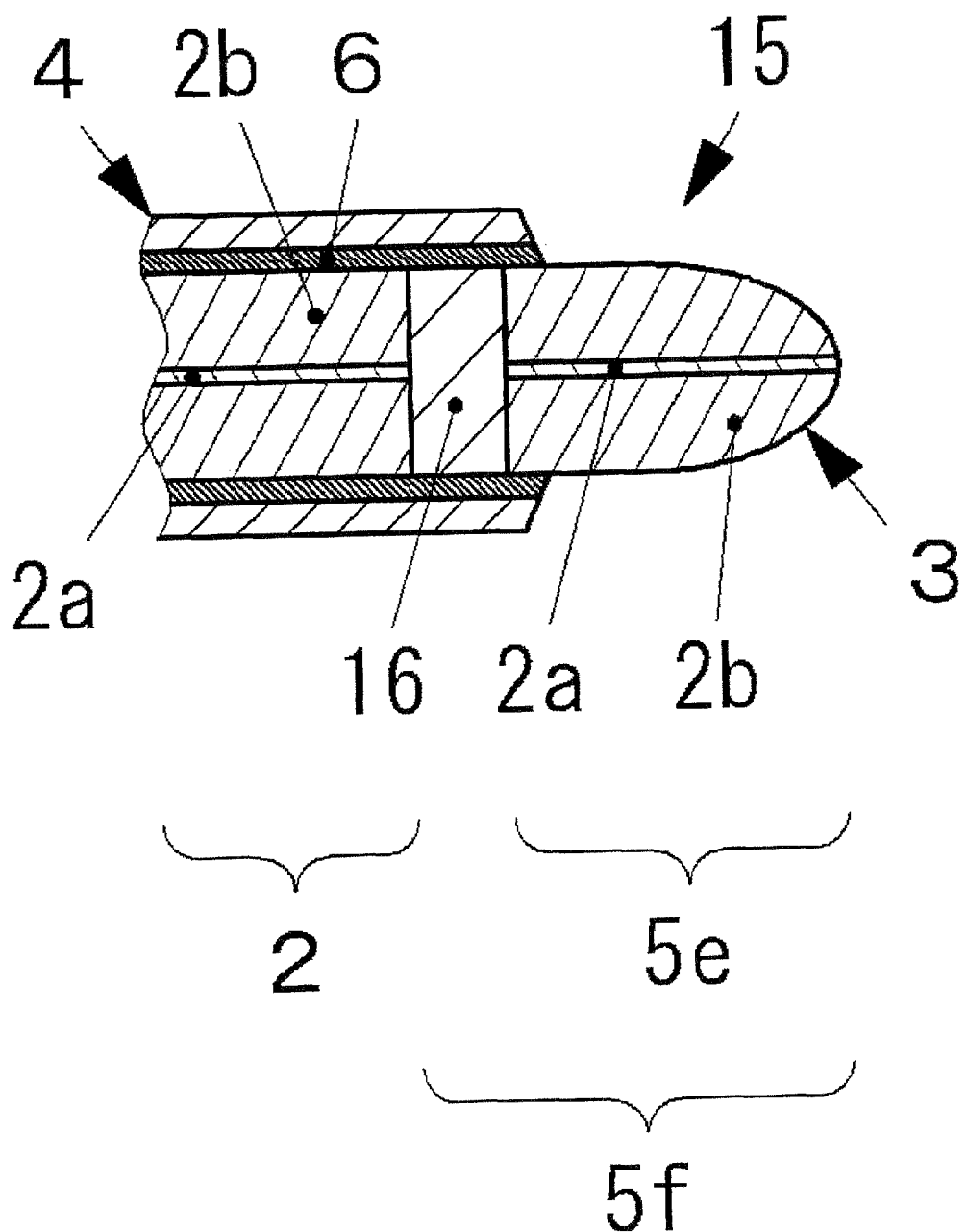
FIG. 27 is a cross-sectional view taken along line I-I of FIG. 26(a).
Figure 28:
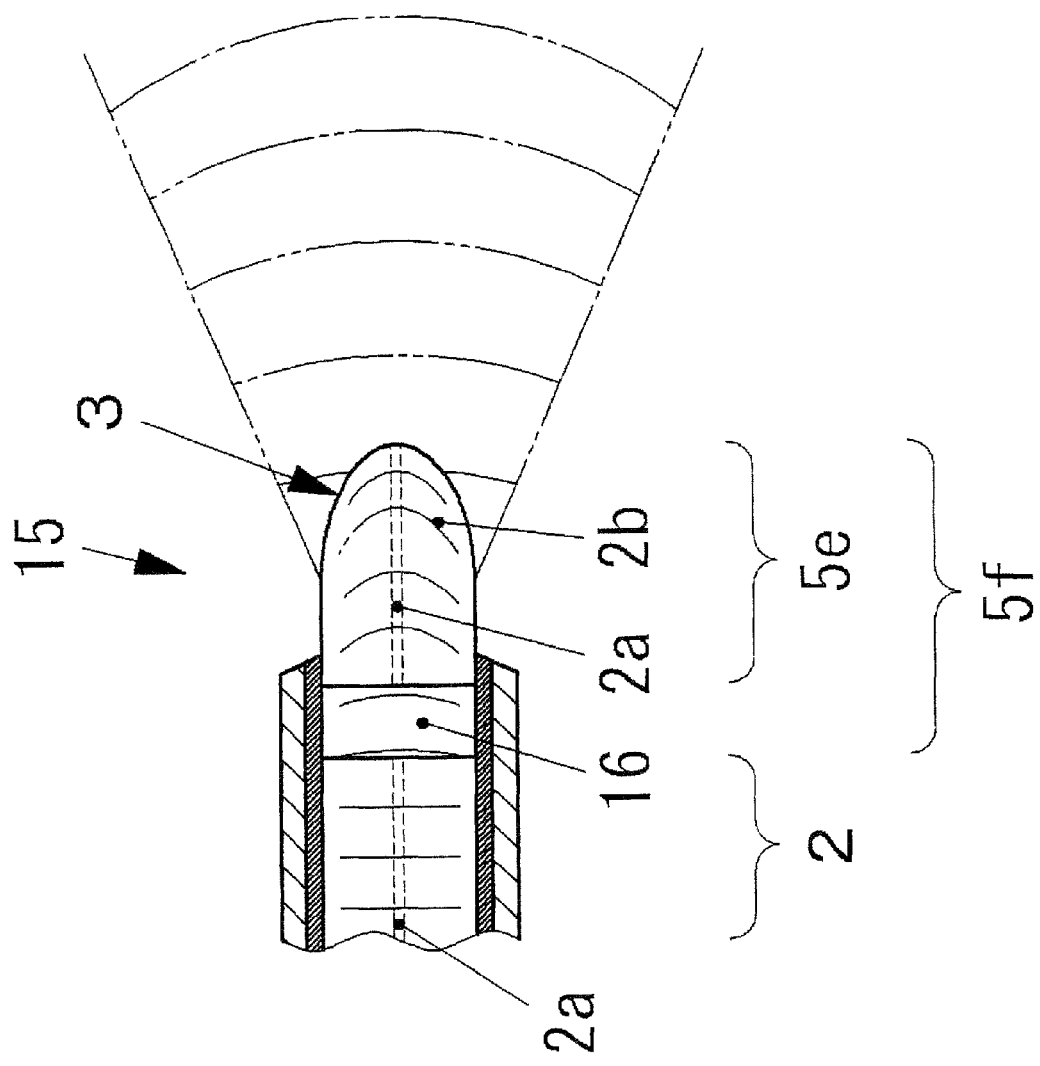
FIG. 28 is a schematic view illustrating propagation and radiation of light in the light-illuminating probe of FIG. 26.

FIGS. 26(a), (b) and (c) schematically illustrate a light-illuminating probe 15 given in a ninth embodiment of the present invention. FIG. 27 is a cross-sectional view taken along line I-I of FIG. 26(a). FIG. 28 illustrates propagation and radiation paths of light in the light-Illuminating probe 15 given in the present embodiment. The same components as those of the aforementioned embodiments are denoted by the same reference numerals, and the description thereof is omitted and simplified.

The ninth embodiment is different from the aforementioned embodiments in that an optical fiber 2 constructed with a core 2a and a clad 2b which has a refractive index lower than that of the core 2a and surrounds the core 2a is cut, and a transmissive diffusing plate 16 is inserted between the optical fiber 2 and a distal end portion 5e. Due to the insertion of the transmissive diffusing plate 16, the light-radiating portion 5f is constructed with the transmissive diffusing plate 16 and the distal end portion 5e which is cut from the optical fiber 2 and provided with the lens portion 3. The distal end portion 5e has a refractive index distribution equal to that of the optical fiber 2, and a distal end portion 5e thereof is provided with the lens portion 3. The light-illuminating probe 15 has a spatial refractive index distribution in which the optical fiber 2 and the light-radiating portion 5f are distinguished from each other.

A milk-white glass plate is very suitably used as a material of the transmissive diffusing plate 16. The transmissive diffusing plate 16 is formed in an outer shape equal to that of the optical fiber 2 with an outer diameter equal to that of the c ad 2b. Due to the insertion of the transmissive diffusing plate 16 between the optical fiber 2 and the distal end portion 5e, the light-illuminating probe 15 has a construction that a diffusion region is provided between light-guiding lines.

As illustrated in FIG. 28, the propagating light that propagates from the optical fiber 2 to the light-radiating portion 5f is incident to the transmissive diffusing plate 16 to be diffused due to the function of the transmissive diffusing plate 16, the mode thereof is changed from a propagation mode to a radiation mode, and the wave front thereof is gradually changed from a flat plane to a curved plane. The propagating light that is incident to the lens portion 3 is emitted as an external radiating light from the lens portion 3 to an outside of the light-illuminating probe 15. Since the mode of the propagating light in an inner portion of the light-radiating portion 5f is changed to the radiation mode, a condensing function of the lens portion 3 is reduced, and the propagation of the light in the free space is maintained more effectively in the radiation mode. Therefore, in comparison to a conventional light-illuminating probe, it is possible to enlarge an illuminated spatial range of the external illuminating light.

In addition, since the spread angle of the propagating light is increased due to the diffusion in the transmissive diffusing plate 16 before the propagating light approaches the lens portion 3 which is the light-radiating portion, the illuminated spatial range of the external illuminating light can be enlarged, so that generation of back scattering light can be suppressed.

Tenth Embodiment

Figure 30:
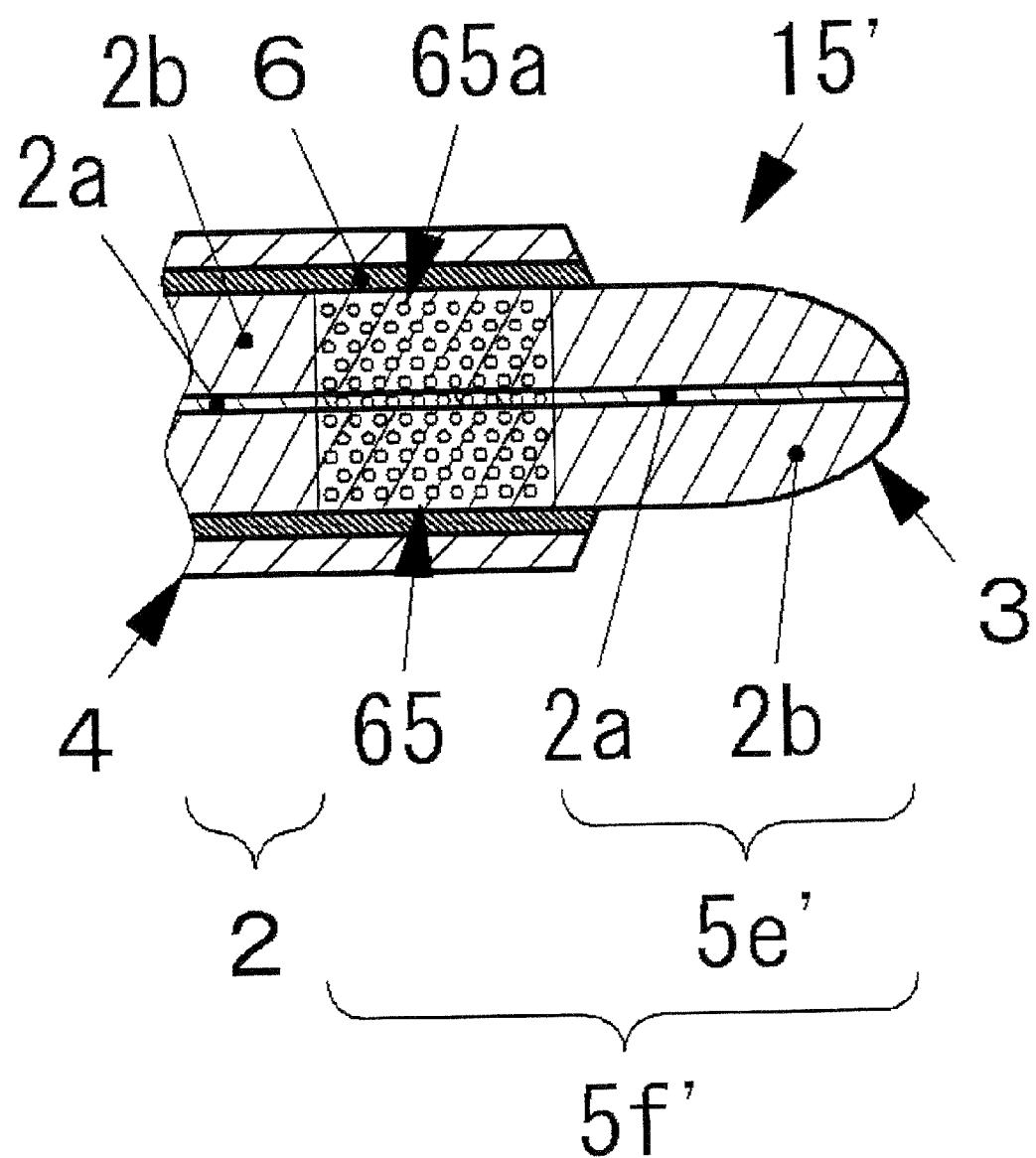
FIG. 30 is a cross-sectional view taken along line N-N of FIG. 29(a).
Figure 31:
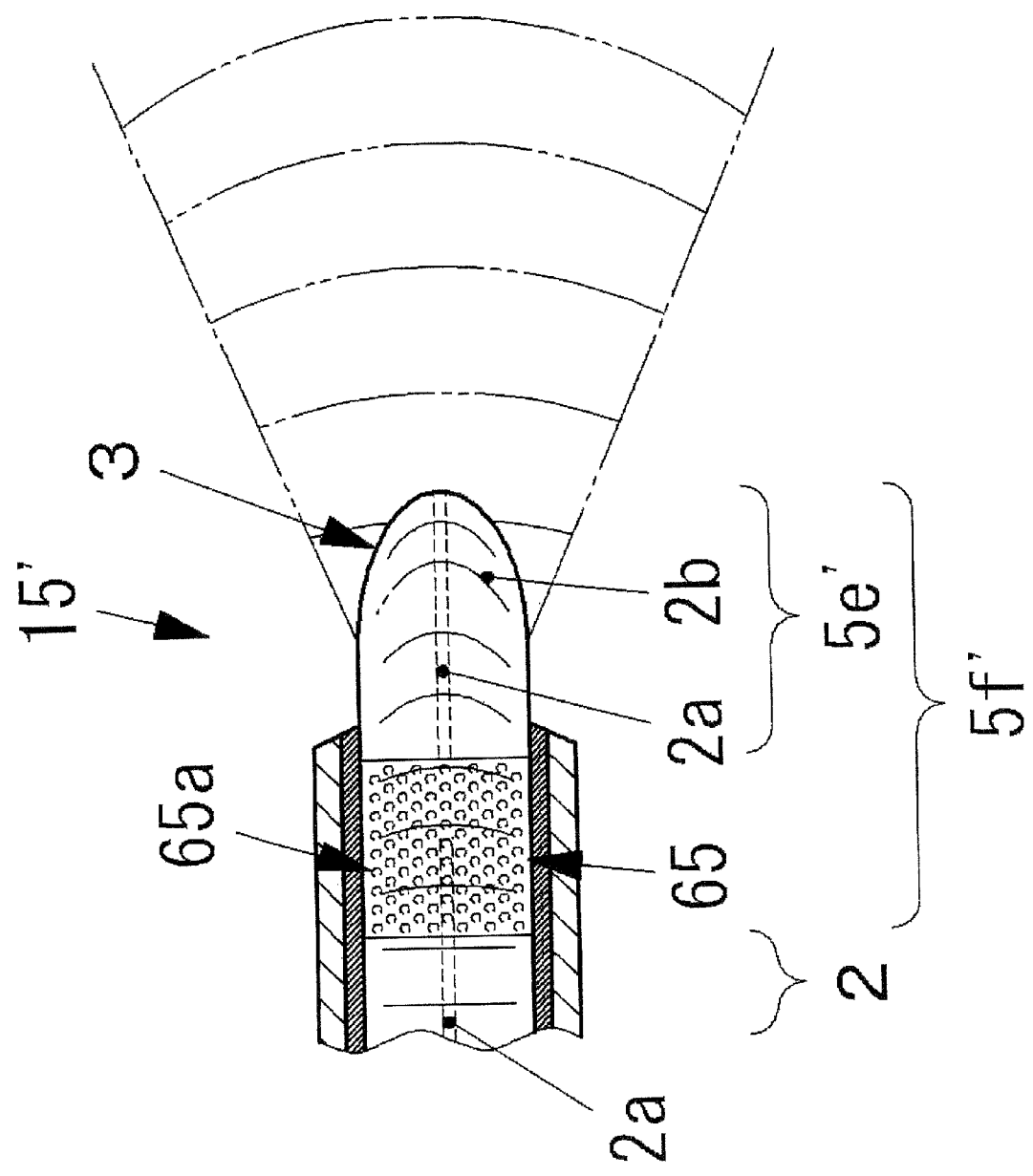
FIG. 31 is a schematic view illustrating propagation and radiation of light in the light-illuminating probe of FIG. 29.

FIGS. 29(a), (b) and (c) schematically illustrate a light-illuminating probe 15' given in a tenth embodiment of the present invention. FIG. 30 is a cross-sectional view taken along line N-N of FIG. 29(a). FIG. 31 illustrates propagation and radiation paths of light in the light-illuminating probe 15' given in the present embodiment. The same components as those of the aforementioned embodiments are denoted by the same reference numerals, and the description thereof is omitted and simplified.

The tenth embodiment is different from the aforementioned embodiments, particularly, the ninth embodiment in that the light-illuminating probe 15' includes, as a substitute for the aforementioned transmissive diffusing plate 16, a diffusing portion 65 is inserted in an optical fiber 2 constructed with a core 2a and a clad 2b which has a refractive index lower than that of the core 2a and surrounds the core 2a, and the diffusing portion 65 is provided with a plurality of cavities formed through the core 2a and the clad 2b. Due to the formation of the diffusing portion 65, the light-radiating portion 5f' is constructed with the diffusing portion 65 and the distal end portion 5e'. The distal end portion 5e' has a refractive index distribution equal to that of the optical fiber 2, and a distal end portion thereof is provided with the lens portion 3. The light-illuminating probe 15' has a spatial refractive index distribution in which the optical fiber 2 and the light-radiating portion 5f'' are distinguished from each other.

Plenty of cavities 65a is also formed in a diffusing portion 65 over a certain portion along the axial direction of the optical fiber 2, and the cavities 65a are formed to have a circular cross section in which the diameters of the cavities 65a are equal to each other. The inner portions of the cavities 65a are filled with air or maintained in a vacuum state. Therefore, the refractive index of the inner portions of the cavities 65a is set to be lower than that of the clad 2b.

The cavities 65a are formed by ultra short light pulses emitted from a femto-second laser focused in the inner portion of the optical fiber 2 and vaporizing a material of the optical fiber in the light-focused region in the inner portion of the optical fiber 2 to generate cavity sites.

As illustrated in FIG. 31, when the propagating light that propagates from the optical fiber 2 to the light-radiating portion 5f' is incident to the diffusing portion 65, the light is diffused due to the diffusing portion 65. Since the refractive index of the cavities 65a is lower than that of the clad 2b, the light is radiated with a wide radiating angle at the cavities 65a, the mode of the propagating light is changed from a propagation mode to a radiation mode, and the wave front thereof is gradually changed from a flat plane to a curved plane. The propagating light that is incident to the lens portion 3 is emitted as an external radiating light from the lens portion 3 to an outside of the light-illuminating probe 15'. Since the mode of the propagating light in an inner portion of the light-radiating portion 5f' is changed to the radiation mode, a condensing function of the lens portion 3 is reduced, and the propagation of the light in the free space is maintained more effectively in the radiation mode. Therefore, in comparison to a conventional light-illuminating probe, it is possible to enlarge an illuminated spatial range of the external illuminating light.

In addition, since the spread angle of the propagating light is increased due to the diffusion in the diffusing portion 65 before the propagating light approaches the lens portion 3 which is the light-radiating portion, the illuminated spatial range of the external illuminating light can be enlarged, so that generation of back scattering light can be suppressed.

Eleventh Embodiment

Figure 33:
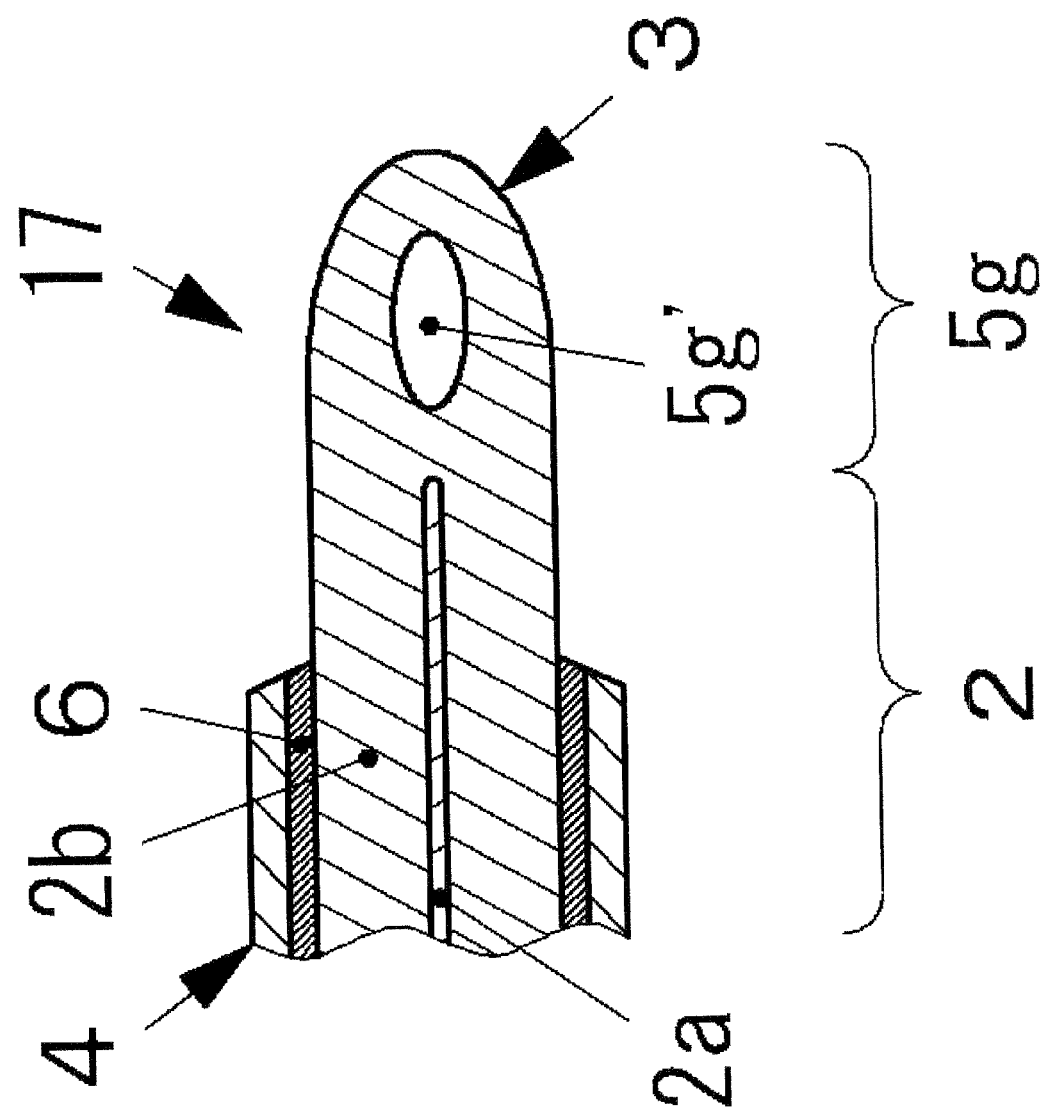
FIG. 33 is a cross-sectional view taken along line J-J of FIG. 32(a).
Figure 34:
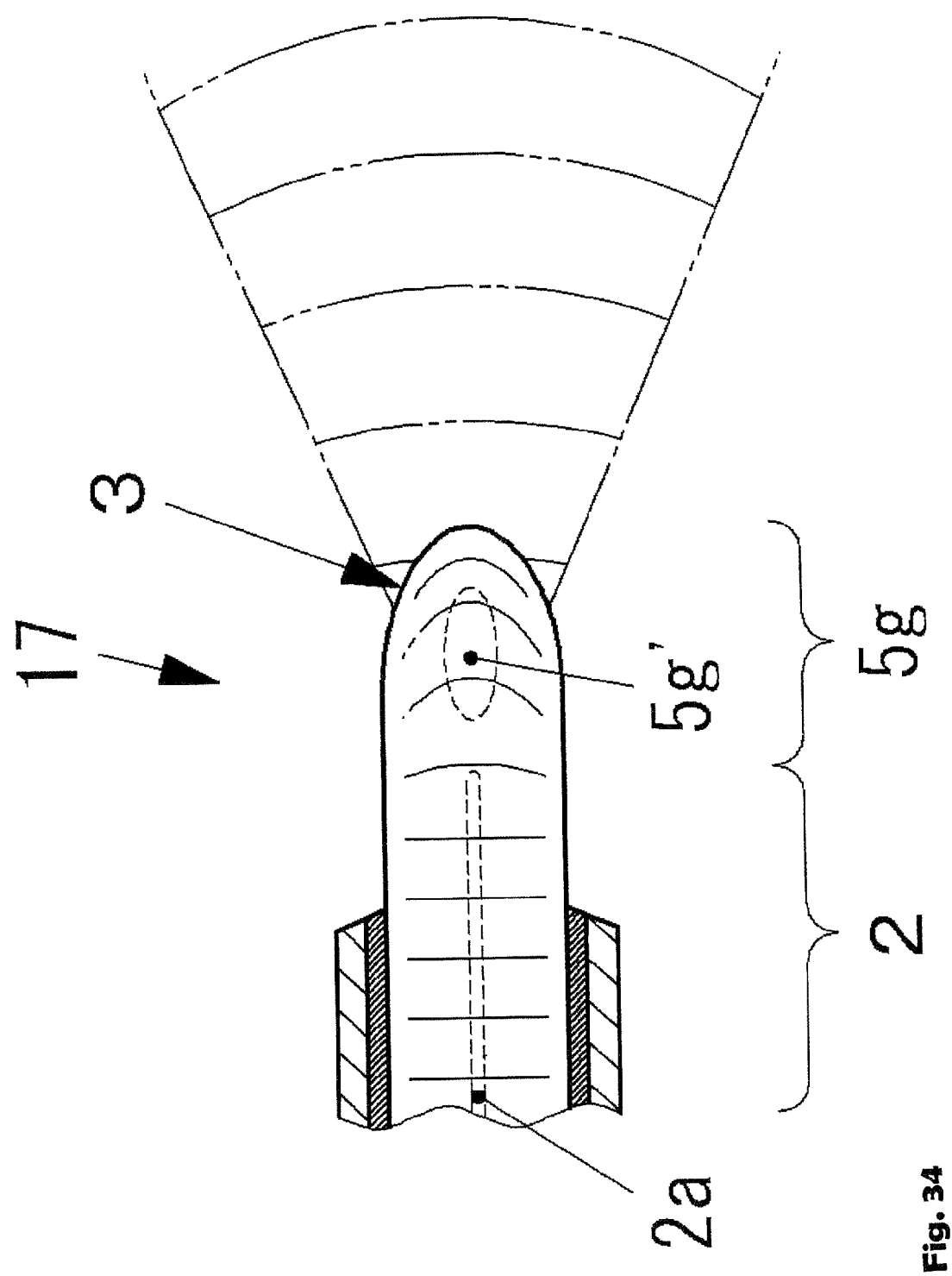
FIG. 34 is a schematic view illustrating propagation and radiation of light in the light-illuminating probe of FIG. 32.

FIGS. 32(a), (b) and (c) schematically illustrate a light-Illuminating probe 17 given in an eleventh embodiment of the present invention. FIG. 33 is a cross-sectional view taken along line J-J of FIG. 32(a). FIG. 34 illustrates propagation and radiation paths of light in the light-illuminating probe 17 given in the present embodiment. The same components as those of the aforementioned embodiments are denoted by the same reference numerals, and the description thereof is omitted and simplified.

The eleventh embodiment is different from the aforementioned embodiments, particularly the third embodiment in that a refractive index distribution (spatial refractive index distribution) of a light-radiating portion 5g is formed to be uniform and equal to that of a clad 2b, and a hollow site 5g' is provided in an inner portion of the light-radiating portion 5g. The inner portion of the hollow site 5g' is filled with air or maintained in a vacuum state. Therefore, the refractive index of the inner portion of the hollow site 5g' is set to be lower than that of the clad 2b.

Figure 35:
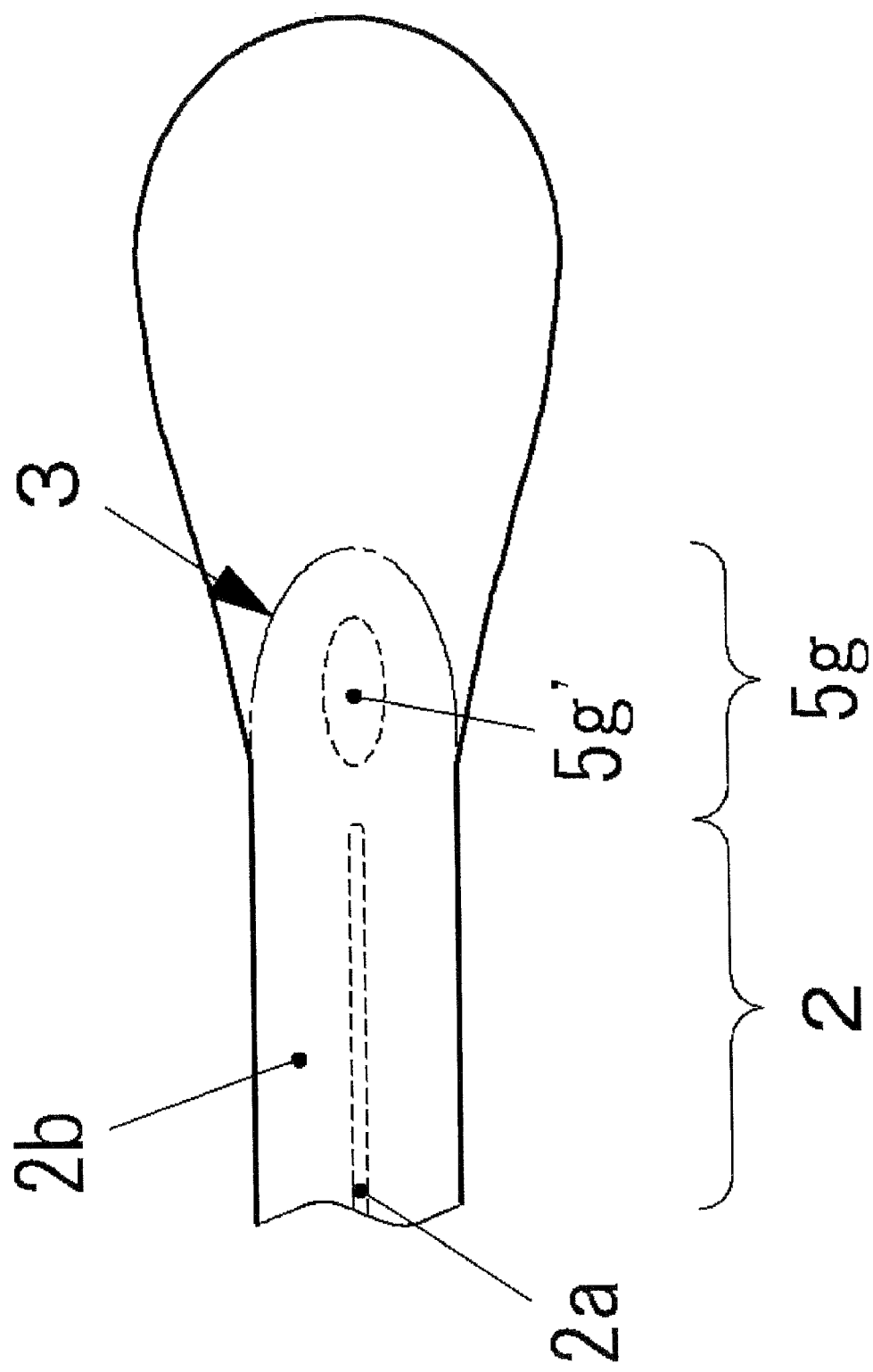
FIG. 35 is a view for explaining a method of manufacturing a refractive index structure of a light-radiating portion in the light-illuminating probe of FIG. 32.

Now, a method of manufacturing the light-radiating portion 5g is described. Firstly, the hollow site 5g' is formed by illuminating and focusing the light emitted from a femto-second laser on a light-guiding cable (core 2a) of an extension of the optical fiber and vaporizing a material of the optical fiber in the light-focused region, and the extension of the optical fiber is heated and fused to have a shape of droplet due to a surface tension thereof (see FIG. 35). Accordingly, the refractive index distribution of the extension of the optical fiber except for the hollow site 5g' is uniform and equal to that of the clad 2b. Next, the extension of the optical fiber that has a shape of droplet is subject to a grinding or polishing process to a portion indicated by a dotted dashed line of the figure, so that the lens portion 3 is formed and the light-radiating portion 5g is formed.

As illustrated in FIG. 34, due to the termination of the region of the core 2a, the mode of the propagating light that propagates from the optical fiber 2 to the light-radiating portion 5g is changed from a propagation mode to a radiation mode, and the wave front thereof is gradually changed from a flat plane to a curved plane. Since the refractive index of the hollow site 5g' that is formed in the inner portion of the light-radiating portion 5g is lower than that of the clad 2b, the light is radiated with a wide spread angle at the hollow site 5g', and the light is emitted from the lens portion 3 to an outside of the light-illuminating probe 17. Therefore, in comparison to the light-illuminating probe 8 given in the third embodiment, it is possible to enlarge an illuminated spatial range of the external illuminating light.

In addition, since the spread angle of the propagating light is increased before the propagating light approaches the lens portion 3, the illuminated spatial range of the external illuminating light can be enlarged, so that generation of back scattering light can be suppressed.

Twelfth Embodiment

Figure 37:
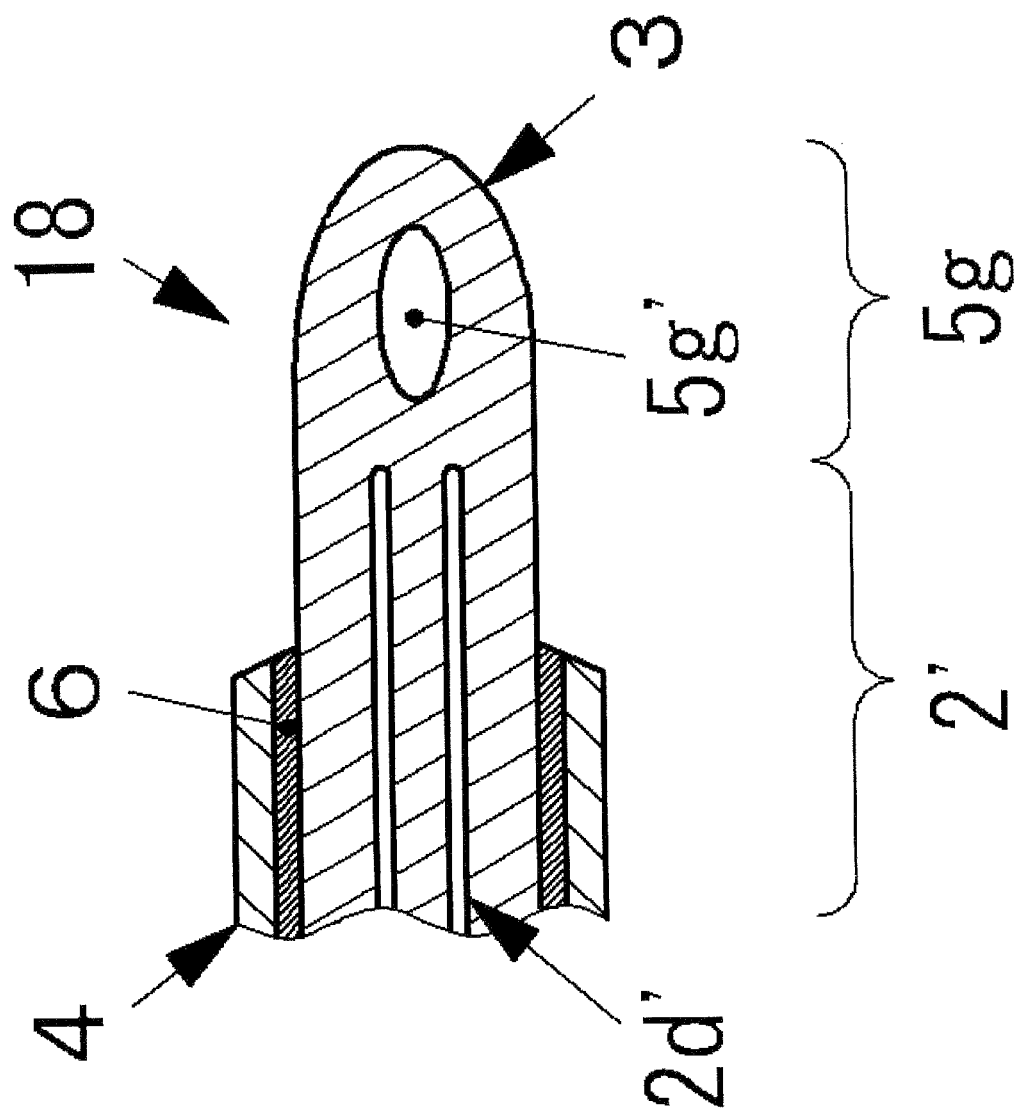
FIG. 37 is a cross-sectional view taken along line K-K of FIG. 36(a).
Figure 38:
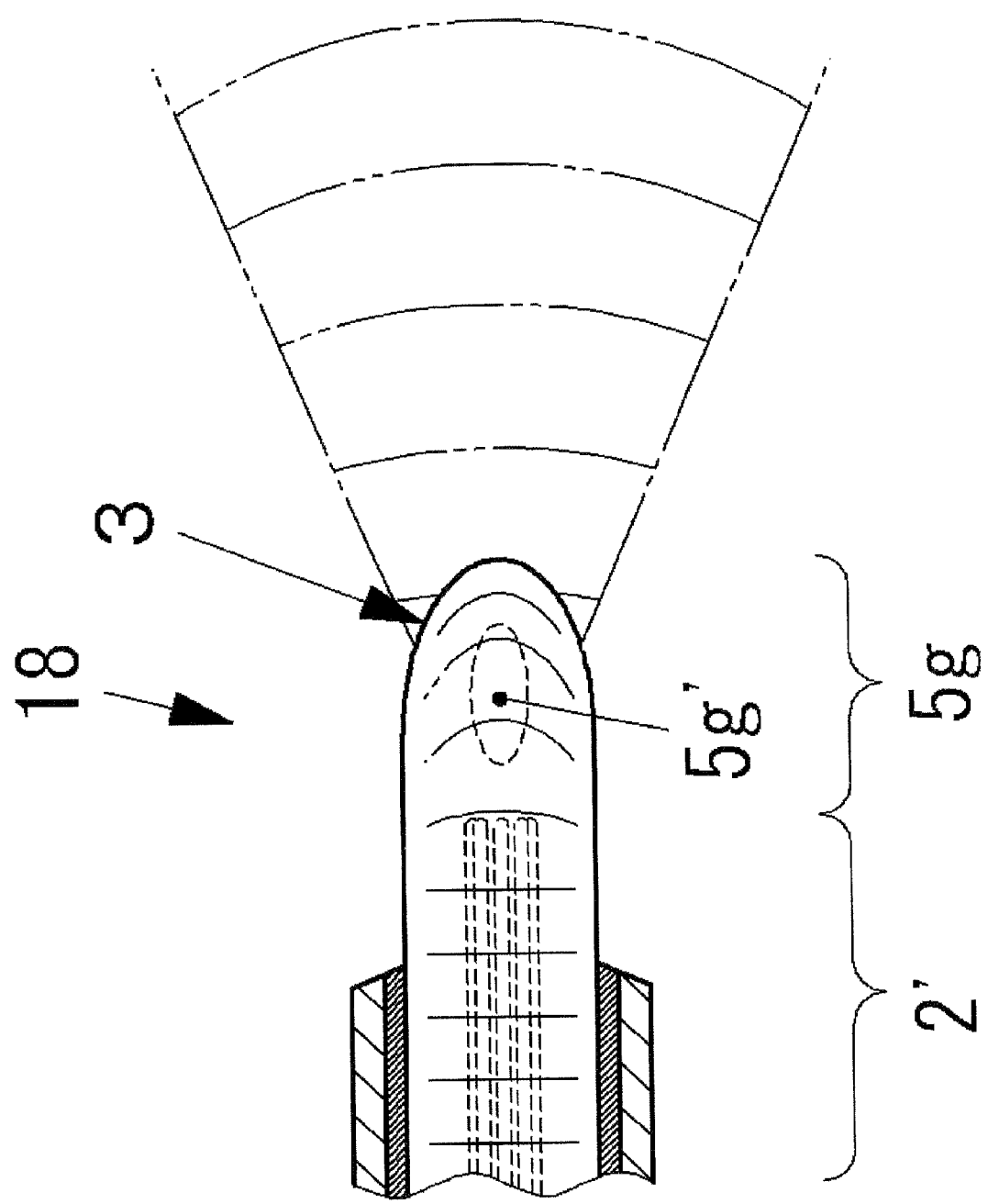
FIG. 38 is a schematic view illustrating propagation and radiation of light in the light-illuminating probe of FIG. 36.
Figure 39:
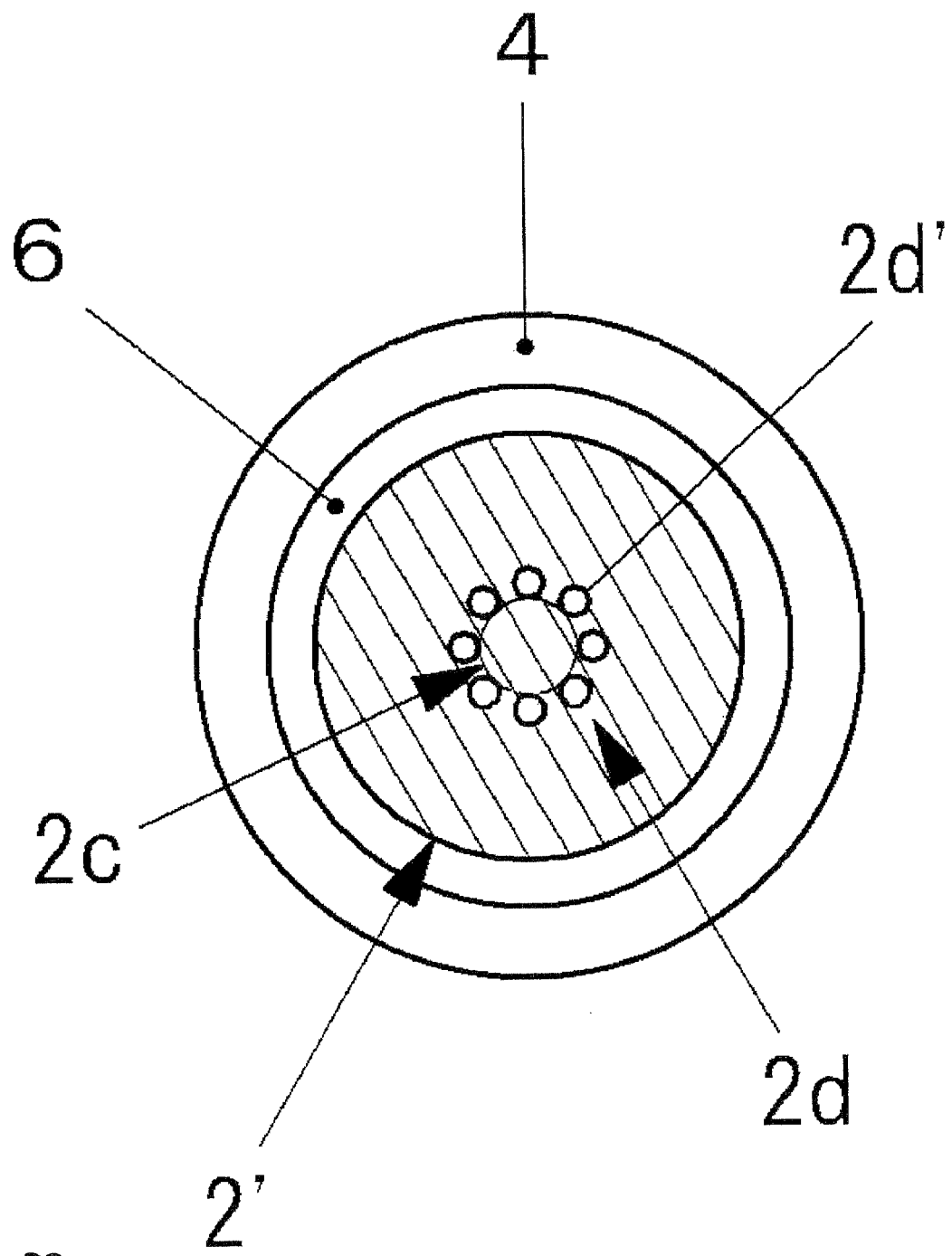
FIG. 39 is a cross-sectional view taken along line L-L of FIG. 36(a).

FIGS. 36(a), (b) and (c) schematically illustrate a light-illuminating probe 18 given in a twelfth embodiment of the present invention. FIG. 37 is a cross-sectional view taken along line K-K of FIG. 36(a). FIG. 38 illustrates propagation and radiation paths of light in the light-illuminating probe 18 given in the present embodiment. FIG. 39 is a cross-sectional view taken along line L-L of FIG. 36(a). The same components as those of the aforementioned embodiments are denoted by the same reference numerals, and the description thereof is omitted and simplified.

The twelfth embodiment is different from the aforementioned embodiments, particularly, the eleventh embodiment in that an optical fiber 2' having a spatial refractive index distribution constructed with a light-guiding cable 2c functioning as a core and a peripheral portion 2d functioning as a clad is used as a light-transmitting portion, as illustrated in FIG. 39. The optical fiber 2' is made of quartz or the like, and the central portion 2c has the same construction as that of the quartz.

More specifically, the peripheral portion 2d is provided with a plurality of hollow cylinders 2d' which are disposed to extend in an axial direction of the optical fiber 2' and surround the light-guiding cable 2c, and a refractive index thereof is set to be lower than that of the light-guiding cable 2c. Therefore, the light propagates the inner portion of the optical fiber 2' in a manner that the light is confined into the light-guiding cable 2c.

Figure 40:
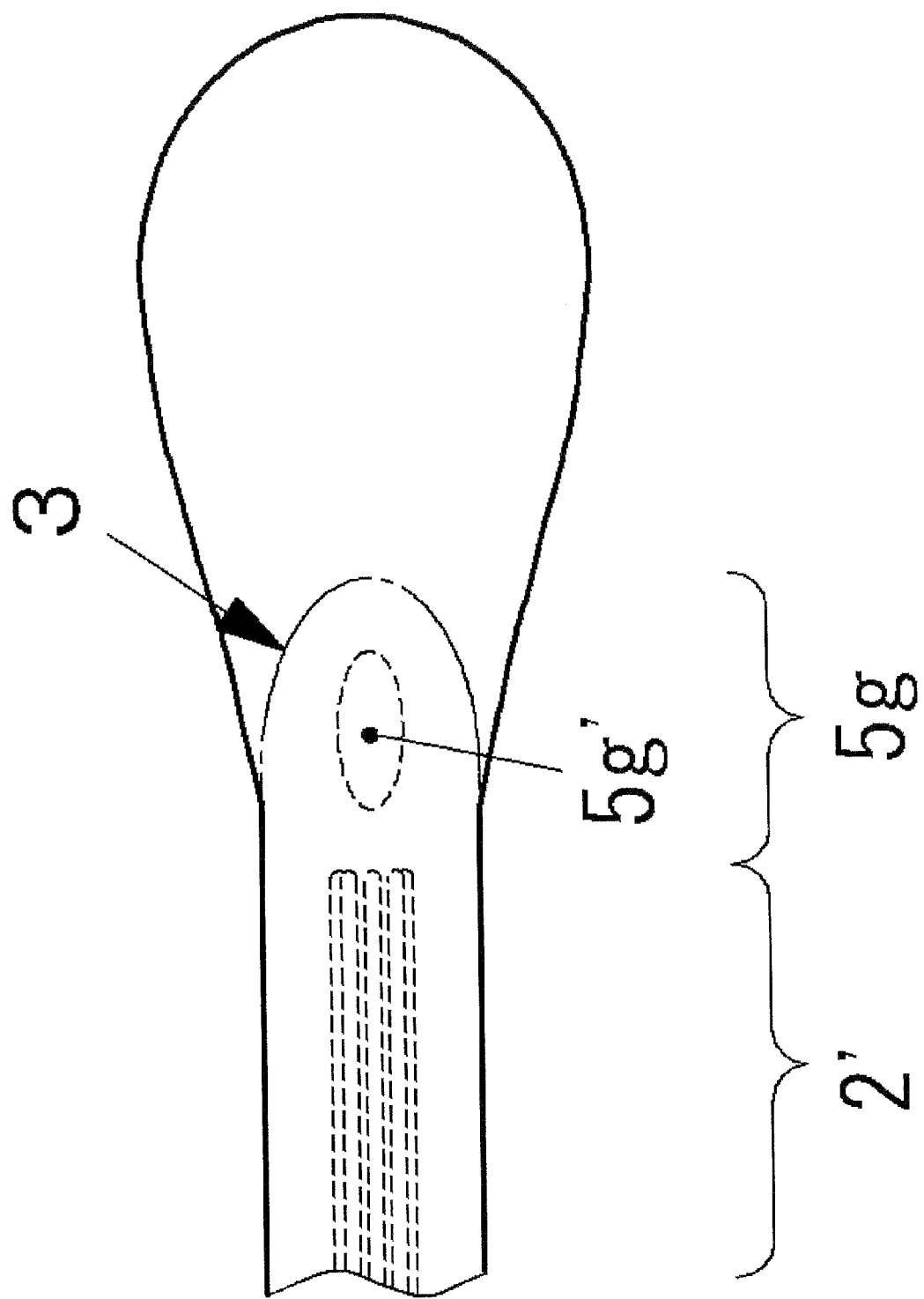
FIG. 40 is a view for explaining a method of manufacturing a refractive index structure of an optical fiber in the light-illuminating probe of FIG. 36.

Now, a method of manufacturing the light-radiating portion 5g is described. Firstly, the light-guiding cable of the extension of the optical fiber 2' is illuminated with a femto-second laser. During the illumination, a light-condensing point of the femto-second laser is aligned with the light-guiding cable 2c except from the hollow cylinders 2d', so that the hollow cylinders 2d' are fused and closed in a not-hollow state. After the hollow cylinders 2d' of the extension of the optical fiber 2' is closed, the light-guiding cable of the extension of the optical fiber 2' is again illuminated and light-condensed with the femto-second laser, and the material of the optical fiber 2' in the light-condensing region is vaporized, so that the hollow site 5g' is formed. Next, the extension of the optical fiber 2' is heated and fused to have a shape of droplet due to a surface tension thereof (see FIG. 40). Accordingly, the refractive index distribution of the light-radiating portion 5g except for the hollow site 5g' is uniform and equal to that of the light-guiding cable 2c of the optical fiber 2'. Next, the extension of the optical fiber 2' that has a shape of droplet is subject to a grinding or polishing process to a portion indicated by a dotted dashed line of the figure, so that the lens portion 3 is formed and the light-radiating portion 5g is formed.

Now, the propagation and radiation of light in the light-illuminating probe 18 are described with reference to FIG. 38. As illustrated in FIG. 38, the light is incident to the other end (not shown) of the optical fiber 2' to be confined to the light-guiding cable 2c, and the light propagates through the inner portion of the optical fiber 2' toward the lens portion 3. The propagating light that propagates through the inner portion of the optical fiber 2' is maintained in a propagation mode, and the wave fronts are maintained to be perpendicular to the axial direction of the optical fiber 2' and parallel to each other.

Due to the change of the refractive index distribution, the mode of the propagating light that propagates from the optical fiber 2' to the light-radiating portion 5g is changed from a propagation mode to a radiation mode, and the wave front is gradually changed from a flat plane to a curved plane. The light is radiated at the hollow site 5g' with a wide radiating angle and emitted from the lens portion 3 to an outside of the light-illuminating probe 18.

In addition, since the spread angle of the propagating light is increased before the propagating light approaches the lens portion 3, the illuminated spatial range of the external illuminating light can be enlarged, so that generation of back scattering light can be suppressed.

Thirteenth Embodiment

FIGS. 41(a), (b) and (c) are schematic partial left-side cross-sectional views illustrating light-illuminating probes 25, 26, and 27 given in a thirteenth embodiment of the present invention. The same components as those of the aforementioned embodiments are denoted by the same reference numerals, and the description thereof is omitted and simplified.

The thirteenth embodiment may be implemented in several types. In a type illustrated in FIG. 41(a), a transmissive diffusing plate 16 is disposed in an optical fiber 2, that is, a light-transmitting portion. In another type illustrated in FIG. 41(c), the transmissive diffusing plate 16 is disposed between the optical fiber 2 and a light-radiating portion 5d. In still another type illustrated in FIG. 41(b), the transmissive diffusing plate 16 is disposed between the optical fiber 2 and an optical member 12.

The propagation and radiation of the light in light-illuminating probes 25 to 27 are basically the same as those of the ninth embodiment. The propagating light that propagates from the optical fiber 2 to the light-radiating portion 5b, 5c, or 5d is diffused and emitted as an external radiating light from the lens portion to the probe 25, 26, or 27. In each of the light-illuminating probes 25 to 27, in addition to the transmissive diffusing plate 16, each of the light-radiating portions 5b, 5c, and 5d are additionally provided, so that the propagating light diffused from the transmissive diffusing plate 16 is further radiated at each of the light-radiating portions 5b, 5c, and 5d to be emitted from the lens portion 3. Therefore, in comparison to the light-illuminating probe 15 given in the ninth embodiment, it is possible to enlarge an illuminated spatial range of the external illuminating light.

In addition, since the propagating light is radiated in the transmissive diffusing plate 16 before the propagating light approaches the lens portion 3 which is the light-radiating portion, the illuminated spatial range of the external illuminating light can be enlarged, so that generation of back scattering light can be suppressed.

In addition, the construction of FIG. 41(b) may be modified to be the construction of FIG. 41(b) that the transmissive diffusing plate 16 is disposed in the optical fiber 2.

Although FIGS. 41(a), (b) and (c) illustrate the types that the transmissive diffusing plate 16 is provided to the light-illuminating probes 25, 26 and 27 given in the third, sixth, and eighth embodiments, respectively, new types of light-illuminating probes may be formed by cutting the optical fiber 2 of the light-illuminating probes given in the aforementioned embodiments (excepting the ninth embodiment) or cutting a portion between the optical fiber 2 and the light-radiating portions 5b, 5c and 5d and by inserting the transmissive diffusing plate 16.

Fourteenth Embodiment

Figure 43:
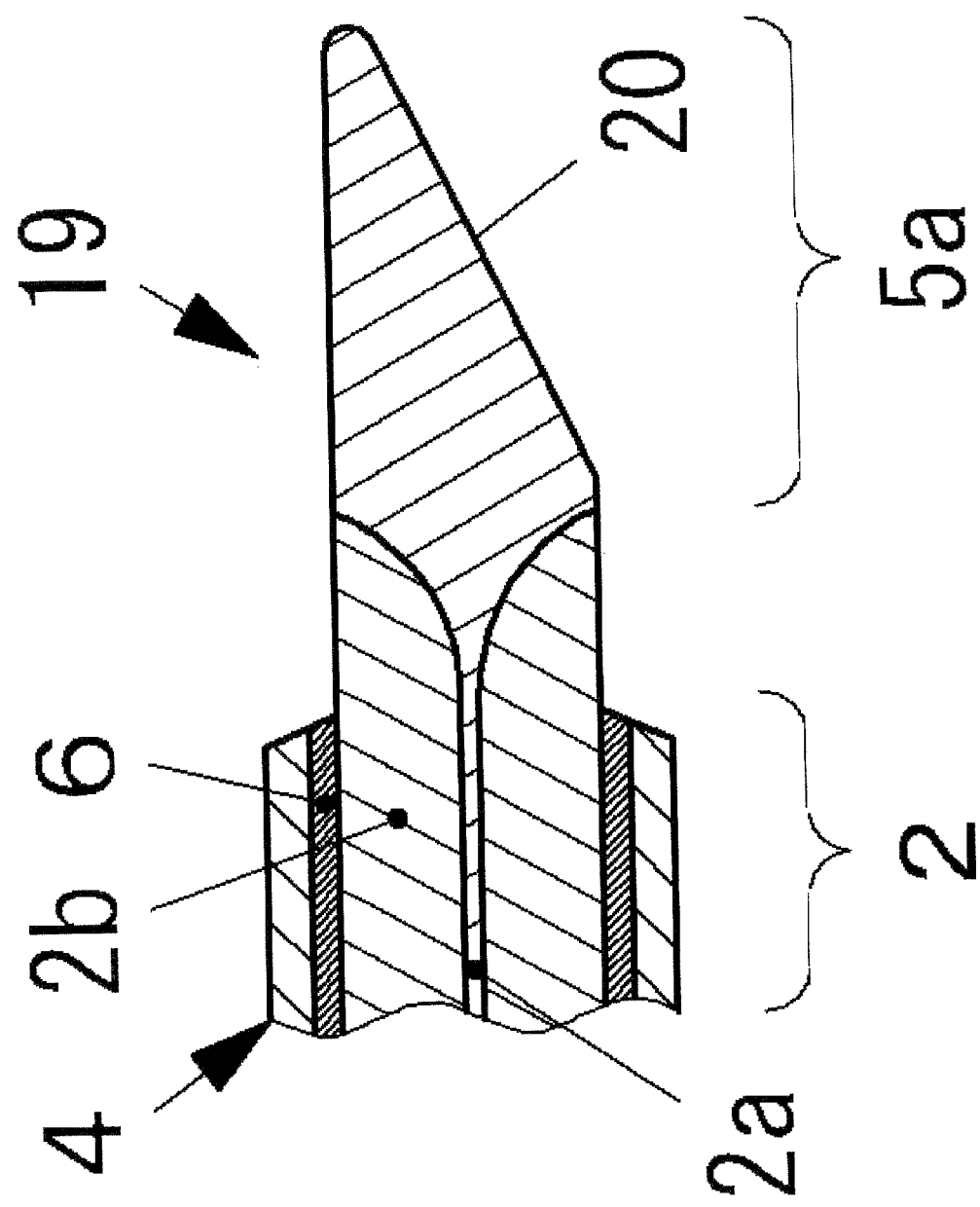
FIG. 43 is a cross-sectional view taken line M-M of FIG. 42(a).
Figure 44:
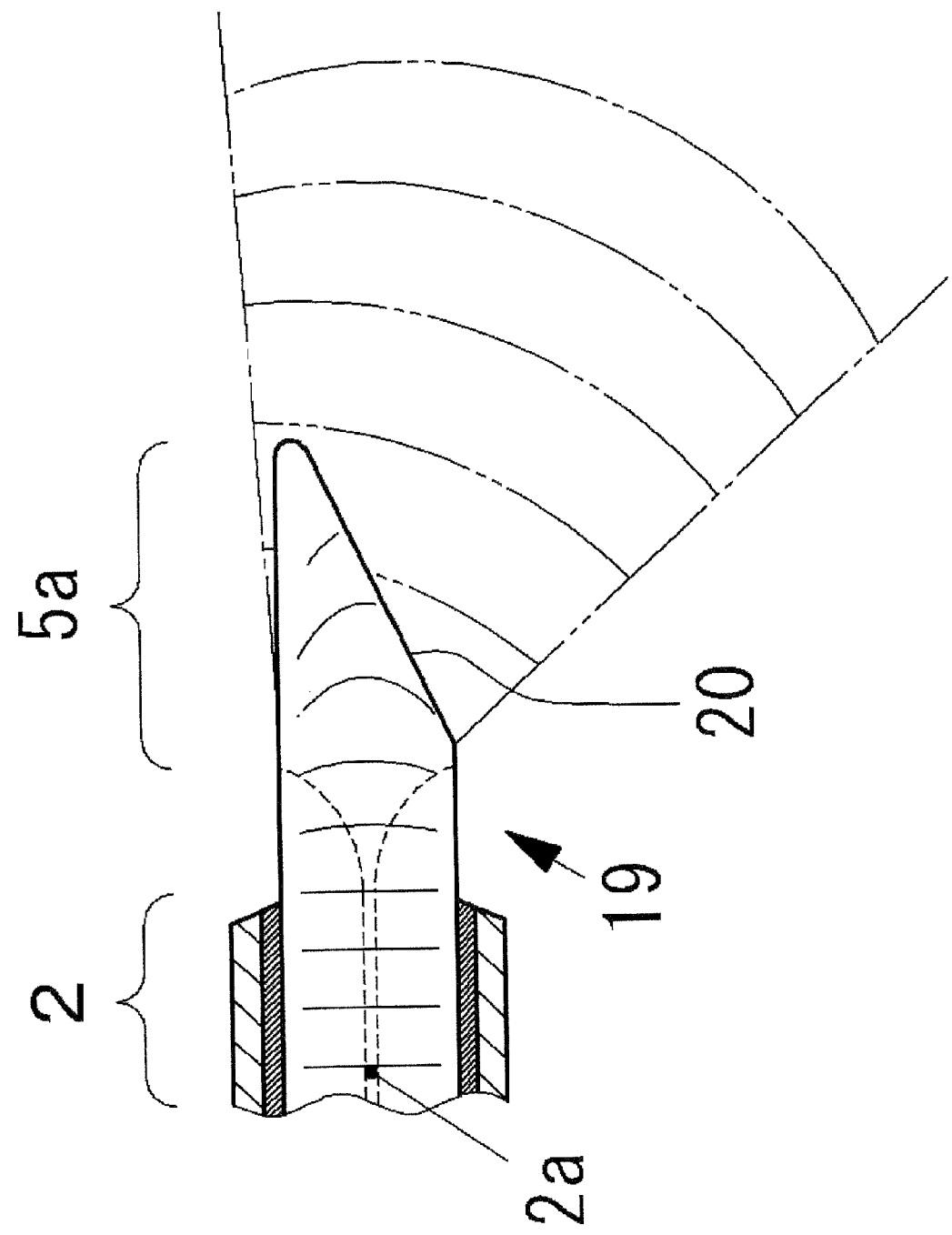
FIG. 44 is a schematic view illustrating propagation and radiation paths of light in the light-illuminating probe of FIG. 42.

FIGS. 42, (b) and (c) schematically illustrate a light-illuminating probe 19 given in a fourteenth embodiment. FIG. 42(a) is a plane view, FIG. 42(b) is a partial left-side cross-sectional view, FIG. 42(c) is a bottom view, and FIG. 42(d) is a front view. FIG. 43 is a cross-sectional view taken line M-M of FIG. 42(a), and FIG. 44 illustrates propagation and radiation paths of light in the light-illuminating probe 19 given in the embodiment. The same components as those of the aforementioned embodiments are denoted by the same reference numerals, and the description thereof is omitted and simplified.

The fourteenth embodiment is different from the aforementioned embodiments, particularly, the first embodiment in that one flat plane 20 is formed as a substitute for the lens portion 3 of the previous embodiments to the distal end portion of the light-radiating portion 5a, and the distal end portion is formed in a pointed shape. The flat plane 20 is formed not to be parallel to an axial direction of the optical fiber 2 which is a light-transmitting portion with a slanted angle of less than 90 degree. Therefore, the radiation of light from the optical fiber 2 is formed as illustrated in FIG. 44.

As illustrated in FIG. 44, the light that is incident to the other end (not shown) of the optical fiber 2 propagates through the inner portion of the optical fiber 2 toward the light-radiating portion 5a. The propagating light that propagates through the inner portion of the optical fiber 2 is maintained in a propagation mode, and the wave fronts are maintained to be perpendicular to the axial direction of the core 2a and parallel to each other.

When the light propagates from the optical fiber 2 to the light-radiating portion 5a, due to the change of the refractive index, the refractive index of the core 2a is gradually enlarged, so that the refractive index is substantially equal in the light-radiating portion 5a. Therefore, a total reflection of the propagating light disappears, so that the wave front is gradually changed from a flat plane to a curved plane. In addition, the mode of the propagating light is changed from a propagation mode to a radiation mode. The propagating light that propagates to the distal end portion of the light-radiating portion 5a is emitted as an external radiating light to an outside of the light-illuminating probe 19. At the time of emission of light, the external illuminating light is refracted on the slanted flat plane 20, so that the external illuminating light is illuminated at a right-downward slanted direction, that is, the refraction direction as illustrated in FIG. 44.

The mode of the propagating light in the inner portion of the light-radiating portion 5a is changed to the radiation mode, and the propagation of the light in the free space is maintained more effectively in the radiation mode. Therefore, in comparison to a conventional light-illuminating probe 19, it is possible to enlarge an illuminated spatial range of the external illuminating light. In addition, since the spread angle of the propagating light is increased before the propagating light approaches the distal end portion of the light-radiating portion, the illuminated spatial range of the external illuminating light can be enlarged, so that generation of back scattering light can be suppressed.

Since the distal end portion is formed in a pointed shape, when an eyeball is pierced with the light-illuminating probe 19 to observe fundus or practice fundus surgery, simple laceration occurs on a surface of the eyeball. Therefore, the eyeball can be rapidly restored without complicated laceration of the surface of the eyeball after the light-illuminating probe 19 is removed.

The flat plane 20 is formed by performing a well-known grinding or polishing process. Alternatively, the flat plane 20 may be formed to the distal end portion of the light-radiating portion or the distal end portion of the optical member of the light-illuminating probes given in the aforementioned embodiments in the same shape as that of FIG. 42(a), (b) and (c) For example, FIG. 45 (a), (b) and (c) illustrates partial left-side cross-sectional views of the light-illuminating probes in which the flat plane 20 is formed as a substitute of the lens portion 3 to the distal end portion of the light-radiating portion or the distal end portion of the optical member according the second, third, and eighth embodiment, respectively.

Although one flat plane 20 is formed to the light-illuminating probe 19 in the embodiment, a plurality of flat planes 20 may be formed to the end portion of the light-radiating portion or the end portion of the optical member as a modification of the embodiment. In addition, as another example of the pointed shape, the end portion of the light-radiating portion may be formed in a conical shape.

Fifteenth Embodiment

FIG. 46 illustrates a fifteenth embodiment of the present invention. The same components as those of the aforementioned embodiments are denoted by the same reference numerals, and the description thereof is omitted and simplified.

The light-illuminating probes 21 and 22 illustrated in FIG. 46(a), (b) and (c) are different from those of the aforementioned embodiments in that a plurality of steps 23 and 24 are provided to the distal end portion of the light-radiating portion 5a. In the embodiment, the term "step" denotes a shape of step, but it does not denote a difference between heights of steps. FIG. 46(a) illustrates the light-illuminating probe 21 in which a plurality of steps 23 having a shape of circular ring are disposed in a concentric shape. FIG. 46(b) illustrates the light-illuminating probe 22 in which a plurality of steps 24 having an outer shape of a combination of arc and plane are disposed. FIG. 46(c) is a side cross-sectional view of FIG. 46(b).

A light radiating plane on which the steps 23 and 24 are formed is provided to the distal end portion of the light-radiating portion 5a, so that the illuminated spatial range of the external illuminating light can be enlarged, similarly to the aforementioned embodiments. Alternatively, the spread angle of the propagating light is increased before the propagating light approaches to the end portion of the optical fiber 2, so that the illuminated spatial range of the external illuminating light can be enlarged. Accordingly, generation of back scattering light may be suppressed. Alternatively, the steps 23 and 24 may be respectively formed to the distal end portion of the light-radiating portion 5a of the light-illuminating probe 21 and 22 given in the aforementioned embodiments in the same shape as that of FIG. 46.

In addition, instead of the steps 23 and 24, a surface of the distal end portion of the light-radiating portion of each of the light-illuminating probes 21 and 22 respectively given in the aforementioned embodiments are formed in a shape of polished glass having a rough surface provided with a plurality of micro concave-convex portions, so that the propagating light can be illuminated with a spread angle, as a modification of the embodiment.

As illustrated in FIGS. 52, 53, 54, 55 and 56, in the light-illuminating probes 69, 70, 72, 73, and 74, respectively, in which a light-guiding optical fiber 67 is provided as a light-transmitting portion, the distal end portions are doped with a doping agent of Er, Nd, Ho, Tm, Pr, Sm, Dy, Yb, Ti, or the like, so that only the refractive index of the distal end portions are higher than those of the light-guiding optical fiber 67. As a doping method, after ion injection, the extension of the optical fiber may be subject to an annealing process, or the extension may be exposed to a vapor of a doping agent or a plasma ambience obtained from plasma of the vapor. Alternatively, the distal end portion of the light-guiding optical fiber 67 may be immersed into a low-temperature fusing quartz pool in which the doping agent is fused.

Sixteenth Embodiment

Figure 47:
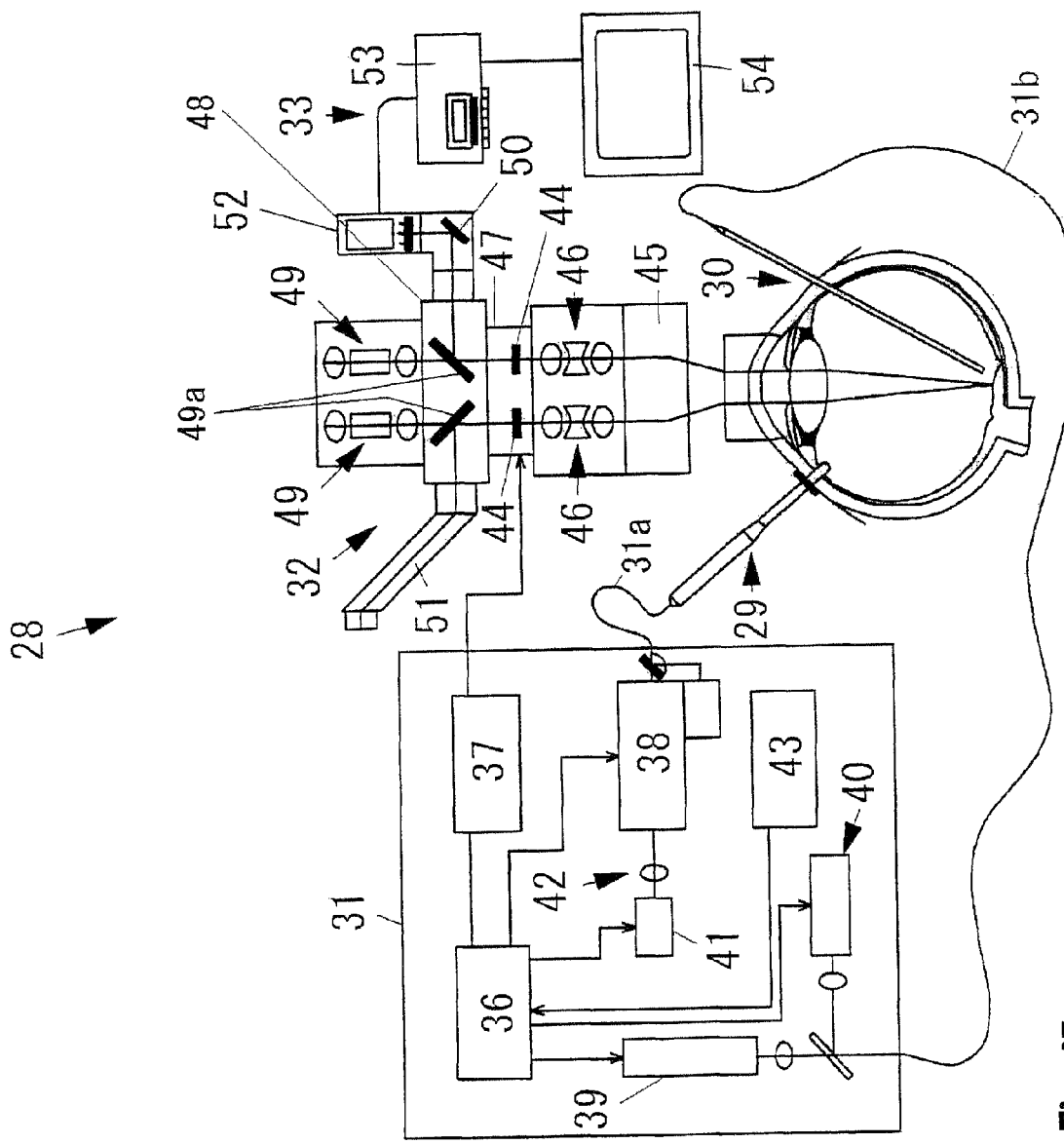
FIG. 47 is a view for explaining a construction of a fundus observing apparatus or a fundus surgery apparatus using the light-illuminating probe given in any one of the aforementioned embodiments.

FIG. 47 illustrates a sixteenth embodiment of the present invention. FIG. 47 is a view for explaining a construction of a fundus observing apparatus 28 or a fundus surgery apparatus 28 (hereinafter, referred to as an apparatus 28) using an intraocular illuminating probe 29 given in any one of the aforementioned first to fourteenth embodiments. The light-illuminating probe given in any one of the aforementioned first to fifteenth embodiments and those given in FIGS. 52, 53, 54, 55 and 56, may be used as an intraocular illuminating probe 29 and an apparatus 28 illustrated in FIG. 47. As an example, the apparatus 28 may be used to treat, particularly, age-related macular degeneration (AMD).

The apparatus 28 may be provided with a fundus surgery apparatus and a fundus observing apparatus so as to perform fundus observation during fundus surgery. More specifically, the apparatus 28 includes an intraocular illuminating probe 29, a photocoagulating probe 30, a light source unit (light source means) 31, an intraocular observation device 32, and an intraocular monitor (intraocular image developing means) 33.

Figure 48:
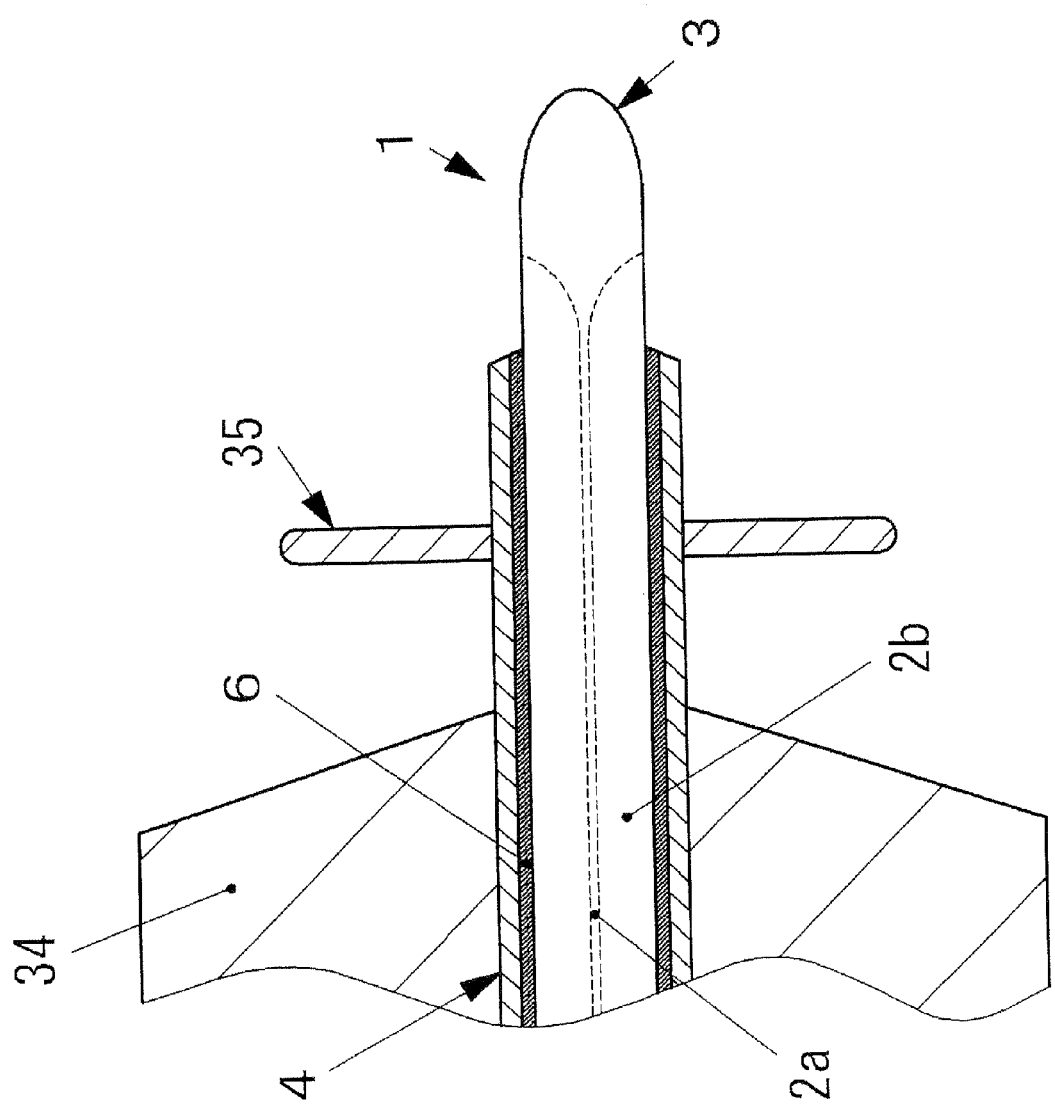
FIG. 48 is a schematic partial left-side cross-sectional view illustrating a light-illuminating probe given in the present invention, in which a hand piece and an annular ring portion are provided to a cannula.

The intraocular illuminating probe 29 is connected to the light source unit 31 through an illuminating light-guiding cable 31a. As disclosed in each of the aforementioned embodiment, the optical fiber 2 or 2' is covered with a cannula 4, and a portion of the cannula 4 is covered with a hand piece 34 as illustrated in FIG. 48. In addition, an annular ring portion 35 is formed on an outer circumferential surface of the cannula 4 in a shape of ring to protrude from the outer circumferential surface of the cannula 4 in the outward direction.

The lightening light that is input from the light source unit 31 is induced to the intraocular illuminating probe 29 through the illuminating light-guiding cable 31a to be emitted from the distal end portion of the intraocular illuminating probe 29 constructed with a light-illuminating probe 1. As described above, in the intraocular illuminating probe 29, due to the radiation before propagation to the lens portion, the radiation in the inner portion of the optical member, the radiation at the distal end portion of the light-radiating portion, or the diffusion at the transmissive diffusing plate, the illuminated spatial range of the external illuminating light can be enlarged, so that a wide area of an inner portion of a tested eyeball can be illuminated with light. Therefore, a cell, a tumor, or a diseased part marked with a fluorescent agent can be easily detected, and the fundus observation can be accurately performed by fluorescent-light fundus illumination.

The photocoagulating probe 30 is connected to the light source unit 31 through a coagulating light-guiding cable 31b and has a shape of fiber similarly to the intraocular illuminating probe 29. The photocoagulating light that is input from the light source unit 31 is induced to the photocoagulating probe 30 to be emitted from the extension of the other side.

The light source unit 31 includes a light source controller (light source control means) 36, a filter operation synchronizer 37, a light output safety controller (light output safety control means) 38, an argon ion laser source 39, a guiding-light laser diode 40, a first laser diode 41, an optic system 42, and a laser output detector 43. In addition, the light source unit 31 further includes a lightening beam output switch (not shown), a coagulating beam output switch (not shown), and a lightening-coagulating conversion switch (not shown).

The light source controller 36 controls emission of each light source so as to observe fundus during surgery. The filter operation synchronizer 37 performs conversion of filter operations, that is, insertion and ejection of a laser beam filter 44 in a light path by driving a filter conversion unit of the intraocular observation device 32. The conversion control is performed based on a type of light emitted from the light source unit 31.

The light output safety controller 38 controls output of several types of laser beam used for intraocular lightening so that the output cannot exceed a safety level.

The argon ion laser source 39 is a surgery light source which emits a coagulating laser beam which is illuminated on a target site (to-be-practiced site) of the fundus in the tested eyeball through the distal end portion of the photocoagulating probe 30. A krypton red laser, an argon direct laser, and a krypton yellow laser may be used.

The first laser diode 41 is driven as a lightening light source (visible laser source) to excite fluorescein to emit fluorescent light, so that a visible laser having a wavelength range of green to blue is emitted as a lightening laser beam for lightening the interior of eyeball. A laser beam having a wavelength range of 465 nm to 490 nm can be very suitable for light of exciting fluorescein. Therefore, in the embodiment, a wavelength of the visible laser beam is set to be about 480 nm.

The lightening beam output switch and the coagulating beam output switch are driving switches for driving the light source unit 31 to input the lightening laser beam or the coagulating laser beam. The lightening-coagulating conversion switch converts types of laser beams emitted from the light source unit 31. The lightening-coagulating conversion switch is also a mode conversion means for converting various operation modes of the fundus surgery apparatus 28.

The intraocular observation device 32 includes an objective lens 45, a variable magnification lens 46, a filter 47, an observed-beam splitting unit 48, an ocular lens 49, an imaging mirror 50, and a lateral-view mirror 51. The observed-beam splitting unit 48 is provided with at least a beam splitter 49a to split the observed light received from the tested eyeball through the objective lens 45, the variable magnification lens 46, and the filter 47 into the ocular lens 49, the imaging mirror 50, and the lateral-view mirror 51.

The optic system of the intraocular observation device 32 is provided with two optical paths corresponding to two eyeballs of an operator. With respect to almost all optical parts such as lenses except for the objective lens 45, one part is provided to each of the two optical paths.

The intraocular monitor 33 includes a CCD camera (imaging means) 52, a recorder (image recording means) 53, a display unit (display means) 54, and a monitor controller.

Now, surgery procedures using the apparatus 28 are described. Firstly, in-situ observation using fluorescence detection is performed. Fluorescein, that is, a kind of fluorescent agent is injected through a vein of an elbow of a tested person. After that, an eyeball is pierced with an intraocular illuminating probe 29, and fundus is observed by using a surgery microscope. Although an inserting position of the distal end portion of the intraocular illuminating probe 29 is just under an eyeball inserting hole, since the intraocular illuminating probe 29 is provided with an annular ring portion 35, it is possible to avoid the operator from excessively piercing the intraocular illuminating probe 29 into the eyeball with unawareness. The annular ring portion 35 may be integrally formed with the cannula 4. Alternatively, the annular ring portion 35 may be formed separately from the cannula 4. A material for the annular ring portion 35 is not limited to a specific one. A material having a strength capable of functioning as a stopper for avoiding excessive piercing of the intraocular illuminating probe 29 and having no harmful influence to the tested person can be suitably used.

A light having a wavelength of 489 nm is incident to the intraocular illuminating probe 29. The fluorescent light emitted from the fluorescein has a peak wavelength of 515 nm, so that a vessel tissue of retina can be seen with the fluorescent light and its pulsation can be also detected. A cause of pathological lesion of a diseased part can be determined by a well-known fundus illumination diagnosis method. As an example of the fundus illumination diagnosis method, there are a diagnosis method using fluorescein fluorescence illumination, a diagnosis method using indocyanine-green fluorescence illumination, a diagnosis method using a light interference laminagraphy.

After the cause of the pathological lesion is determined, the operator manipulates the lightening-coagulating conversion switch to select an exclusive surgery mode. Accordingly, the argon laser source 39 is in a state that the coagulating laser beam can be output. The operator removes the intraocular illuminating probe 29 from the interior of eyeball and inserts the photocoagulating probe 30 into the interior of eyeball. After the insertion, the operator illuminates a cell, a tumor, or a diseased part marked with the fluorescent agent with a coagulating laser beams from the argon laser source 39 such as a krypton red laser, an argon direct laser, and a krypton yellow laser through the photocoagulating probe 30 to practice surgery. As a surgical method, well-known outer fovea centralis photocoagulation therapy, fovea centralis photocoagulation therapy, photodynamic therapy, and transpupillary thermo-therapy are suitably used.

In addition to the fluorescein, a fluorescent agent using fluorescence resonance energy transfer, oregon green, or indocyanine-green may be used as the fluorescent agent.

In the light-illuminating probe 1 given in the present invention, due to the radiation before propagation to the lens portion, the radiation in the inner portion of the optical member, the radiation at the distal end portion of the light-radiating portion, or the diffusion at the transmissive diffusing plate, the illuminated spatial range of the external illuminating light can be enlarged, so that generation of back scattering light can be suppressed. Therefore, in the apparatus 28 using the intraocular illuminating probe 29 constructed with the light-illuminating probe 1, it is possible to prevent occurrence of flare caused from micro granules in a body fluid or a Ringer's solution located behind the end portion of the optical fiber. Accordingly, it is possible to provide an apparatus capable of obtaining an image having the so-called good "clearness".

Seventeenth Embodiment

Figure 49:
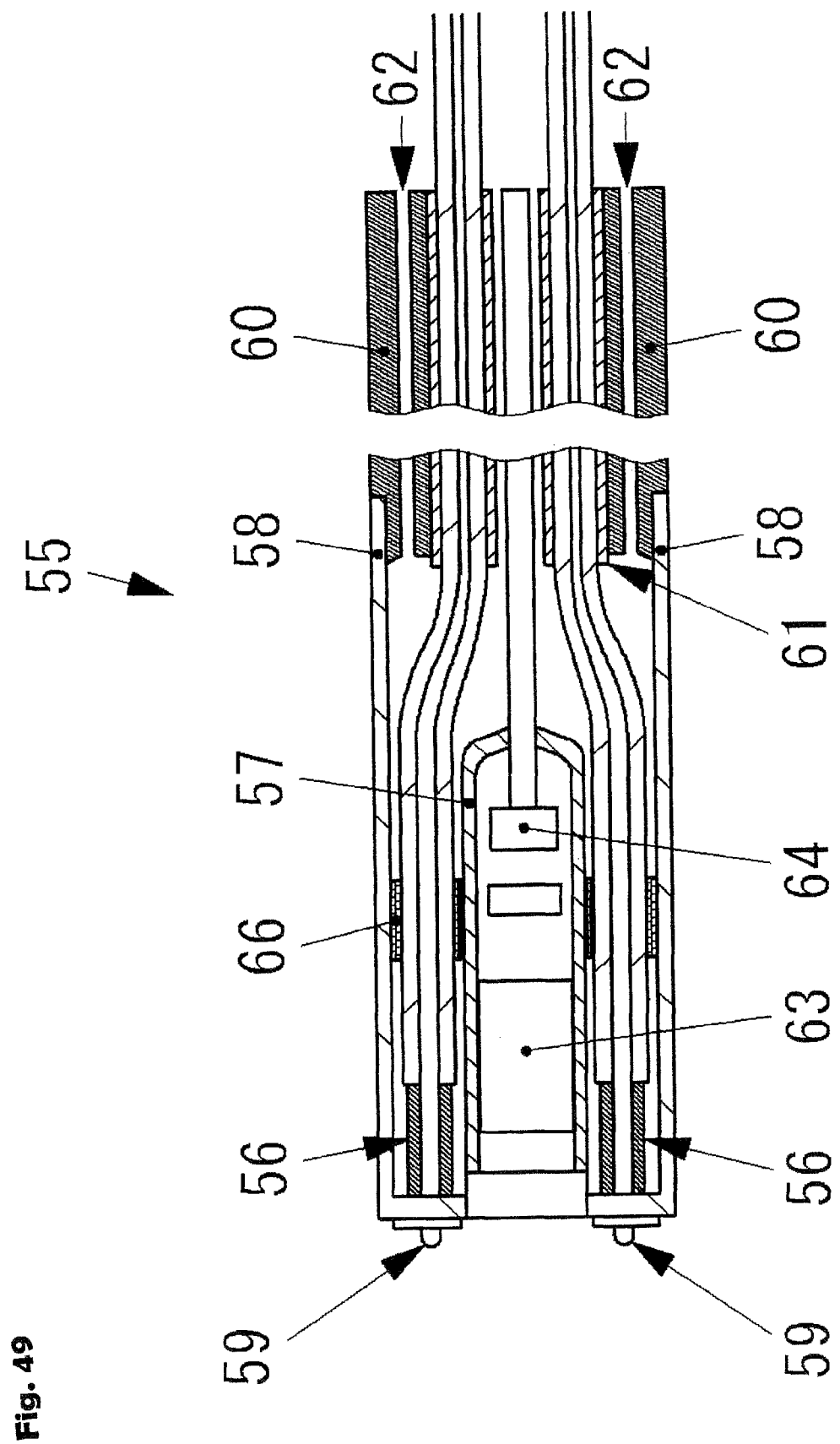
FIG. 49 is a schematic partial cross-sectional view illustrating a construction of an endoscope using the light-illuminating probe given in any one of the aforementioned embodiments.
Figure 50:
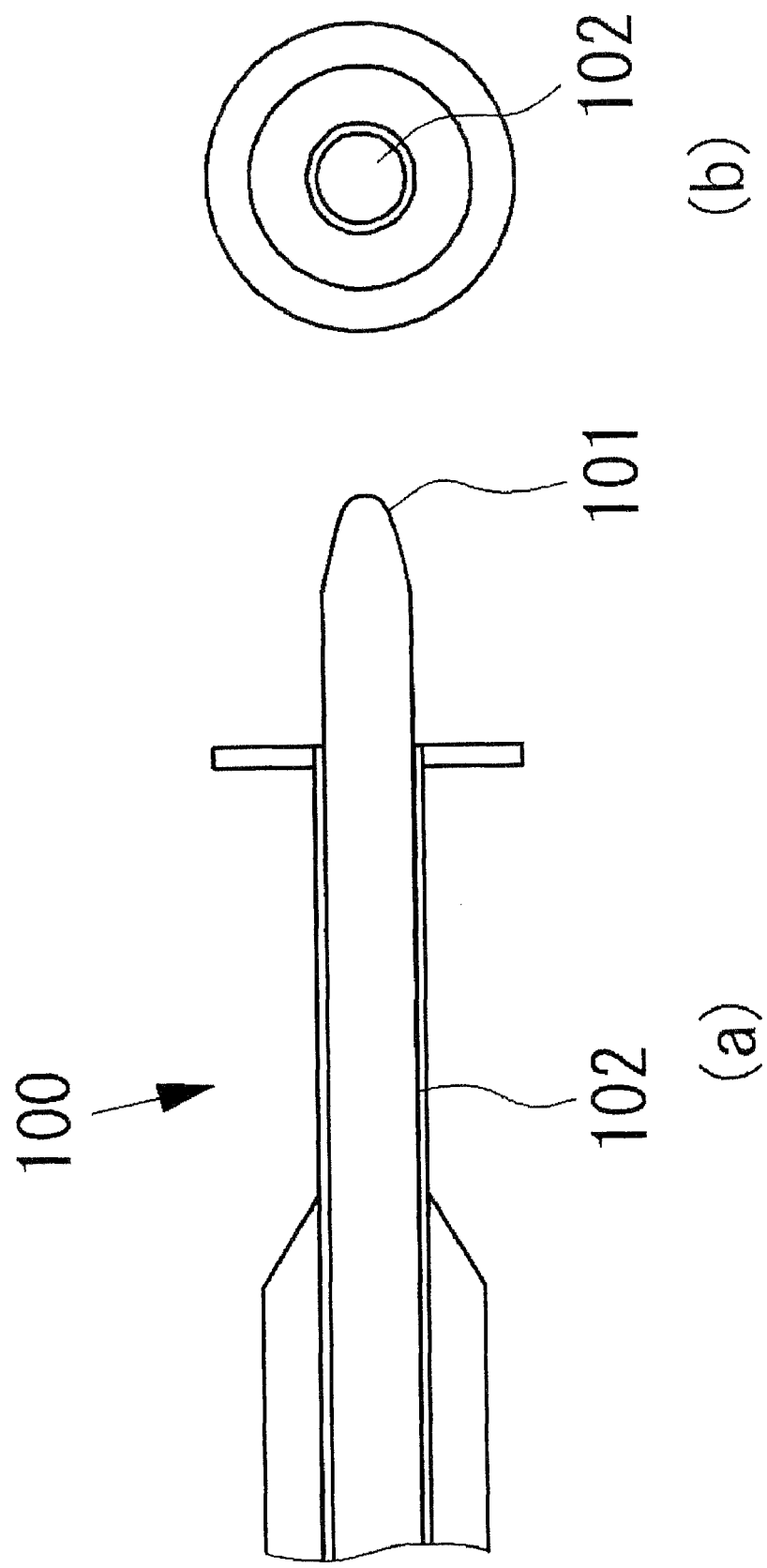
FIG. 50(a) is a partial side cross-sectional view illustrating a conventional light-illuminating probe.
FIG. 50(b) is a front view corresponding to FIG. 50(a).
Figure 51:
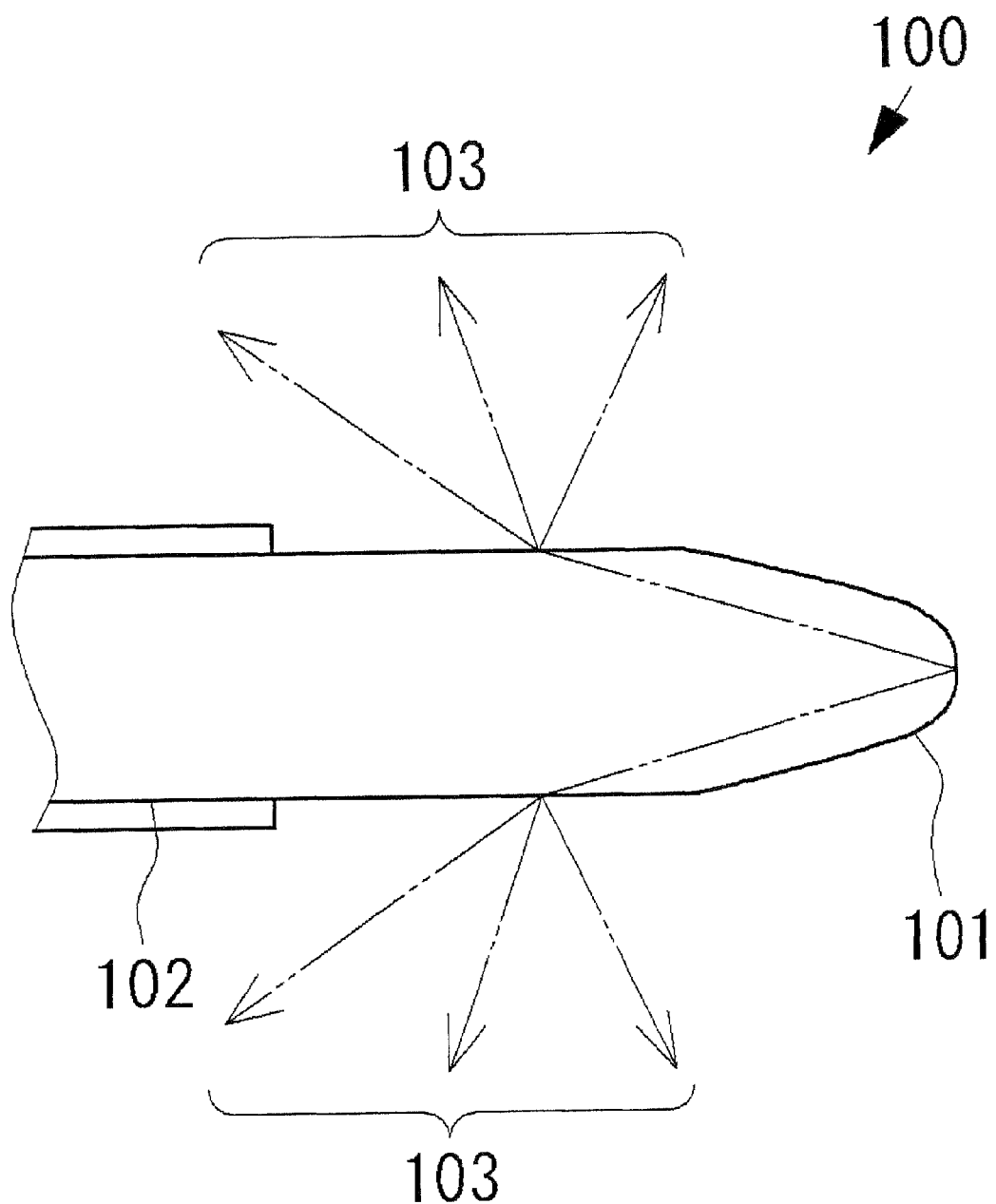
FIG. 51 is a view for explaining an occurrence of back scattering in the light-illuminating probe of FIG. 50.
Figure 52:
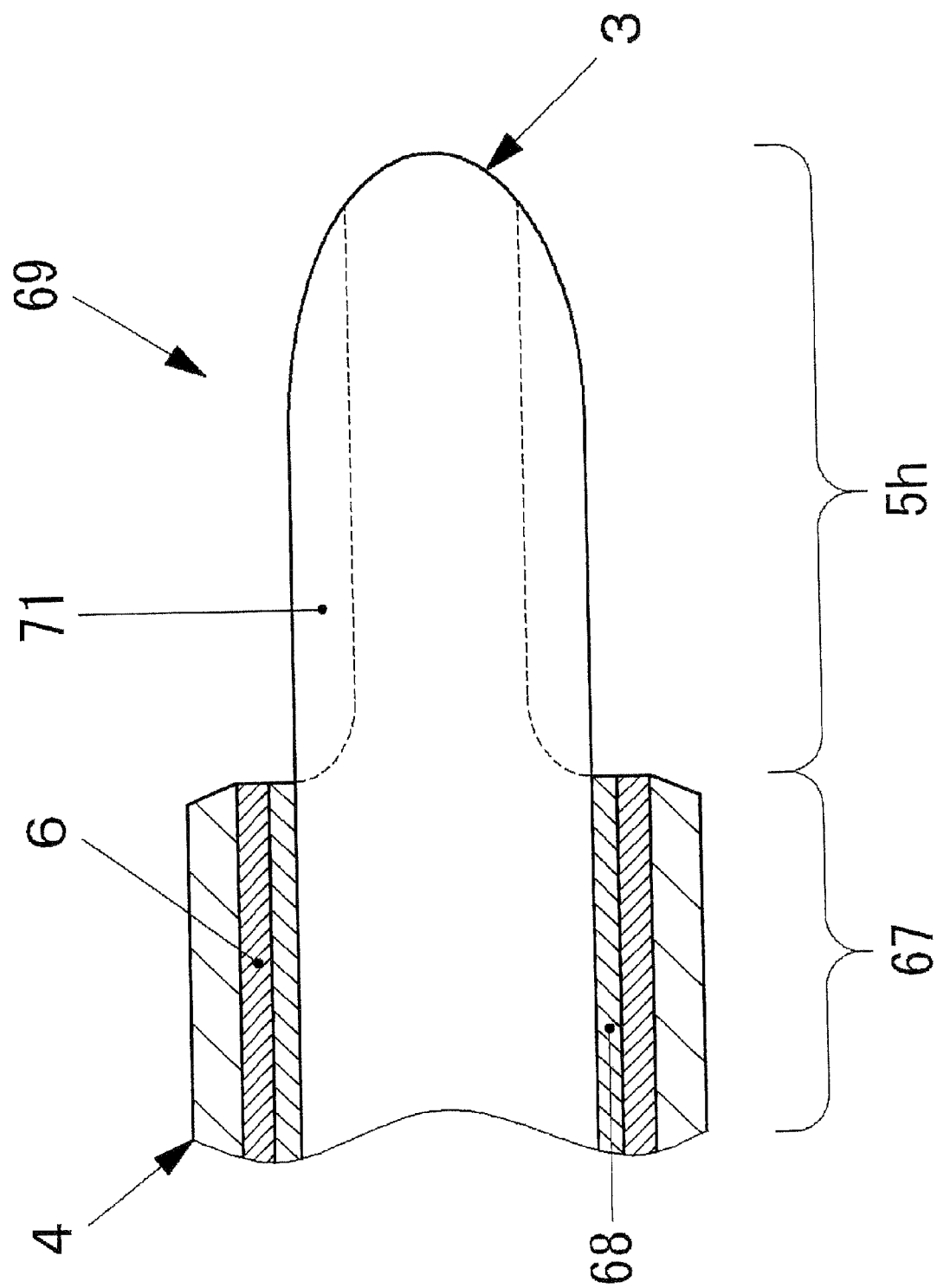
FIG. 52 is a schematic cross-sectional view illustrating a light-illuminating probe using a light-guiding optical fiber given in the present invention.
Figure 53:
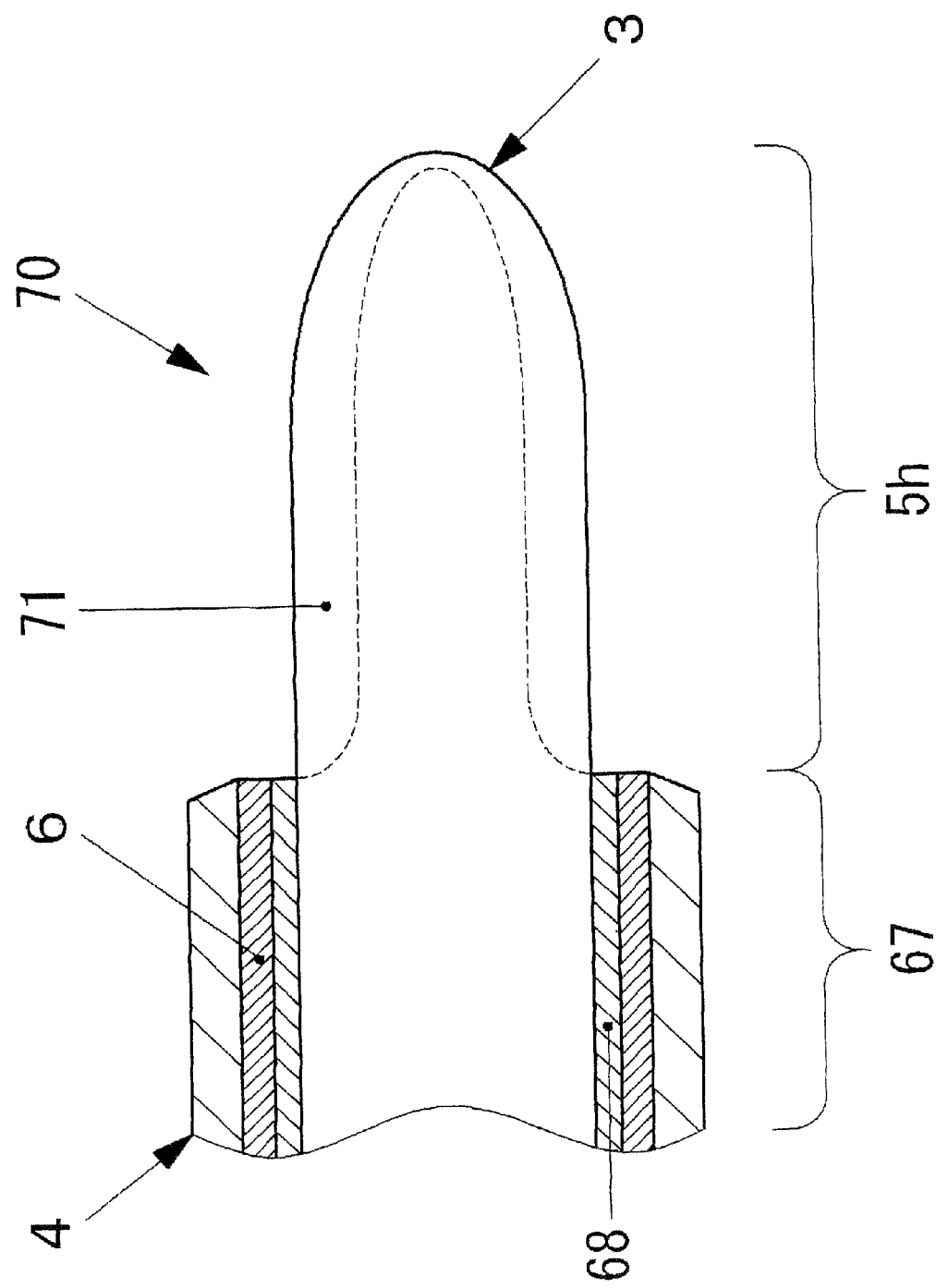
FIG. 53 is a schematic cross-sectional view illustrating a light-illuminating probe using a light-guiding optical fiber given in another embodiment of the present invention.
Figure 54:
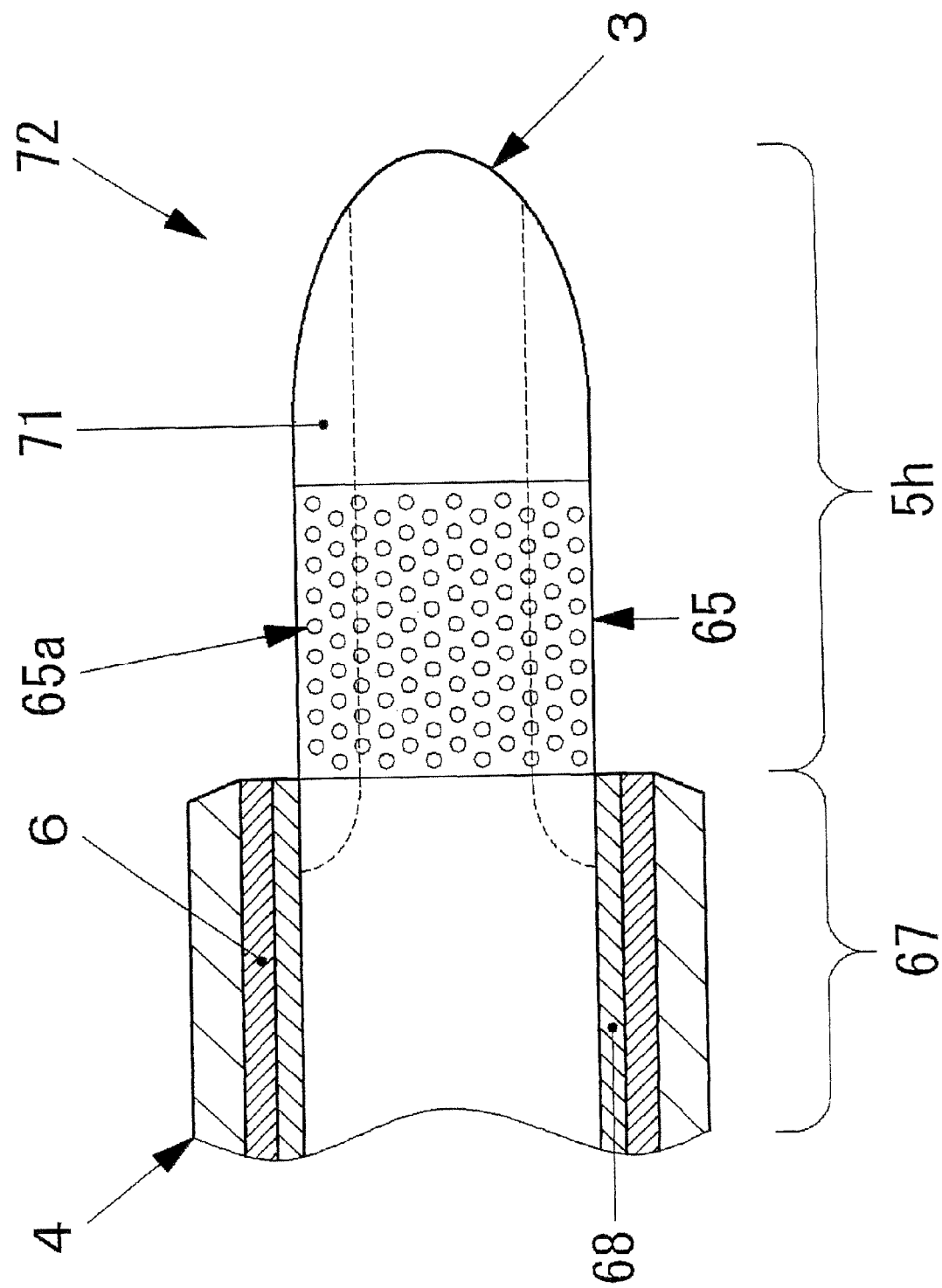
FIG. 54 is a schematic cross-sectional view illustrating a light-illuminating probe using a light-guiding optical fiber given in still another embodiment of the present invention.
Figure 55:
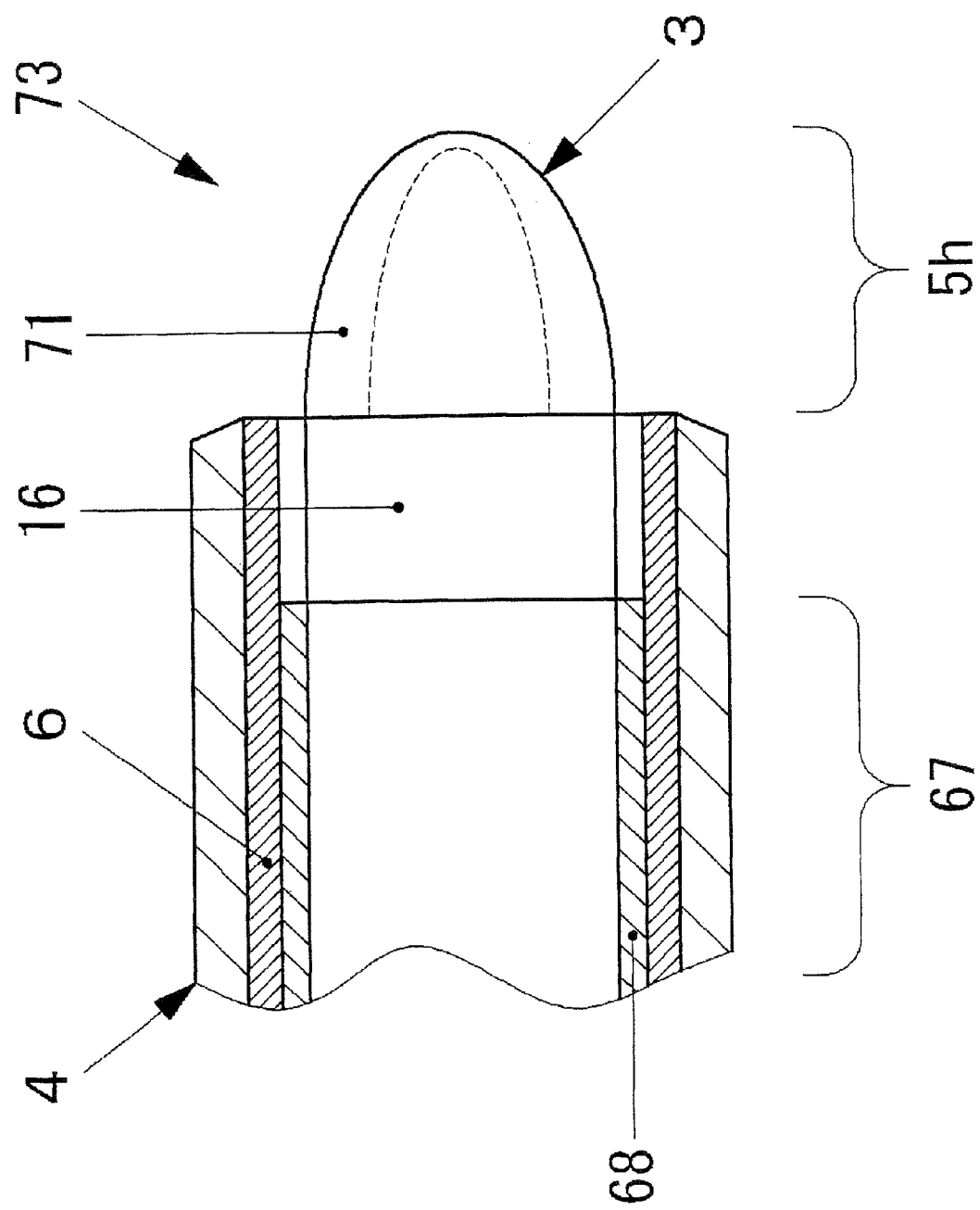
FIG. 55 is a schematic cross-sectional view illustrating a light-illuminating probe using a light-guiding optical fiber given in further still another embodiment of the present invention.
Figure 56:
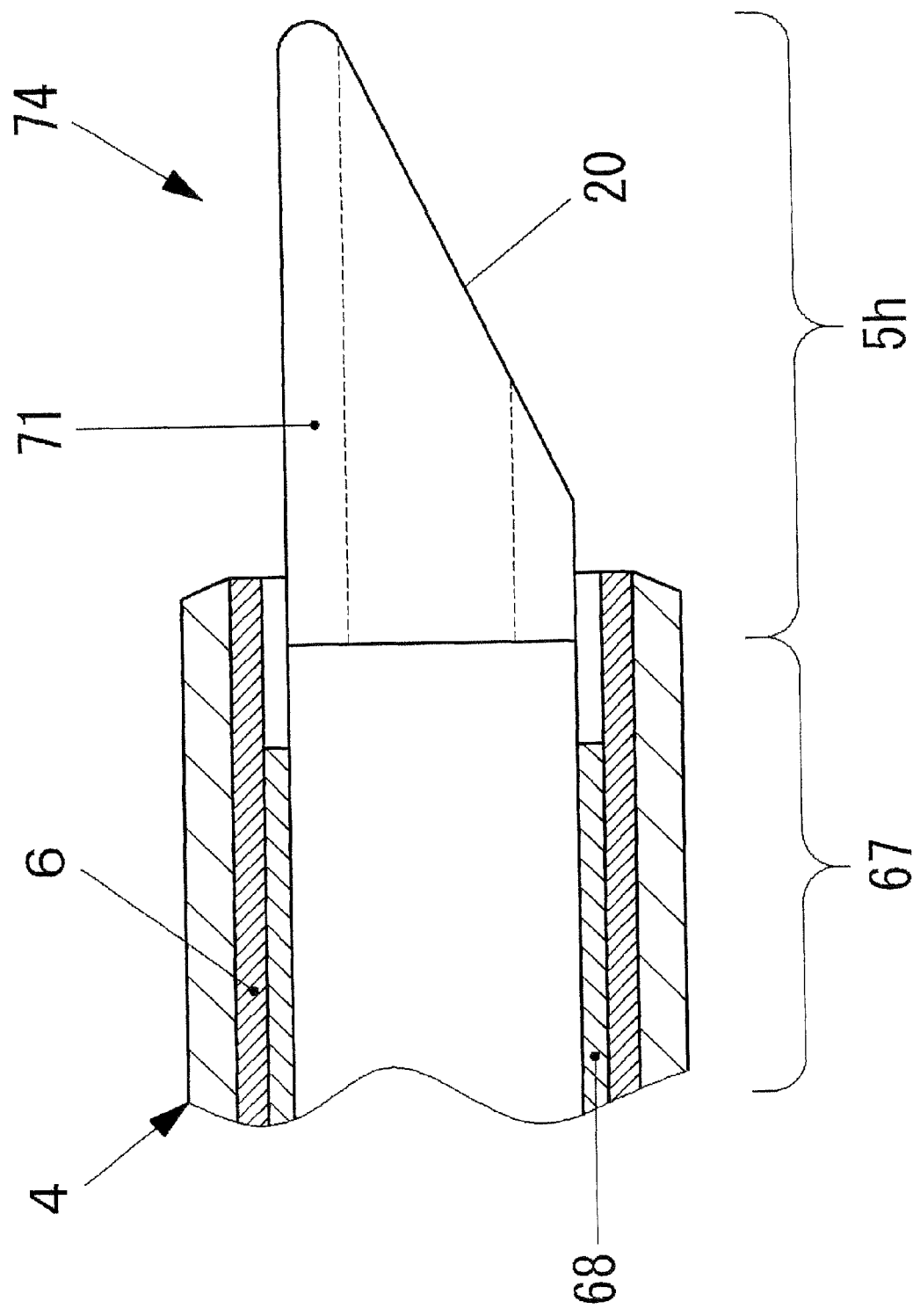
FIG. 56 is a schematic cross-sectional view illustrating a light-illuminating probe using a light-guiding optical fiber given in further still another embodiment of the present invention.

FIG. 49 illustrates a seventeenth embodiment of the present invention. FIG. 49 is a schematic partial cross-sectional view illustrating a construction of an endoscope 55 using a plurality of a light-illuminating probe 56 given in any one of the aforementioned first to fifteenth embodiments. The light-illuminating probe given in any one of the aforementioned first to fifteenth embodiments may be used as a light-illuminating probe 56 in FIG. 49.

Referring to FIG. 49, an optic system of the endoscope 55 is received in an optic sealing case 57. In the distal end portion of the endoscope 55, an optic system including a lens 63 and a camera 64, an end portion of the optical fiber 59 constituting a light-illuminating probe 56, a fiber guide 66, and a light-illuminating probe 56, and the aforementioned annular ring portion 35 (see FIG. 48) are disposed in a metal case 58. A rear portion thereof is formed with an elastic sheath 60 and an optical fiber housing pipe 61 and a Ringer's solution injection opening 62. The optical fiber 59 can be inserted or ejected through an inner portion of the optical fiber housing 61, so that the end portion of the optical fiber 59 can approach a diseased part or be put away in the metal case 58. The insertion and ejection of the optical fiber 59 are carried out by externally pushing and pulling the optical fiber 59. Being in accordance with the insertion or ejection of the optical fiber 59, the Ringer's solution is additionally injected or extravasated and discarded. The optic system is provided with the lens 63 and the camera 64. As an example of the camera 64, an electronic camera having a CCD or a CMOS device to output an electrical signal can be suitably used for in-situ observation.

In the light-illuminating probe given in the present invention, due to the radiation in the inner portion of the optical fiber or the optical member or the radiation at the transmissive diffusing plate, the illuminated spatial range of the external illuminating light can be enlarged, so that generation of back scattering light can be suppressed. Therefore, in the apparatus (endoscope 55) using the light-illuminating probe 56, it is possible to prevent occurrence of flare caused from micro granules in a body fluid or a Ringer's solution located behind the end portion of the optical fiber 59. Accordingly, it is possible to provide an apparatus capable of obtaining an image having the so-called good "clearness".

In addition, in the light-illuminating probes given in the present invention, since a wide illuminated spatial range of the external illuminating light can be obtained, a cell, a tumor, or a diseased part marked with a fluorescent agent can be easily detected.

The light-illuminating probes given in the present invention can be used for photo dynamic therapy by using such a property that the illuminating light emitted from the end portion thereof spatially spreads (be enlarged). This is because a peripheral-direction illumination of the optical fiber can be performed. Photofrin II (trade mark) is used as a medicinal agent. About 2 mg/Kg of the medicinal agent is injected into a diseased tissue through intravenous injection, and excimer laser (excimer dye laser) which can emit a laser beam with a reference energy density of 100 J/cm$^2$ through the light-illuminating probes given in the present invention are used to treat a stomach cancer or an esophagus cancer. The light-illuminating probes are disposed at the end portion of the endoscope. In case of percutaneous surgery, the light-illuminating probes given in the present invention may be directly inserted into a diseased part. Therefore, cells of the diseased part that is illuminated with the light are nercotized.

Additional embodiments of the present invention are illustrated in FIGS. 57(a) and 57(b). The same components as those of the aforementioned embodiments are denoted by the same reference numerals, and the description thereof is omitted and simplified. As illustrated in FIG. 57(a), a light-illuminating probe 1 is coupled with a distal end portion of a catheter 75. The catheter is inserted into a blood vessel which is narrowed by attachment of plaque or thrombus (indicated by reference numeral 77 in FIG. 57(b)), and the light-illuminating probe 1 is used to dissolve the plaque or thrombus 77 with a photoactive agent. FIG. 57(b) illustrates a usage state of the catheter. The light-illuminating probe 1 is coupled with a distal end portion of the catheter 75, and a medicinal agent ejection hole 81 is formed and a balloon 76 made of an extensible membrane for protecting a blood vessel is attached to the distal end portion of the catheter 1. An opening of the balloon 76 is closely attached to the catheter 75, and the balloon 76 is made of an extensible membrane having air or water expansibility and hermerically-sealing ability. The balloon 76 is expanded or contracted by pressurized air or water supply or depressurized air or water vent through an air/water passage 80 and an air or water supply/exhaust opening 79 which are disposed in an inner portion of the catheter 75. When the balloon 76 is expanded, the light-illuminating probe 1 is not directly in contact with the blood vessel wall 78. The plague or thrombus 77 may be formed uniformly on the blood vessel wall 78. However, in many cases, the plaque or thrombus 77 are formed non-uniformly on the blood vessel wall 78. By additionally using the balloon 76, the light-illuminating probe 1 can closely approach a site where the plaque or thrombus 77 is formed with a large thickness. As a result, the medicinal agent is activated at the site, so that the thick plaque or thrombus 77 can peel off or rapidly fuse into blood. Accordingly, only a small amount of the plaque or thrombus 77 remains, so that damage to the blood vessel wall 78 can be reduced. As a whole, the plaque or thrombus 77 can be effectively removed for a short time. A phtooxidative medicinal agent is used as the medicinal agent. The light source is an excimer dye laser. Alternatively, blue and ultraviolet LDs or LEDs may be used as the light source.

REFERENCE NUMERALS 1, 7, 8, 9, 10, 11, 13, 14, 15, 15', 17, 18, 19, 21, 22, 25, 26, 27, 69, 70, 72, 73, 74: light-illuminating probe
2, 2', 59: optical fiber
2a: core
2b, 2b': clad
2c: central portion
2d: peripheral portion
2d': hollow cylinder
3: lens portion
3a, 3b, 3b', 5e, 5e': distal end portion
4: cannula 5a, 5a', 5b, 5b', 5b'', 5c, 5c', 5d, 5f, 5f', 5g, 5h: light-radiating portion
5g': hollow site
6: hermetic seal
12: optical member
12a: distal portion
12b: adjacent portion
16: transmissive diffusing plate
20: flat plane
23, 24: step
28: fundus observing apparatus or fundus surgery apparatus
29: intraocular illuminating probe
30: photocoagulating probe
31: light source unit
31a: illuminating light-guiding cable
31b: coagulating light-guiding cable
32: intraocular observation device
33: intraocular monitor
34: hand piece
35: annular ring portion
36: light source controller
37: filter operation synchronizer
38: light output safety controller (light output safety control means)
39: argon ion laser source
40: guiding-light laser diode
41: first laser diode
42: optic system
43: laser output detector
44: laser beam filter
45: objective lens
46: variable magnification lens
47: filter
48: observed-beam splitting unit
49: ocular lens
49a beam splitter
50: imaging mirror
51: lateral-view mirror
52: CCD camera (imaging means)
53: recorder (image recording means)
54: display unit (display means)
55: endoscope
56: light-illuminating probe
57: optic sealing case
58: metal case
60: elastic sheath
61: optical fiber housing pipe
62: Ringer's solution injection opening
63: lens
64: camera
65: diffusing portion
65a: cavities
66: fiber guide
67: light-guiding optical fiber
68: metal layer
71: high-refractive-index layer
75: catheter
76: balloon
77: plaque or thrombus
78: blood vessel wall
79: air or water supply/exhaust opening
80: air/water passage
81: medicinal agent ejection hole
100: a conventional light-illuminating probe
101: end portion 101
102: optical fiber
103: back scattering light

What is claimed is:

1. A light-illuminating probe comprising:
a light-transmitting portion of an optical fiber constructed with at least a first dielectric material having a light transparency;
the light-transmitting portion being adapted to receive light from an external light source at one distal end of the optical fiber; and
a light-radiating portion constructed with a second dielectric material having a light transparency, the light-radiating portion being integrally formed at another distal end of the light transmitting portion of the optical fiber as an extension of the light-transmitting portion, the light-radiating portion being adapted to transmit the light from the external light source and to provide an enhanced spatial illuminating spread of the light having a beam of light projecting substantially in a longitudinal direction of the optical fiber from the external light source onto an object to be lighted,
wherein the first dielectric material constitutes the optical fiber including a core disposed in a center portion thereof and a clad disposed around the core,
wherein the clad has a refractive index smaller than the refractive index of the core,
wherein the light-radiating portion has a uniform refractive index distribution in which a refractive index of the light-radiating portion is equal to the refractive index of the core, and
wherein a distal portion of the light-radiating portion has a refractive index distribution in which a refractive index of the distal portion is higher than the refractive index of the core.

2. A light-illuminating probe comprising:
a light-transmitting portion of an optical fiber constructed with at least a first dielectric material having a light transparency;
a metal layer which covers the first dielectric material;
the light-transmitting portion being adapted to receive light from an external light source at one distal end of the optical fiber; and
a light-radiating portion constructed with a second dielectric material having a light transparency, the light-radiating portion being integrally formed at another distal end of the light transmitting portion of the optical fiber as an extension of the light-transmitting portion, the light-radiating portion being adapted to transmit the light from the external light source and to provide an enhanced spatial illuminating spread of the light having a beam of light projecting substantially in a longitudinal direction of the optical fiber from the external light source onto an object to be lighted,
wherein one flat plane or a plurality of flat planes are formed at a front end of the light-radiating portion not to be parallel to an axial direction of the light-radiating portion with an angle of less than 90 degree.

* * * * *